United States Patent
Szijártó et al.

(10) Patent No.: US 10,759,848 B2
(45) Date of Patent: Sep. 1, 2020

(54) KLEBSIELLA PNEUMONIAE O3 SPECIFIC ANTIBODIES

(71) Applicants: ARSANIS Biosciences GmbH, Vienna (AT); Max-Planck-Gesellschaft zur Förderung der Wissenschafter e. V., Munich (DE)

(72) Inventors: Valeria Szijártó, Vienna (AT); Gábor Nagy, Sopron (HU); Luis Guachalla, Vienna (AT); Katharina Ramoni, Vienna (AT); Adriana Badarau, Vienna (AT); Eszter Nagy, Vienna (AT); Tim Rollenske, Heidelberg (DE); Hedda Wardemann, Heidelberg (DE); Irina Mirkina, Vienna (AT)

(73) Assignees: ARSANIS Biosciences GmbH, Vienna (AT); Max-Planck-Gesellschaft zur Förderung der Wissenschaften e. V., Munich (DE)

( * ) Notice: Subject to any disclaimer, the term of this patent is extended or adjusted under 35 U.S.C. 154(b) by 0 days.

(21) Appl. No.: 16/321,523

(22) PCT Filed: Aug. 11, 2017

(86) PCT No.: PCT/EP2017/070446
§ 371 (c)(1),
(2) Date: Jan. 29, 2019

(87) PCT Pub. No.: WO2018/029346
PCT Pub. Date: Feb. 15, 2018

(65) Prior Publication Data
US 2019/0153077 A1    May 23, 2019

(30) Foreign Application Priority Data

Aug. 12, 2016  (EP) .................................. 16183950
Apr. 21, 2017  (EP) .................................. 17167462

(51) Int. Cl.
C07K 16/00       (2006.01)
C07K 16/12       (2006.01)
A61P 31/04       (2006.01)
A61K 39/00       (2006.01)

(52) U.S. Cl.
CPC .......... *C07K 16/1228* (2013.01); *A61P 31/04* (2018.01); *A61K 2039/505* (2013.01); *C07K 2317/21* (2013.01); *C07K 2317/24* (2013.01); *C07K 2317/33* (2013.01); *C07K 2317/565* (2013.01); *C07K 2317/732* (2013.01); *C07K 2317/76* (2013.01); *C07K 2317/92* (2013.01)

(58) Field of Classification Search
CPC ................................................ C07K 16/1228
See application file for complete search history.

(56) References Cited

U.S. PATENT DOCUMENTS

| | | |
|---|---|---|
| 6,331,415 B1 | 12/2001 | Cabilly et al. |
| 2002/0177170 A1 | 11/2002 | Luo et al. |
| 2004/0110226 A1 | 6/2004 | Lazar et al. |
| 2009/0181855 A1 | 7/2009 | Vasquez et al. |
| 2010/0056386 A1 | 3/2010 | Vasquez et al. |
| 2011/0236410 A1 | 9/2011 | Bakshi et al. |
| 2013/0197201 A1 | 8/2013 | Vasquez et al. |

FOREIGN PATENT DOCUMENTS

| | | |
|---|---|---|
| WO | 2003/074679 A2 | 9/2003 |
| WO | 2008/135446 A2 | 11/2008 |
| WO | 2009/036379 A2 | 3/2009 |
| WO | 2010/105256 A1 | 9/2010 |
| WO | 2012/009568 A2 | 1/2012 |

OTHER PUBLICATIONS

International Search Report dated Oct. 26, 2017 of corresponding International application No. PCT/EP2017/070446; 5 pgs.
Written Opinion dated Oct. 26, 2017 of corresponding International application No. PCT/EP2017/070446; 7 pgs.
International Preliminary Report on Patentability (Chapter I) dated Feb. 12, 2019 of corresponding International application No. PCT/EP2017/070446; 8pgs.
The extended European search report dated Oct. 27, 2016 of corresponding European application No. 16183950.1; 9pgs.
Benckert J. et al.; "The majority of intestinal IgA+ and IgG+ plasmablasts in the human gut are antigen-specific"; The Journal of Clinical Investigation; vol. 121; No. 5; May 2011; pp. 1946-1955.
Brodeur et al.; "4. Mouse-Human Myeloma Partners for the Production of Heterohybridomas"; Monoclonal Antibody Production Techniques and Applications; Marcel Dekker, Inc.; New York; 1987; pp. 51-63.
Curvall M. et al.; "Structural studies on the Klebsiella O group 3 Lipopolysaccharide"; ACTA Chemica Scandinavica; vol. 27; No. 7; 1973; pp. 2645-2649.
Galanos et al.; "Galactosamine-induced sensitization to the lethal effects of endotoxin"; Proc. Natl. Acad. Sci. USA; vol. 76; No. 11; Nov. 1979; pp. 5939-5943.
Greenfield L.K. et al.; "Biosynthesis of the Polymannose Lipopolysaccharide O-antigens from *Escherichia coli* Serotypes O8 and O9a Requires a Unique Combination of Single- and Multiple-active Site Mannosyltransferases"; The Journal of Biological Chemistry; vol. 287; No. 42; Oct. 12, 2012; pp. 35078-35091.
Greenfield L.K. et al.; "Domain Organization of the Polymerizing Mannosyltransferases Involved in Synthesis of the *Escherichia coli* O8 and O9a Lipopolysaccharide O-antigens"; The Journal of Biological Chemistry; vol. 287; No. 45; Nov. 2, 2012; pp. 38135-38149.

(Continued)

*Primary Examiner* — Albert M Navarro
(74) *Attorney, Agent, or Firm* — Maier & Maier, PLLC

(57) ABSTRACT

A cross-neutralizing monoclonal antibody that specifically recognizes a cross-reactive epitope of the lipopolysaccharide (LPS) antigen structure of *Klebsiella pneumoniae*, which is an O3b epitope, cross-reacting with an O3a epitope and an O3 epitope, wherein the antibody is characterized by specific CDR sequences or VH and VL sequences.

19 Claims, 16 Drawing Sheets
Specification includes a Sequence Listing.

(56) References Cited

OTHER PUBLICATIONS

Hansen D.S, et al.; "Klebsiella pneumoniae Lipo-polysaccharide O Typing: Revision of Prototype Strains and O-Group Distribution among Clinical Isolates from Different Sources and Countries"; The Journal of Clinical Microbiology; vol. 37; No. 1; Jan. 1999; pp. 56-62.

Kerkman P.F. et al.; "Identification and characterisation of citrullinated antigen-specific B cells in peripheral blood of patients with rheumatoid arthritis"; Ann. Rheum. Dis.; vol. 75; 2016; pp. 1170-1176.

Kido N. et al.; "Production of Monoclonal Antibody Discriminating Serological Difference in *Escherichia coli* O9 and O9a Polysaccharides"; Microbiol. Immunol.; vol. 41; No. 7; 1997; pp. 519-525.

Kido N. et al.; "A Single Amino Acid Substitution in a Mannosyltransferase, WbdA, Converts the *Escherichia coli* O9 Polysaccharide into O9a: Generation of a New O-Serotype Group"; Journal of Bacteriology; vol. 1 82; No. 9; May 2000; pp. 2567-2573.

Kohler G. et al.; "Continuous cultures of fused cells secreting antibody of predefined specificity"; Nature; vol. 256; Aug. 7, 1975; pp. 495-497.

Kozbor D. et al.; "A Human Hybrid Myeloma for Production of Human Monoclonal Antibodies"; The Journal of Immunology; vol. 133; No. 6; Dec. 1984; pp. 3001-3005.

Kubler-Kielb J. et al.; "Identification of the methyl phosphate substituent at the non-reducing terminal mannose residue of the O-specific polysaccharides of Klebsiella pneumoniae O3, Hafnia alvei PCM 1223 and *Escherichia coli* O9/O9a LPS"; Carbohydr Res.; vol. 347; No. 1; Jan. 10, 2012; pp. 186-188.

Lee et al.; "Expression and functional reconstitution of a recombinant antibody (Fab') specific for human apolipoprotein B-100"; Journal of Biotechnology; vol. 101; 2003; pp. 189-198.

Lefranc et al.; "IMGT, the international ImMunoGeneTics database"; Nucleic Acids Research; vol. 27; No. 1; 1999; pp. 209-212.

Lefranc et al.; "IMGT unique numbering for immunoglobulin and T cell receptor variable domains and Ig superfamily V-like domains"; Developmental and Comparative Immunology; vol. 27; 2003; pp. 55-77.

Lukasiewicz J. et al.; "Complete Lipopolysaccharide of Plesiomonas shigelloides O74:H5 (Strain CNCTC 144/92). 2. Lipid A, Its Structural Variability, the Linkage to the Core Oligosaccharide, and the Biological Activity of the Lipopolysaccharide"; Biochemistry; vol. 45; 2006; pp. 10434-10447.

Murugan R. et al.; "Direct high-throughput amplification and sequencing of immunoglobulin genes from single human B cells"; European Journal of Immunology; Technical comment; vol. 45; 2015; pp. 2698-2700.

Parolis L.A.S. et al.; "Structural studies of the O-antigen polysaccharide of *Escherichia coli* O9a"; Carbohydrate Research; vol. 155; 1986; p. 272-276.

Pollack et al.; "Human Monoclonal Antibodies That Recognize Conserved Epitopes in the Core-Lipid A Region of Lipopolysaccharides"; Journal of Clinical Investigation, Inc.; vol. 79; May 1987; pp. 1421-1430.

Prassler et al.; "In vitro affinity maturation of HuCAL antibodies: complementarity determining region exhange and RapMAT technology"; Immunotherapy; vol. 1; No. 4; 2009; pp. 571-583.

Rojas O. L. et al.; "Characterization of rotavirus specific B cells and their relation with serological memory"; Virology; vol. 380; No. 2; Oct. 25, 2008; pp. 234-242.

Scheid J. et al.; "A method for identification of HIV gp140 binding memory B cells in human blood"; J. Immunol Methods; vol. 343; No. 2; Apr. 15, 2009; pp. 65-67.

Sheedy C. et al.; "Isolation and affinity maturation of haptenspecific antibodies"; Biotechnology Advances; vol. 25; 2007; pp. 333-352.

Sugiyama et al.; "Generation of *Escherichia coli* O9a Serotype, a Subtype of *E coli* O9, by Transfer of the wb* Gene Cluster of Klebsiella O3 into *E. coli* via Recombination"; Journal of Bacteriology; vol. 180; No. 10; May 1998; pp. 2775-2778.

Tiller T. et al.; "Efficient generation of monoclonal antibodies from single human B cells by single cell RT-PCR and expression vector cloning"; J. Immunol Methods; vol. 329; Jan. 1, 2008; pp. 112-124.

Trautmann et al.; "A Murine Monoclonal Antibody Defines a Unique Epitope Shared by Klebsiella Lipopolysaccharides"; Infection and Immunity; vol. 62; No. 4; Apr. 1994; pp. 1282-1288.

Trautmann et al.; "O-Antigen Seroepidemiology of Klebsiella Clinical Isolates and Implications for Immunoprophylaxis of Klebsiella Infections"; Clinical and Diagnostic Laboratory Immunology; vol. 4; No. 5; Sep. 1994; pp. 550-555.

Van der Meer et al.; "Binding Studies of a Monoclonal Antibody Specific for 3-Deoxy-D-manno-Octulosonic Acid with a Panel of Klebsiella pneumoniae Lipopolysaccharides Representing All of the O Serotypes"; Infection and Immunity; vol. 62; No. 3; Mar. 1994; pp. 1052-1057.

Vinogradov E. et al.; "Structures of Lipopolysaccharides from Klebsiella pneumoniae Eluicidation of the structure of the linkage region between core and polysaccharide O chain and identification of the residues at the non-reducing termini of the O chains"; The Journal of Biological Chemistry; vol. 277; No. 28; Jul. 12, 2002; pp. 25070-25081.

Wardemann H. et al.; "Predominant Autoantibody Production by Early Human B Cell Precursors"; Science; vol. 301; Sep. 5, 2003; pp. 1374-1377.

Wibbenmeyer et al.; "Cloning, expression, and characterization of the Fab fragment of the anti-lysozyme antibody HyHEL-5"; Biochimica et Biophysica Acta; vol. 1430; 1999; pp. 191-202.

Yokochi et al.; "Novel Adjuvant Action of Lipopolysaccharides That Possess Mannose Homopolysaccharides as O-Specific Polysaccharides on Immune Responses to Nonimmunogenic Autoantigens in Mice"; Infection and Immunity; vol. 60; No. 11; Nov. 1992; pp. 4953-4956.

Fig. 1a

Table 1 a: CDR sequences using Kabat nomenclature

VH

| nucleic acid sequence SEQ ID VH | amino acid sequence SEQ ID VH | mAb Name | SEQ ID CDR1 | VH CDR1 | SEQ ID CDR2 | VH CDR2 | SEQ ID CDR3 | VH CDR3 |
|---|---|---|---|---|---|---|---|---|
| 1 | 11 | UaLPLO3-601 | 21 | RNWMS | 22 | DIKADGSEKVYLDSMKG | 23 | GPSYGDRCDYLDH |
| 2 | 12 | UaLPLO3-095 | 24 | NYAIH | 25 | AIGGDGHSTYWEAVKG | 26 | EGYSSGRCGSFDH |
| 3 | 13 | UaLPLO3-208L | 27 | NFNYYWG | 28 | TIYNGNTYYNPSLKS | 29 | DSGSVERFDH |
| 4 | 14 | UaLPLO3-547 | 30 | RHWMT | 31 | DIKKDGSEENYVDTVKG | 32 | GPSYGDRSDYLDN |
| 5 | 15 | UaLPLO3-555 | 30 | RHWMT | 31 | DIKKDGSEENYVDTVKG | 32 | GPSYGDRSDYLDN |
| 71 | 68 | MPG601 C108S | 21 | RNWMS | 22 | DIKADGSEKVYLDSMKG | 74 | GPSYGDRSDYLDH |
| 72 | 69 | MPG601 H97Y | 21 | RNWMS | 22 | DIKADGSEKVYLDSMKG | 23 | GPSYGDRCDYLDH |
| 73 | 70 | MPG601 C108S/H97Y | 21 | RNWMS | 22 | DIKADGSEKVYLDSMKG | 74 | GPSYGDRSDYLDH |

VL

| nucleic acid sequence SEQ ID VL | amino acid sequence SEQ ID VL | mAb Name | SEQ ID VL CDR1 | VL CDR1 | SEQ ID VL CDR2 | VL CDR2 | SEQ ID VL CDR3 | VL CDR3 |
|---|---|---|---|---|---|---|---|---|
| 6 | 16 | UaLPLO3-601 | 33 | RSSQSLLEPNGHNYVD | 34 | LGSNRAS | 35 | MQPLQTPYT |
| 7 | 17 | UaLPLO3-095 | 36 | RASQSISSWLA | 37 | KASSLES | 38 | QQYNDYSPA |
| 8 | 18 | UaLPLO3-208L | 39 | SGSSSNIGSKTVN | 40 | NDNQRPS | 41 | AAWDDNFNGLL |
| 9 | 19 | UaLPLO3-547 | 42 | RSSQWLLESNGHNYLD | 34 | LGSNRAS | 43 | MQPLKLPYT |
| 10 | 20 | UaLPLO3-555 | 42 | RSSQWLLESNGHNYLD | 34 | LGSNRAS | 43 | MQPLKLPYT |

Fig. 1b

Table 1 b: CDR sequences using IMGT nomenclature

VH

| nucleic acid sequence SEQ ID VH | amino acid sequence SEQ ID VH | SEQ ID CDR1 | VH CDR1 | SEQ ID CDR2 | VH CDR2 | SEQ ID CDR3 | VH CDR3 |
|---|---|---|---|---|---|---|---|
| 1 | 11 | 44 | GFTFSRNW | 45 | IKADGSEK | 46 | ARGPSYGDRCDYLDH |
| 2 | 12 | 47 | GFTFNNYA | 48 | IGGDGHST | 49 | AREGYSSGRCGSFDH |
| 3 | 13 | 50 | GVSISNFNYY | 51 | IYYNGNT | 52 | AWDSGSVERFDH |
| 4 | 14 | 53 | GFDFSRHW | 54 | IKKDGSEE | 55 | ARGPSYGDRSDYLDN |
| 5 | 15 | 53 | GFDFSRHW | 54 | IKKDGSEE | 55 | ARGPSYGDRSDYLDN |
| 71 | 68 | 44 | GFTFSRNW | 45 | IKADGSEK | 67 | ARGPSYGDRSDYLDH |
| 72 | 69 | 44 | GFTFSRNW | 45 | IKADGSEK | 46 | ARGPSYGDRCDYLDH |
| 73 | 70 | 44 | GFTFSRNW | 45 | IKADGSEK | 67 | ARGPSYGDRSDYLDH |

VL

| nucleic acid sequence SEQ ID VL | amino acid sequence SEQ ID VL | SEQ ID VL CDR1 | VL CDR1 | SEQ ID VL CDR2 | VL CDR2 | SEQ ID VL CDR3 | VL CDR3 |
|---|---|---|---|---|---|---|---|
| 6 | 16 | 56 | QSLLEPNGHNY | 57 | LGS | 58 | MQPLQTPYT |
| 7 | 17 | 59 | QSISSW | 60 | KAS | 61 | QQYNDYSPA |
| 8 | 18 | 62 | SSNIGSKT | 63 | NDN | 64 | AAWDDNFNGLL |
| 9 | 19 | 65 | QWLLESNGHNY | 57 | LGS | 66 | MQPLKLPYT |
| 10 | 20 | 65 | QWLLESNGHNY | 57 | LGS | 66 | MQPLKLPYT |

Fig. 2a: nucleotide sequences of antibody heavy and light chains, variable domains SEQ ID 1
GAAGTGCAGCTGGTGGAGTCTGGGGGAGGCTTGGTCCAGCCTGGGGGGTCCCTGA
GACTCTCCTGTGAAGCCTCTGGCTTCACCTTTAGTAGGAATTGGATGAGTTGGGTCC
GCCAGATTCCAGGGAAGGGGCTGGAGTGGGTGGCCGACATAAAGGCAGATGGAAG
TGAGAAAGTCTATCTGGACTCTATGAAGGGCCGATTAACCATTTCCAGAGACAACG
CCAGGAATTTATTGTATCTGCAAATGGACAGCCTGAGAGTCGAGGACTCGGCCCTA
TATCACTGTGCGAGAGGCCCCTCTTATGGTGACAGGTGTGACTACTTGGACCACTG
GGGCCGGGGAGCCCTGGTCACCGTCTCCTCAG SEQ ID 6
GATATTGTGATGACTCAGTCTCCACTCTCCCTGCCCGTCACCCCAGGAGAGCCGGC
CTCCATCTCCTGCAGGTCTAGTCAGAGCCTCCTGGAGCCTAATGGACACAACTATG
TGGATTGGTACCAGCAAAAGCCAGGGCAGTCTCCACGGCTCCTGATCTATTTGGGT
TCTAACCGGGCCTCCGGGGTCCCTGACAGGTTCAGTGGCAGTGGAGGAGGCACAG
ACTTTACACTGAAAATCAGCAGAGTGGAGGCTGAGGATGTTGGGCTTTATTACTGC
ATGCAACCTCTGCAAACTCCGTACACTTTTGGCCAGGGGACCAAGCTGGAGATCAA
AC SEQ ID 2
GAGGTGCAGCTGTTGGAGTCTGGGGGAGGCTTGGTGCAGCCGGGGGGGTCCCTGA
GACTCTCCTGTGCAACCTCCGGATTCACCTTTAACAACTATGCCATCCACTGGGTCC
GCCAGGCTCCAGGGAAGGGGCTGGAATGGGTCTCAGCCATTGGTGGTGATGGTCAT
TCGACATATTATGTAGAGGCCGTGAAGGGCCGGTTCACCATCTCCAGTGACAGTTC
CAAGAACACGGTATATCTGCAGGTGAACAGCCTGAGACCCGAGGACACGGCCCTA
TATTATTGTGCGAGAGAGGGCTATAGTAGTGGCCGGTGCGGGTCTTTTGACCACTG
GGGCCAGGGAACCCTGGTCACCGTCTCCTCAG SEQ ID 7
GACATCCAGATGACCCAGTCTCCTTCCACCCTGTCTGCATCTGTTGGAGACAGAGT
CACCATCACTTGCCGGGCCAGTCAGAGTATCAGTAGCTGGTTGGCCTGGTATCAGC
AGAAACCAGGAAAAGCCCCTAAGCTCCTGATCAATAAGGCGTCTAGTTTGGAAAG
TGGGGTCCCATCAAGATTCAGCGGCAGCGGATCTGGGACAGAATTCACTCTCACCA
TCAGCAGCCTGCAGCCTGATGATTTTGCAACTTATTACTGCCAACAGTATAATGATT
ATTCTCCCGCATTCGGCCAAGGGACCAAGGTGGAGATCAAAC SEQ ID 3
CAGCTGCAGCTGCAGGAGTCGGGCCCAGGACTGGTGAAGCCTTCGGAGACCCTGTC
CCTCACCTGCTCTGTCTCTGGTGTCTCCATCAGCAATTTTAATTACTACTGGGGCTG
GGTCCGCCAGCCCCCAGGGAAGCCGCTGGAGTGGATTGGGACTATCTATTATAATG
GAAACACCTACTACAACCCGTCCCTCAAGAGTCGAGTCACCATATCCGTAGACACG
TCCAAGACTCAGTTGTCCCTGAAGCTGCTCTCTGTGACCGCCGCAGACACGGCTGT
GTATTACTGTGCGTGGGACTCCGGTTCTGTGGAAGATTTGACCACTGGAGCCAGG
GAACCCTGGTCACCGTCTCCTCAG

Fig. 2a continued

SEQ ID 8
CAGTCTGTGCTGACTCAGCCACCCTCAACGTCTGGGACCCCCGGGCAGAGGGTCAC
CATCTCTTGTTCTGGAAGCAGCTCCAACATCGGAAGTAAAACTGTCAACTGGTACA
AGCAAGTCCCAGGAACGGCCCCCAAACTCCTCGTCTTTAATGATAATCAACGGCCC
TCCAGGGTCCCTGACCGATTCTCTGGGTCCAAGTCTGGCACGTCAGCCTCCCTGGCC
ATCAGTGGGCTCCAGTCTGACGATGAGGCTGATTATTACTGTGCAGCGTGGGATGA
CAACTTCAATGGCCTGCTATTCGGCGGAGGGACCAAGCTGACCGTCCTA

SEQ ID 4
GAAGTGCAGCTGGTGGAGTCTGGGGGAGGCTTGGTCCAGCCGGGGGGGTCCCTGA
GACTCTCCTGTTCAACGTCTGGATTCGACTTTAGTAGGCATTGGATGACCTGGGTCC
GACAGGCTCCAGGGAAGGGGCTGGAGTGGGTGGCCGACATAAAGAAAGATGGAA
GTGAGGAGAACTATGTGGACACTGTGAAGGGCCGACTCACCATCTCCAGAGACAA
CGCCAGGAGGTCACTCTATCTGCAAATGAACAGCCTGAGAACCGACGACACGGCC
GTGTATTATTGTGCGAGAGGACCCTCGTATGGTGACCGGAGTGACTACCTGGACAA
CTGGGGCCAGGGGACCCTGGTCACCGTCTCCTCAG

SEQ ID 9
GATATTGTGATGACTCAGTCTCCTCTCTCCCTGGCCGTCACCCCTGGAGAGCCGGCC
TCCATCTCCTGCAGGTCTAGTCAGTGGCTCCTGGAGAGTAATGGACACAACTATTT
GGATTGGTACCTGCAGAAGCCAGGGCAGTCTCCACAACTCCTGATCCCTTTGGGTT
CTAATCGGGCCTCCGGGGTCCCTGACAGGTTCAGTGGCAGTGGGTCAGGCACAGAT
TTTACACTGACAATCAGCAGAGTGGAGGCTGAGGATGTTGGGGTTTATTATTGCAT
GCAACCTCTAAAACTTCCGTACACTTTTGGCCAGGGGACCAAGCTGGAGATCAAAC

SEQ ID 5
GAAGTGCAGCTGGTGGAGTCTGGGGGAGGCTTGGTCCAGCCGGGGGGGTCCCTGA
GACTCTCCTGTTCAACGTCTGGATTCGACTTTAGTAGGCATTGGATGACCTGGGTCC
GACAGGCTCCAGGGAAGGGGCTGGAGTGGGTGGCCGACATAAAGAAAGATGGAA
GTGAGGAGAACTATGTGGACACTGTGAAGGGCCGACTCACCATCTCCAGAGACAA
CGCCAGGAGGTCACTCTATCTGCAAATGAACAGCCTGAGAACCGACGACACGGCC
GTGTATTATTGTGCGAGAGGACCCTCGTATGGTGACCGGAGTGACTACCTGGACAA
CTGGGGCCAGGGGACCCTGGTCACCGTCTCCTCAG

SEQ ID 10
GATATTGTGATGACTCAGTCTCCTCTCTCCCTGGCCGTCACCCCTGGAGAGCCGGCC
TCCATCTCCTGCAGGTCTAGTCAGTGGCTCCTGGAGAGTAATGGACACAACTATTT
GGATTGGTACCTGCAGAAGCCAGGGCAGTCTCCACAACTCCTGATCTCTTTGGGTT
CTAATCGGGCCTCCGGGGTCCCTGACAGGTTCAGTGGCAGTGGGTCAGGCACAGAT
TTTACACTGACAATCAGCAGAGTGGAGGCTGAGGATGTTGGGGTTTATTATTGCAT
GCAACCTCTAAAACTTCCGTACACTTTTGGCCAGGGGACCAAGCTGGAGATCAAAC

Fig. 2a continued

SEQ ID 71 (VL is e.g. SEQ ID 6)
GAGGTGCAGCTGGTGGAATCTGGCGGAGGACTGGTGCAGCCTGGCGGCTCTCTGA
GACTGTCTTGCGAGGCCTCCGGCTTCACCTTCTCCCGGAACTGGATGTCCTGGGTGC
GACAGATCCCTGGCAAGGGCCTGGAATGGGTGGCCGACATCAAGGCCGACGGCTC
CGAGAAGGTGTACCTGGACTCTATGAAGGGCCGGCTGACCATCTCCCGGGACAAC
GCCAGAAACCTGCTGTACCTGCAGATGGACTCCCTGCGGGTGGAAGATTCCGCCCT
GTACCACTGTGCCAGAGGCCCCTCTTACGGCGACAGATcCGACTACCTGGACCATT
GGGGCAGAGGCGCCCTCGTGACAGTGTCCTCT

SEQ ID 72 (VL is e.g. SEQ ID 6)
GAGGTGCAGCTGGTGGAATCTGGCGGAGGACTGGTGCAGCCTGGCGGCTCTCTGA
GACTGTCTTGCGAGGCCTCCGGCTTCACCTTCTCCCGGAACTGGATGTCCTGGGTGC
GACAGATCCCTGGCAAGGGCCTGGAATGGGTGGCCGACATCAAGGCCGACGGCTC
CGAGAAGGTGTACCTGGACTCTATGAAGGGCCGGCTGACCATCTCCCGGGACAAC
GCCAGAAACCTGCTGTACCTGCAGATGGACTCCCTGCGGGTGGAAGATTCCGCCCT
GTACtACTGTGCCAGAGGCCCCTCTTACGGCGACAGATGCGACTACCTGGACCATTG
GGGCAGAGGCGCCCTCGTGACAGTGTCCTCT

SEQ ID 73 (VL is e.g. SEQ ID 6)
GAGGTGCAGCTGGTGGAATCTGGCGGAGGACTGGTGCAGCCTGGCGGCTCTCTGA
GACTGTCTTGCGAGGCCTCCGGCTTCACCTTCTCCCGGAACTGGATGTCCTGGGTGC
GACAGATCCCTGGCAAGGGCCTGGAATGGGTGGCCGACATCAAGGCCGACGGCTC
CGAGAAGGTGTACCTGGACTCTATGAAGGGCCGGCTGACCATCTCCCGGGACAAC
GCCAGAAACCTGCTGTACCTGCAGATGGACTCCCTGCGGGTGGAAGATTCCGCCCT
GTACtACTGTGCCAGAGGCCCCTCTTACGGCGACAGATcCGACTACCTGGACCATTG
GGGCAGAGGCGCCCTCGTGACAGTGTCCTCT

Fig. 2b: amino acid sequences of antibody heavy and light chains, variable domains SEQ ID 11
EVQLVESGGGLVQPGGSLRLSCEASGFTFSRNWMSWVRQIPGKGLEWVADIKADGSEKVY
LDSMKGRLTISRDNARNLLYLQMDSLRVEDSALYHCARGPSYGDRCDYLDHWGRGALVTVSS SEQ ID 16
DIVMTQSPLSLPVTPGEPASISCRSSQSLLEPNGHNYVDWYQQKPGQSPRLLIYLGSNRA
SGVPDRFSGSGGGTDFTLKISRVEAEDVGLYYCMQPLQTPYTFGQGTKLEIK SEQ ID 12
EVQLLESGGGLVQPGGSLRLSCATSGFTFNNYAIHWVRQAPGKGLEWVSAIGGDGHSTYY
VEAVKGRFTISSDSSKNTVYLQVNSLRPEDTALYYCAREGYSSGRCGSFDHWGQGTLVTVSS SEQ ID 17
DIQMTQSPSTLSASVGDRVTITCRASQSISSWLAWYQQKPGKAPKLLINKASSLESGVPS
RFSGSGSGTEFTLTISSLQPDDFATYYCQQYNDYSPAFGQGTKVEIK SEQ ID 13
QLQLQESGPGLVKPSETLSLTCSVSGVSISNFNYYWGWVRQPPGKPLEWIGTIYYNGNTY
YNPSLKSRVTISVDTSKTQLSLKLLSVTAADTAVYYCAWDSGSVERFDHWSQGTLVTVSS SEQ ID 18
QSVLTQPPSTSGTPGQRVTISCSGSSSNIGSKTVNWYKQVPGTAPKLLVFNDNQRPSRVP
DRFSGSKSGTSASLAISGLQSDDEADYYCAAWDDNFNGLLFGGGTKLTVL SEQ ID 14
EVQLVESGGGLVQPGGSLRLSCSTSGFDFSRHWMTWVRQAPGKGLEWVADIKKDGSEENYVD
TVKGRLTISRDNARRSLYLQMNSLRTDDTAVYYCARGPSYGDRSDYLDNWGQGTLVTVSS SEQ ID 19
DIVMTQSPLSLAVTPGEPASISCRSSQWLLESNGHNYLDWYLQKPGQSPQLLIPLGSNRA
SGVPDRFSGSGSGTDFTLTISRVEAEDVGVYYCMQPLKLPYTFGQGTKLEIK SEQ ID 15
EVQLVESGGGLVQPGGSLRLSCSTSGFDFSRHWMTWVRQAPGKGLEWVADIKKDGSEENYVD
TVKGRLTISRDNARRSLYLQMNSLRTDDTAVYYCARGPSYGDRSDYLDNWGQGTLVTVSS SEQ ID 20
DIVMTQSPLSLAVTPGEPASISCRSSQWLLESNGHNYLDWYLQKPGQSPQLLISLGSNRA
SGVPDRFSGSGSGTDFTLTISRVEAEDVGVYYCMQPLKLPYTFGQGTKLEIK SEQ ID 68 (VL is e.g. SEQ ID16)
EVQLVESGGGLVQPGGSLRLSCEASGFTFSRNWMSWVRQIPGKGLEWVADIKADGSEKVYLDS
MKGRLTISRDNARNLLYLQMDSLRVEDSALYHCARGPSYGDRSDYLDHWGRGALVTVSS SEQ ID 69 (VL is e.g. SEQ ID16)
EVQLVESGGGLVQPGGSLRLSCEASGFTFSRNWMSWVRQIPGKGLEWVADIKADGSEKVYLDS
MKGRLTISRDNARNLLYLQMDSLRVEDSALYYCARGPSYGDRCDYLDHWGRGALVTVSS SEQ ID 70 (VL is e.g. SEQ ID16)
EVQLVESGGGLVQPGGSLRLSCEASGFTFSRNWMSWVRQIPGKGLEWVADIKADGSEKVYLDS
MKGRLTISRDNARNLLYLQMDSLRVEDSALYYCARGPSYGDRSDYLDHWGRGALVTVSS O3  MeP-[-2-αManp-(1-2)-αManp-(1-2)-αManp-(1-3)-αManp-(1-3)-αManp-(1-3)-αManp-(1-CP CP  -5)-αKdO-*(2-6)-αGlcN-Biotin

Fig. 3g

HEAVY CHAIN

| antibody name | IGHV | IGHD | IGHJ | Somatic hypermutation counts | Original IGH isotype |
|---|---|---|---|---|---|
| UaLPL03-095 | IGHV3-23*01 | IGHD3-22*01 | IGHJ4*02 | 33 | IGHA2 |
| UaLPL03-208 | IGHV4-39*01 | - | IGHJ4*02 | 18 | IGHA2 |
| UaLPL03-547 | IGHV3-7*03 | IGHD4-17*01 | IGHJ1*01 | 24 | IGHA1 |
| UaLPL03-555 | IGHV3-7*03 | IGHD4-17*01 | IGHJ1*01 | 24 | IGHA1 |
| UaLPL03-601 | IGHV3-7*03 | IGHD2-21*02 | IGHJ4*02 | 26 | IGHA1 |

LIGHT CHAIN

| antibody name | IGLV | IGLJ | Light chain V genes Somatic hypermutation counts |
|---|---|---|---|
| UaLPL03-095 | IGKV1-5*03 | IGKJ1*01 | 7 |
| UaLPL03-208 | IGLV1-44*01 | IGLJ7*01 | 16 |
| UaLPL03-547 | IGKV2-28*01 | IGKJ2*01 | 13 |
| UaLPL03-555 | IGKV2-28*01 | IGKJ2*01 | 12 |
| UaLPL03-601 | IGKV2-28*01 | IGKJ2*01 | 16 |

Fig. 4
A)
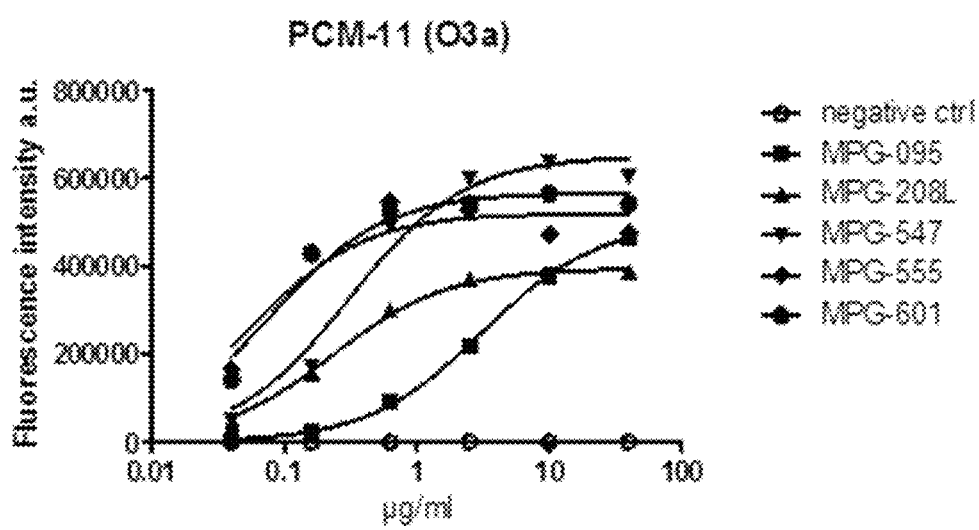
B)
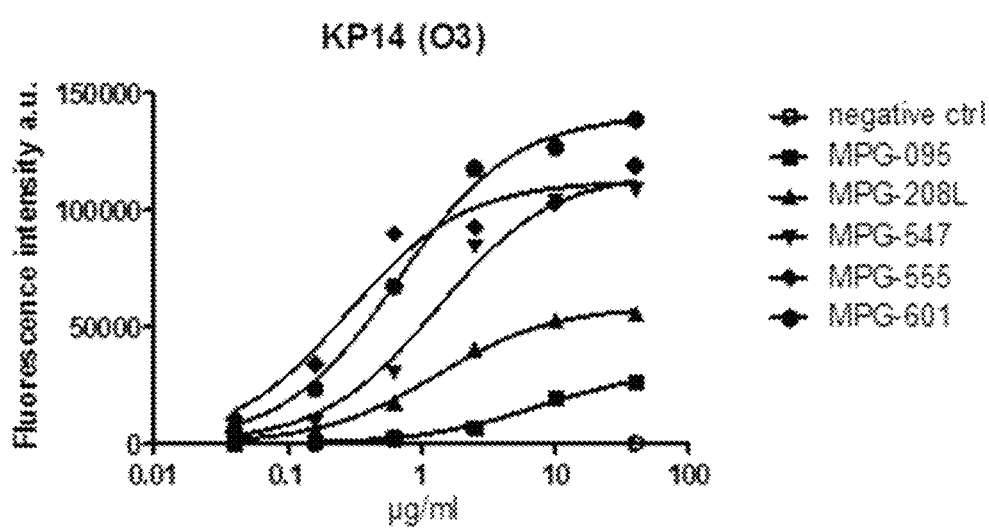

Fig. 6
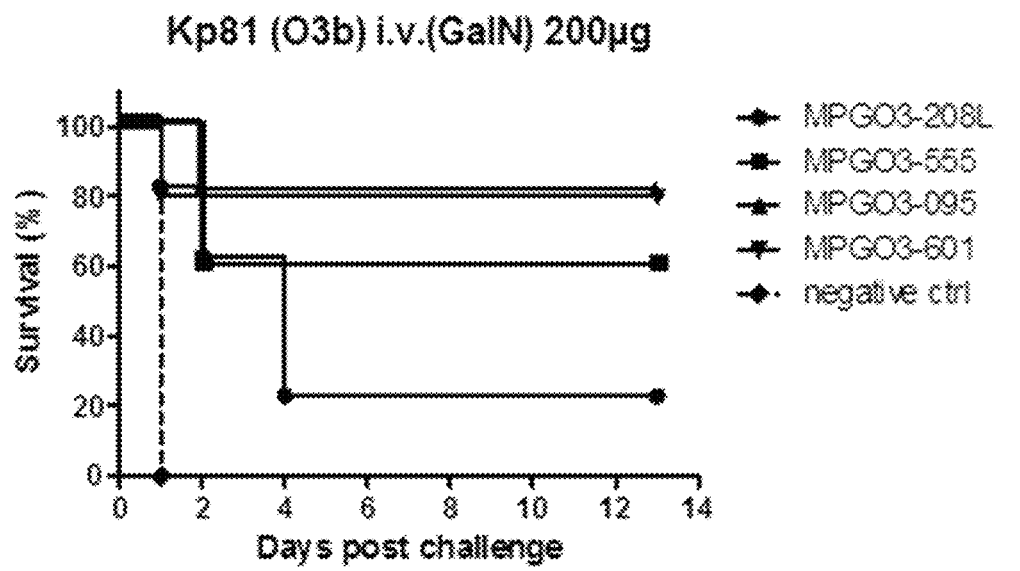
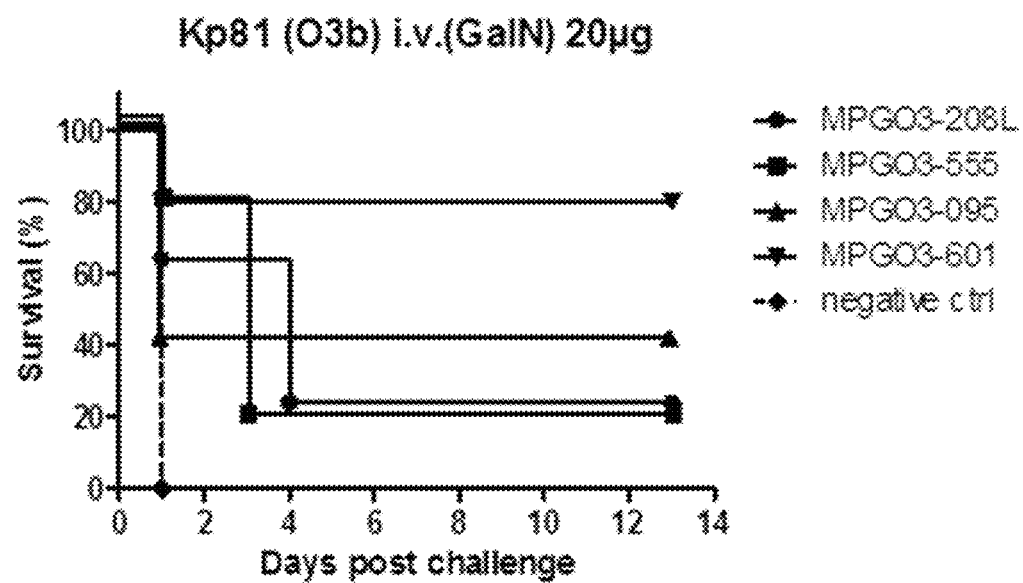

| mAb name | specificity (detected by immunoblot) | | | |
|---|---|---|---|---|
| | O3 | O3a | O3b | O5 |
| MPGO3-009 | + | + | - | - |
| MPGO3-029 | + | + | - | - |
| MPGO3-153 | + | + | + | - |
| MPGO3-171 | + | + | + | - |
| MPGO3-547 | + | + | + | - |
| MPGO3-555 | + | + | + | - |
| MPGO3-601 | + | + | + | - |
| MPGO3-095 | + | + | + | + |
| MPGO3-208L | + | + | + | - |
| MPGO3-461 | + | + | - | - |
| MPGO3-537 | + | + | - | + |
| MPGO3-666 | + | + | + | + |

SEQUENCE LISTING

```
<160> NUMBER OF SEQ ID NOS: 79

<210> SEQ ID NO 1
```

```
<211> LENGTH: 367
<212> TYPE: DNA
<213> ORGANISM: Artificial Sequence
<220> FEATURE:
<223> OTHER INFORMATION: VH

<400> SEQUENCE: 1
gaagtgcagc tggtggagtc tgggggaggc ttggtccagc ctggggggtc cctgagactc      60
tcctgtgaag cctctggctt cacctttagt aggaattgga tgagttgggt ccgccagatt     120
ccagggaagg ggctggagtg ggtggccgac ataaaggcag atggaagtga aaagtctat      180 ctggactcta tgaagggccg attaaccatt tccagagaca cgccaggaa tttattgtat      240 ctgcaaatgg acagcctgag agtcgaggac tcggccctat atcactgtgc gagaggcccc    300
tcttatggtg acaggtgtga ctacttggac cactggggcc ggggagccct ggtcaccgtc     360
tcctcag                                                               367

<210> SEQ ID NO 2
<211> LENGTH: 367
<212> TYPE: DNA
<213> ORGANISM: Artificial Sequence
<220> FEATURE:
<223> OTHER INFORMATION: VH

<400> SEQUENCE: 2
gaggtgcagc tgttggagtc tgggggaggc ttggtgcagc cggggggggtc cctgagactc     60 tcctgtgcaa cctccggatt cacctttaac aactatgcca tccactgggt ccgccaggct    120
ccagggaagg ggctggaatg ggtctcagcc attggtggtg atggtcattc gacatattat    180
gtagaggccg tgaagggccg gttcaccatc tccagtgaca gttccaagaa cacggtatat    240
ctgcaggtga acagcctgag acccgaggac acggccctat attattgtgc gagagagggc    300
tatagtagtg gccggtgcgg gtcttttgac cactggggcc agggaaccct ggtcaccgtc    360
tcctcag                                                               367

<210> SEQ ID NO 3
<211> LENGTH: 361
<212> TYPE: DNA
<213> ORGANISM: Artificial Sequence
<220> FEATURE:
<223> OTHER INFORMATION: VH

<400> SEQUENCE: 3
cagctgcagc tgcaggagtc gggcccagga ctggtgaagc cttcggagac cctgtccctc     60
acctgctctg tctctggtgt ctccatcagc aattttaatt actactgggg ctgggtccgc    120
cagcccccag ggaagccgct ggagtggatt gggactatct attataatgg aaacacctac    180
tacaacccgt ccctcaagag tcgagtcacc atatccgtag acacgtccaa gactcagttg    240
tccctgaagc tgctctctgt gaccgccgca gacacggctg tgtattactg tgcgtgggac    300
tccggttctg tggaaagatt tgaccactgg agccagggaa ccctggtcac cgtctcctca    360
g                                                                    361

<210> SEQ ID NO 4
<211> LENGTH: 367
<212> TYPE: DNA
<213> ORGANISM: Artificial Sequence
<220> FEATURE:
<223> OTHER INFORMATION: VH

<400> SEQUENCE: 4
```

| | |
|---|---:|
| gaagtgcagc tggtggagtc tgggggaggc ttggtccagc cggggggtc cctgagactc | 60 |
| tcctgttcaa cgtctggatt cgactttagt aggcattgga tgacctgggt ccgacaggct | 120 |
| ccagggaagg ggctggagtg ggtggccgac ataaagaaag atggaagtga ggagaactat | 180 |
| gtggacactg tgaagggccg actcaccatc tccagagaca cgccaggag gtcactctat | 240 |
| ctgcaaatga acagcctgag aaccgacgac acggccgtgt attattgtgc gagaggaccc | 300 |
| tcgtatggtg accggagtga ctacctggac aactggggcc aggggaccct ggtcaccgtc | 360 |
| tcctcag | 367 |

<210> SEQ ID NO 5
<211> LENGTH: 367
<212> TYPE: DNA
<213> ORGANISM: Artificial Sequence
<220> FEATURE:
<223> OTHER INFORMATION: VH

<400> SEQUENCE: 5

| | |
|---|---:|
| gaagtgcagc tggtggagtc tgggggaggc ttggtccagc cggggggtc cctgagactc | 60 |
| tcctgttcaa cgtctggatt cgactttagt aggcattgga tgacctgggt ccgacaggct | 120 |
| ccagggaagg ggctggagtg ggtggccgac ataaagaaag atggaagtga ggagaactat | 180 |
| gtggacactg tgaagggccg actcaccatc tccagagaca cgccaggag gtcactctat | 240 |
| ctgcaaatga acagcctgag aaccgacgac acggccgtgt attattgtgc gagaggaccc | 300 |
| tcgtatggtg accggagtga ctacctggac aactggggcc aggggaccct ggtcaccgtc | 360 |
| tcctcag | 367 |

<210> SEQ ID NO 6
<211> LENGTH: 337
<212> TYPE: DNA
<213> ORGANISM: Artificial Sequence
<220> FEATURE:
<223> OTHER INFORMATION: VL

<400> SEQUENCE: 6

| | |
|---|---:|
| gatattgtga tgactcagtc tccactctcc ctgcccgtca ccccaggaga gccggcctcc | 60 |
| atctcctgca ggtctagtca gagcctcctg gagcctaatg acacaacta tgtggattgg | 120 |
| taccagcaaa agccagggca gtctccacgg ctcctgatct atttgggttc taaccgggcc | 180 |
| tccggggtcc ctgacaggtt cagtggcagt ggaggaggca cagactttac actgaaaatc | 240 |
| agcagagtgg aggctgagga tgttgggctt tattactgca tgcaacctct gcaaactccg | 300 |
| tacactttg gccaggggac caagctggag atcaaac | 337 |

<210> SEQ ID NO 7
<211> LENGTH: 322
<212> TYPE: DNA
<213> ORGANISM: Artificial Sequence
<220> FEATURE:
<223> OTHER INFORMATION: VL

<400> SEQUENCE: 7

| | |
|---|---:|
| gacatccaga tgacccagtc tccttccacc ctgtctgcat ctgttggaga cagagtcacc | 60 |
| atcacttgcc gggccagtca gagtatcagt agctggttgg cctggtatca gcagaaacca | 120 |
| ggaaaagccc ctaagctcct gatcaataag gcgtctagtt tggaaagtgg ggtcccatca | 180 |
| agattcagcg gcagcggatc tgggacagaa ttcactctca ccatcagcag cctgcagcct | 240 | gatgattttg caacttatta ctgccaacag tataatgatt attctcccgc attcggccaa    300 gggaccaagg tggagatcaa ac    322

<210> SEQ ID NO 8
<211> LENGTH: 330
<212> TYPE: DNA
<213> ORGANISM: Artificial Sequence
<220> FEATURE:
<223> OTHER INFORMATION: VL

<400> SEQUENCE: 8
cagtctgtgc tgactcagcc accctcaacg tctgggaccc ccgggcagag ggtcaccatc    60
tcttgttctg gaagcagctc caacatcgga agtaaaactg tcaactggta caagcaagtc    120
ccaggaacgg cccccaaact cctcgtcttt aatgataatc aacgccctc cagggtccct    180 gaccgattct ctgggtccaa gtctggcacg tcagcctccc tggccatcag tgggctccag    240
tctgacgatg aggctgatta ttactgtgca gcgtgggatg acaacttcaa tggcctgcta    300
ttcggcggag ggaccaagct gaccgtccta    330

<210> SEQ ID NO 9
<211> LENGTH: 337
<212> TYPE: DNA
<213> ORGANISM: Artificial Sequence
<220> FEATURE:
<223> OTHER INFORMATION: VL

<400> SEQUENCE: 9
gatattgtga tgactcagtc tcctctctcc ctggccgtca cccctggaga gccggcctcc    60
atctcctgca ggtctagtca gtggctcctg gagagtaatg gacacaacta tttggattgg    120
tacctgcaga agccagggca gtctccacaa ctcctgatcc cttgggttc taatcgggcc    180 tccggggtcc ctgacaggtt cagtggcagt gggtcaggca cagatttac actgacaatc    240 agcagagtgg aggctgagga tgttgggggtt tattattgca tgcaacctct aaaacttccg    300 tacactttg gccaggggac caagctggag atcaaac    337

<210> SEQ ID NO 10
<211> LENGTH: 337
<212> TYPE: DNA
<213> ORGANISM: Artificial Sequence
<220> FEATURE:
<223> OTHER INFORMATION: VL

<400> SEQUENCE: 10
gatattgtga tgactcagtc tcctctctcc ctggccgtca cccctggaga gccggcctcc    60
atctcctgca ggtctagtca gtggctcctg gagagtaatg gacacaacta tttggattgg    120
tacctgcaga agccagggca gtctccacaa ctcctgatct cttgggttc taatcgggcc    180 tccggggtcc ctgacaggtt cagtggcagt gggtcaggca cagatttac actgacaatc    240 agcagagtgg aggctgagga tgttgggggtt tattattgca tgcaacctct aaaacttccg    300 tacactttg gccaggggac caagctggag atcaaac    337

<210> SEQ ID NO 11
<211> LENGTH: 122
<212> TYPE: PRT
<213> ORGANISM: Artificial Sequence
<220> FEATURE:
<223> OTHER INFORMATION: VH

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Arg Asn
            20                  25                  30

Trp Met Ser Trp Val Arg Gln Ile Pro Gly Lys Gly Leu Glu Trp Val
        35                  40                  45

Ala Asp Ile Lys Ala Asp Gly Ser Glu Lys Val Tyr Leu Asp Ser Met
    50                  55                  60

Lys Gly Arg Leu Thr Ile Ser Arg Asp Asn Ala Arg Asn Leu Leu Tyr
65                  70                  75                  80

Leu Gln Met Asp Ser Leu Arg Val Glu Asp Ser Ala Leu Tyr His Cys
                85                  90                  95

Ala Arg Gly Pro Ser Tyr Gly Asp Arg Cys Asp Tyr Leu Asp His Trp
            100                 105                 110

Gly Arg Gly Ala Leu Val Thr Val Ser Ser
        115                 120

<210> SEQ ID NO 12
<211> LENGTH: 122
<212> TYPE: PRT
<213> ORGANISM: Artificial Sequence
<220> FEATURE:
<223> OTHER INFORMATION: VH

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Asn Asn Tyr
            20                  25                  30

Ala Ile His Trp Val Arg Gln Ala Pro Gly Lys Gly Leu Glu Trp Val
        35                  40                  45

Ser Ala Ile Gly Gly Asp Gly His Ser Thr Tyr Tyr Val Glu Ala Val
    50                  55                  60

Lys Gly Arg Phe Thr Ile Ser Ser Asp Ser Ser Lys Asn Thr Val Tyr
65                  70                  75                  80

Leu Gln Val Asn Ser Leu Arg Pro Glu Asp Thr Ala Leu Tyr Tyr Cys
                85                  90                  95

Ala Arg Glu Gly Tyr Ser Ser Gly Arg Cys Gly Ser Phe Asp His Trp
            100                 105                 110

Gly Gln Gly Thr Leu Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: VH

<400> SEQUENCE: 13

Gln Leu Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Ser Asn Phe
            20                  25                  30

Asn Tyr Tyr Trp Gly Trp Val Arg Gln Pro Pro Gly Lys Pro Leu Glu
        35                  40                  45

Trp Ile Gly Thr Ile Tyr Tyr Asn Gly Asn Thr Tyr Tyr Asn Pro Ser

```
                        50                   55                       60
Leu Lys Ser Arg Val Thr Ile Ser Val Asp Thr Ser Lys Thr Gln Leu
 65                  70                  75                      80

Ser Leu Lys Leu Leu Ser Val Thr Ala Ala Asp Thr Ala Val Tyr Tyr
                     85                  90                  95

Cys Ala Trp Asp Ser Gly Ser Val Glu Arg Phe Asp His Trp Ser Gln
                100                 105                 110

Gly Thr Leu Val Thr Val Ser Ser
            115                 120
```

<210> SEQ ID NO 14
<211> LENGTH: 122
<212> TYPE: PRT
<213> ORGANISM: Artificial Sequence
<220> FEATURE:
<223> OTHER INFORMATION: VH

<400> SEQUENCE: 14

```
Glu Val Gln Leu Val Glu Ser Gly Gly Gly Leu Val Gln Pro Gly Gly
 1               5                  10                  15

Ser Leu Arg Leu Ser Cys Ser Thr Ser Gly Phe Asp Phe Ser Arg His
             20                  25                  30

Trp Met Thr Trp Val Arg Gln Ala Pro Gly Lys Gly Leu Glu Trp Val
         35                  40                  45

Ala Asp Ile Lys Lys Asp Gly Ser Glu Glu Asn Tyr Val Asp Thr Val
     50                  55                  60

Lys Gly Arg Leu Thr Ile Ser Arg Asp Asn Ala Arg Arg Ser Leu Tyr
 65                  70                  75                      80

Leu Gln Met Asn Ser Leu Arg Thr Asp Thr Ala Val Tyr Tyr Cys
                     85                  90                  95

Ala Arg Gly Pro Ser Tyr Gly Asp Arg Ser Asp Tyr Leu Asp Asn Trp
                100                 105                 110

Gly Gln Gly Thr Leu Val Thr Val Ser Ser
            115                 120
```

<210> SEQ ID NO 15
<211> LENGTH: 122
<212> TYPE: PRT
<213> ORGANISM: Artificial Sequence
<220> FEATURE:
<223> OTHER INFORMATION: VH

<400> SEQUENCE: 15

```
Glu Val Gln Leu Val Glu Ser Gly Gly Gly Leu Val Gln Pro Gly Gly
 1               5                  10                  15

Ser Leu Arg Leu Ser Cys Ser Thr Ser Gly Phe Asp Phe Ser Arg His
             20                  25                  30

Trp Met Thr Trp Val Arg Gln Ala Pro Gly Lys Gly Leu Glu Trp Val
         35                  40                  45

Ala Asp Ile Lys Lys Asp Gly Ser Glu Glu Asn Tyr Val Asp Thr Val
     50                  55                  60

Lys Gly Arg Leu Thr Ile Ser Arg Asp Asn Ala Arg Arg Ser Leu Tyr
 65                  70                  75                      80

Leu Gln Met Asn Ser Leu Arg Thr Asp Thr Ala Val Tyr Tyr Cys
                     85                  90                  95

Ala Arg Gly Pro Ser Tyr Gly Asp Arg Ser Asp Tyr Leu Asp Asn Trp
                100                 105                 110
```

```
Gly Gln Gly Thr Leu Val Thr Val Ser Ser
        115                 120

<210> SEQ ID NO 16
<211> LENGTH: 112
<212> TYPE: PRT
<213> ORGANISM: Artificial Sequence
<220> FEATURE:
<223> OTHER INFORMATION: VL

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Glu Pro
            20                  25                  30

Asn Gly His Asn Tyr Val Asp Trp Tyr Gln Gln Lys Pro Gly Gln Ser
        35                  40                  45

Pro Arg Leu Leu Ile Tyr Leu Gly Ser Asn Arg Ala Ser Gly Val Pro
    50                  55                  60

Asp Arg Phe Ser Gly Ser Gly Gly Thr Asp Phe Thr Leu Lys Ile
65                  70                  75                  80

Ser Arg Val Glu Ala Glu Asp Val Gly Leu Tyr Tyr Cys Met Gln Pro
                85                  90                  95

Leu Gln Thr Pro Tyr Thr Phe Gly Gln Gly Thr Lys Leu Glu Ile Lys
            100                 105                 110

<210> SEQ ID NO 17
<211> LENGTH: 107
<212> TYPE: PRT
<213> ORGANISM: Artificial Sequence
<220> FEATURE:
<223> OTHER INFORMATION: VL

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Asn Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asp Tyr Ser Pro
                85                  90                  95

Ala Phe Gly Gln Gly Thr Lys Val Glu Ile Lys
            100                 105

<210> SEQ ID NO 18
<211> LENGTH: 110
<212> TYPE: PRT
<213> ORGANISM: Artificial Sequence
<220> FEATURE:
<223> OTHER INFORMATION: VL

<400> SEQUENCE: 18

Gln Ser Val Leu Thr Gln Pro Pro Ser Thr Gly Thr Pro Gly Gln
1               5                   10                  15

Arg Val Thr Ile Ser Cys Ser Gly Ser Ser Ser Asn Ile Gly Ser Lys
```

```
                    20                  25                  30

Thr Val Asn Trp Tyr Lys Gln Val Pro Gly Thr Ala Pro Lys Leu Leu
            35                  40                  45

Val Phe Asn Asp Asn Gln Arg Pro Ser Arg Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Asp Asp Glu Ala Asp Tyr Tyr Cys Ala Ala Trp Asp Asp Asn Phe
                    85                  90                  95

Asn Gly Leu Leu Phe Gly Gly Gly Thr Lys Leu Thr Val Leu
                100                 105                 110

<210> SEQ ID NO 19
<211> LENGTH: 112
<212> TYPE: PRT
<213> ORGANISM: Artificial Sequence
<220> FEATURE:
<223> OTHER INFORMATION: VL

<400> SEQUENCE: 19

Asp Ile Val Met Thr Gln Ser Pro Leu Ser Leu Ala Val Thr Pro Gly
 1               5                  10                  15

Glu Pro Ala Ser Ile Ser Cys Arg Ser Ser Gln Trp Leu Leu Glu Ser
                20                  25                  30

Asn Gly His Asn Tyr Leu Asp Trp Tyr Leu Gln Lys Pro Gly Gln Ser
            35                  40                  45

Pro Gln Leu Leu Ile Pro Leu Gly Ser Asn Arg Ala Ser Gly Val Pro
 50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Val Gly Val Tyr Tyr Cys Met Gln Pro
                85                  90                  95

Leu Lys Leu Pro Tyr Thr Phe Gly Gln Gly Thr Lys Leu Glu Ile Lys
                100                 105                 110

<210> SEQ ID NO 20
<211> LENGTH: 112
<212> TYPE: PRT
<213> ORGANISM: Artificial Sequence
<220> FEATURE:
<223> OTHER INFORMATION: VL

<400> SEQUENCE: 20

Asp Ile Val Met Thr Gln Ser Pro Leu Ser Leu Ala Val Thr Pro Gly
 1               5                  10                  15

Glu Pro Ala Ser Ile Ser Cys Arg Ser Ser Gln Trp Leu Leu Glu Ser
                20                  25                  30

Asn Gly His Asn Tyr Leu Asp Trp Tyr Leu Gln Lys Pro Gly Gln Ser
            35                  40                  45

Pro Gln Leu Leu Ile Ser Leu Gly Ser Asn Arg Ala Ser Gly Val Pro
 50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Val Gly Val Tyr Tyr Cys Met Gln Pro
                85                  90                  95

Leu Lys Leu Pro Tyr Thr Phe Gly Gln Gly Thr Lys Leu Glu Ile Lys
                100                 105                 110
```

```
<210> SEQ ID NO 21
<211> LENGTH: 5
<212> TYPE: PRT
<213> ORGANISM: Artificial Sequence
<220> FEATURE:
<223> OTHER INFORMATION: CDR

<400> SEQUENCE: 21

Arg Asn Trp Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: CDR

<400> SEQUENCE: 22

Asp Ile Lys Ala Asp Gly Ser Glu Lys Val Tyr Leu Asp Ser Met Lys
1               5                   10                  15

Gly

<210> SEQ ID NO 23
<211> LENGTH: 13
<212> TYPE: PRT
<213> ORGANISM: Artificial Sequence
<220> FEATURE:
<223> OTHER INFORMATION: CDR

<400> SEQUENCE: 23

Gly Pro Ser Tyr Gly Asp Arg Cys Asp Tyr Leu Asp His
1               5                   10

<210> SEQ ID NO 24
<211> LENGTH: 5
<212> TYPE: PRT
<213> ORGANISM: Artificial Sequence
<220> FEATURE:
<223> OTHER INFORMATION: CDR

<400> SEQUENCE: 24

Asn Tyr Ala Ile His
1               5

<210> SEQ ID NO 25
<211> LENGTH: 17
<212> TYPE: PRT
<213> ORGANISM: Artificial Sequence
<220> FEATURE:
<223> OTHER INFORMATION: CDR

<400> SEQUENCE: 25

Ala Ile Gly Gly Asp Gly His Ser Thr Tyr Tyr Val Glu Ala Val Lys
1               5                   10                  15

Gly

<210> SEQ ID NO 26
<211> LENGTH: 13
<212> TYPE: PRT
<213> ORGANISM: Artificial Sequence
<220> FEATURE:
<223> OTHER INFORMATION: CDR

<400> SEQUENCE: 26
```

Glu Gly Tyr Ser Ser Gly Arg Cys Gly Ser Phe Asp His
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CDR

<400> SEQUENCE: 27

Asn Phe Asn Tyr Tyr Trp Gly
1               5

<210> SEQ ID NO 28
<211> LENGTH: 16
<212> TYPE: PRT
<213> ORGANISM: Artificial Sequence
<220> FEATURE:
<223> OTHER INFORMATION: CDR

<400> SEQUENCE: 28

Thr Ile Tyr Tyr Asn Gly Asn Thr Tyr Tyr Asn Pro Ser Leu Lys Ser
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: CDR

<400> SEQUENCE: 29

Asp Ser Gly Ser Val Glu Arg Phe Asp His
1               5                   10

<210> SEQ ID NO 30
<211> LENGTH: 5
<212> TYPE: PRT
<213> ORGANISM: Artificial Sequence
<220> FEATURE:
<223> OTHER INFORMATION: CDR

<400> SEQUENCE: 30

Arg His Trp Met Thr
1               5

<210> SEQ ID NO 31
<211> LENGTH: 17
<212> TYPE: PRT
<213> ORGANISM: Artificial Sequence
<220> FEATURE:
<223> OTHER INFORMATION: CDR

<400> SEQUENCE: 31

Asp Ile Lys Lys Asp Gly Ser Glu Glu Asn Tyr Val Asp Thr Val Lys
1               5                   10                  15

Gly

<210> SEQ ID NO 32
<211> LENGTH: 13
<212> TYPE: PRT
<213> ORGANISM: Artificial Sequence
<220> FEATURE:
<223> OTHER INFORMATION: CDR

<400> SEQUENCE: 32

```
Gly Pro Ser Tyr Gly Asp Arg Ser Asp Tyr Leu Asp Asn
1               5                   10
```

<210> SEQ ID NO 33
<211> LENGTH: 16
<212> TYPE: PRT
<213> ORGANISM: Artificial Sequence
<220> FEATURE:
<223> OTHER INFORMATION: CDR

<400> SEQUENCE: 33

```
Arg Ser Ser Gln Ser Leu Leu Glu Pro Asn Gly His Asn Tyr Val Asp
1               5                   10                  15
```

<210> SEQ ID NO 34
<211> LENGTH: 7
<212> TYPE: PRT
<213> ORGANISM: Artificial Sequence
<220> FEATURE:
<223> OTHER INFORMATION: CDR

<400> SEQUENCE: 34

```
Leu Gly Ser Asn Arg Ala Ser
1               5
```

<210> SEQ ID NO 35
<211> LENGTH: 9
<212> TYPE: PRT
<213> ORGANISM: Artificial Sequence
<220> FEATURE:
<223> OTHER INFORMATION: MQPLQTPYT

<400> SEQUENCE: 35

```
Met Gln Pro Leu Gln Thr Pro Tyr Thr
1               5
```

<210> SEQ ID NO 36
<211> LENGTH: 11
<212> TYPE: PRT
<213> ORGANISM: Artificial Sequence
<220> FEATURE:
<223> OTHER INFORMATION: CDR

<400> SEQUENCE: 36

```
Arg Ala Ser Gln Ser Ile Ser Ser Trp Leu Ala
1               5                   10
```

<210> SEQ ID NO 37
<211> LENGTH: 7
<212> TYPE: PRT
<213> ORGANISM: Artificial Sequence
<220> FEATURE:
<223> OTHER INFORMATION: CDR

<400> SEQUENCE: 37

```
Lys Ala Ser Ser Leu Glu Ser
1               5
```

<210> SEQ ID NO 38
<211> LENGTH: 9
<212> TYPE: PRT
<213> ORGANISM: Artificial Sequence
<220> FEATURE:
<223> OTHER INFORMATION: CDR

<400> SEQUENCE: 38

Gln Gln Tyr Asn Asp Tyr Ser Pro Ala
1               5

<210> SEQ ID NO 39
<211> LENGTH: 13
<212> TYPE: PRT
<213> ORGANISM: Artificial Sequence
<220> FEATURE:
<223> OTHER INFORMATION: CDR

<400> SEQUENCE: 39

Ser Gly Ser Ser Ser Asn Ile Gly Ser Lys Thr Val Asn
1               5                   10

<210> SEQ ID NO 40
<211> LENGTH: 7
<212> TYPE: PRT
<213> ORGANISM: Artificial Sequence
<220> FEATURE:
<223> OTHER INFORMATION: CDR

<400> SEQUENCE: 40

Asn Asp Asn Gln Arg Pro Ser
1               5

<210> SEQ ID NO 41
<211> LENGTH: 11
<212> TYPE: PRT
<213> ORGANISM: Artificial Sequence
<220> FEATURE:
<223> OTHER INFORMATION: CDR

<400> SEQUENCE: 41

Ala Ala Trp Asp Asp Asn Phe Asn Gly Leu Leu
1               5                   10

<210> SEQ ID NO 42
<211> LENGTH: 16
<212> TYPE: PRT
<213> ORGANISM: Artificial Sequence
<220> FEATURE:
<223> OTHER INFORMATION: CDR

<400> SEQUENCE: 42

Arg Ser Ser Gln Trp Leu Leu Glu Ser Asn Gly His Asn Tyr Leu Asp
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: CDR

<400> SEQUENCE: 43

Met Gln Pro Leu Lys Leu Pro Tyr Thr
1               5

<210> SEQ ID NO 44
<211> LENGTH: 8
<212> TYPE: PRT
<213> ORGANISM: Artificial Sequence
<220> FEATURE:
<223> OTHER INFORMATION: CDR

<400> SEQUENCE: 44

Gly Phe Thr Phe Ser Arg Asn Trp

<210> SEQ ID NO 45
<211> LENGTH: 8
<212> TYPE: PRT
<213> ORGANISM: Artificial Sequence
<220> FEATURE:
<223> OTHER INFORMATION: CDR

<400> SEQUENCE: 45

Ile Lys Ala Asp Gly Ser Glu Lys
1               5

<210> SEQ ID NO 46
<211> LENGTH: 15
<212> TYPE: PRT
<213> ORGANISM: Artificial Sequence
<220> FEATURE:
<223> OTHER INFORMATION: CDR

<400> SEQUENCE: 46

Ala Arg Gly Pro Ser Tyr Gly Asp Arg Cys Asp Tyr Leu Asp His
1               5                   10                  15

<210> SEQ ID NO 47
<211> LENGTH: 8
<212> TYPE: PRT
<213> ORGANISM: Artificial Sequence
<220> FEATURE:
<223> OTHER INFORMATION: CDR

<400> SEQUENCE: 47

Gly Phe Thr Phe Asn Asn Tyr Ala
1               5

<210> SEQ ID NO 48
<211> LENGTH: 8
<212> TYPE: PRT
<213> ORGANISM: Artificial Sequence
<220> FEATURE:
<223> OTHER INFORMATION: CDR

<400> SEQUENCE: 48

Ile Gly Gly Asp Gly His Ser Thr
1               5

<210> SEQ ID NO 49
<211> LENGTH: 15
<212> TYPE: PRT
<213> ORGANISM: Artificial Sequence
<220> FEATURE:
<223> OTHER INFORMATION: CDR

<400> SEQUENCE: 49

Ala Arg Glu Gly Tyr Ser Ser Gly Arg Cys Gly Ser Phe Asp His
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: CDR

<400> SEQUENCE: 50

Gly Val Ser Ile Ser Asn Phe Asn Tyr Tyr
1               5                   10

<210> SEQ ID NO 51
<211> LENGTH: 7
<212> TYPE: PRT
<213> ORGANISM: Artificial Sequence
<220> FEATURE:
<223> OTHER INFORMATION: CDR

<400> SEQUENCE: 51

Ile Tyr Tyr Asn Gly Asn Thr
1               5

<210> SEQ ID NO 52
<211> LENGTH: 12
<212> TYPE: PRT
<213> ORGANISM: Artificial Sequence
<220> FEATURE:
<223> OTHER INFORMATION: CDR

<400> SEQUENCE: 52

Ala Trp Asp Ser Gly Ser Val Glu Arg Phe Asp His
1               5                   10

<210> SEQ ID NO 53
<211> LENGTH: 8
<212> TYPE: PRT
<213> ORGANISM: Artificial Sequence
<220> FEATURE:
<223> OTHER INFORMATION: CDR

<400> SEQUENCE: 53

Gly Phe Asp Phe Ser Arg His Trp
1               5

<210> SEQ ID NO 54
<211> LENGTH: 8
<212> TYPE: PRT
<213> ORGANISM: Artificial Sequence
<220> FEATURE:
<223> OTHER INFORMATION: CDR

<400> SEQUENCE: 54

Ile Lys Lys Asp Gly Ser Glu Glu
1               5

<210> SEQ ID NO 55
<211> LENGTH: 15
<212> TYPE: PRT
<213> ORGANISM: Artificial Sequence
<220> FEATURE:
<223> OTHER INFORMATION: CDR

<400> SEQUENCE: 55

Ala Arg Gly Pro Ser Tyr Gly Asp Arg Ser Asp Tyr Leu Asp Asn
1               5                   10                  15

<210> SEQ ID NO 56
<211> LENGTH: 11
<212> TYPE: PRT
<213> ORGANISM: Artificial Sequence
<220> FEATURE:
<223> OTHER INFORMATION: CDR

<400> SEQUENCE: 56

Gln Ser Leu Leu Glu Pro Asn Gly His Asn Tyr
1               5                   10

```
<210> SEQ ID NO 57
<211> LENGTH: 3
<212> TYPE: PRT
<213> ORGANISM: Artificial Sequence
<220> FEATURE:
<223> OTHER INFORMATION: CDR

<400> SEQUENCE: 57

Leu Gly Ser
1

<210> SEQ ID NO 58
<211> LENGTH: 9
<212> TYPE: PRT
<213> ORGANISM: Artificial Sequence
<220> FEATURE:
<223> OTHER INFORMATION: CDR

<400> SEQUENCE: 58

Met Gln Pro Leu Gln Thr Pro Tyr Thr
1               5

<210> SEQ ID NO 59
<211> LENGTH: 6
<212> TYPE: PRT
<213> ORGANISM: Artificial Sequence
<220> FEATURE:
<223> OTHER INFORMATION: CDR

<400> SEQUENCE: 59

Gln Ser Ile Ser Ser Trp
1               5

<210> SEQ ID NO 60
<211> LENGTH: 3
<212> TYPE: PRT
<213> ORGANISM: Artificial Sequence
<220> FEATURE:
<223> OTHER INFORMATION: CDR

<400> SEQUENCE: 60

Lys Ala Ser
1

<210> SEQ ID NO 61
<211> LENGTH: 9
<212> TYPE: PRT
<213> ORGANISM: Artificial Sequence
<220> FEATURE:
<223> OTHER INFORMATION: CDR

<400> SEQUENCE: 61

Gln Gln Tyr Asn Asp Tyr Ser Pro Ala
1               5

<210> SEQ ID NO 62
<211> LENGTH: 8
<212> TYPE: PRT
<213> ORGANISM: Artificial Sequence
<220> FEATURE:
<223> OTHER INFORMATION: CDR

<400> SEQUENCE: 62

Ser Ser Asn Ile Gly Ser Lys Thr
1               5
```

```
<210> SEQ ID NO 63
<211> LENGTH: 3
<212> TYPE: PRT
<213> ORGANISM: Artificial Sequence
<220> FEATURE:
<223> OTHER INFORMATION: CDR

<400> SEQUENCE: 63

Asn Asp Asn
1

<210> SEQ ID NO 64
<211> LENGTH: 11
<212> TYPE: PRT
<213> ORGANISM: Artificial Sequence
<220> FEATURE:
<223> OTHER INFORMATION: CDR

<400> SEQUENCE: 64

Ala Ala Trp Asp Asp Asn Phe Asn Gly Leu Leu
1               5                   10

<210> SEQ ID NO 65
<211> LENGTH: 11
<212> TYPE: PRT
<213> ORGANISM: Artificial Sequence
<220> FEATURE:
<223> OTHER INFORMATION: CDR

<400> SEQUENCE: 65

Gln Trp Leu Leu Glu Ser Asn Gly His Asn Tyr
1               5                   10

<210> SEQ ID NO 66
<211> LENGTH: 9
<212> TYPE: PRT
<213> ORGANISM: Artificial Sequence
<220> FEATURE:
<223> OTHER INFORMATION: CDR

<400> SEQUENCE: 66

Met Gln Pro Leu Lys Leu Pro Tyr Thr
1               5

<210> SEQ ID NO 67
<211> LENGTH: 15
<212> TYPE: PRT
<213> ORGANISM: Artificial Sequence
<220> FEATURE:
<223> OTHER INFORMATION: VH CDR3

<400> SEQUENCE: 67

Ala Arg Gly Pro Ser Tyr Gly Asp Arg Ser Asp Tyr Leu Asp His
1               5                   10                  15

<210> SEQ ID NO 68
<211> LENGTH: 122
<212> TYPE: PRT
<213> ORGANISM: Artificial Sequence
<220> FEATURE:
<223> OTHER INFORMATION: VH

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Arg Asn
            20                  25                  30
```

```
Trp Met Ser Trp Val Arg Gln Ile Pro Gly Lys Gly Leu Glu Trp Val
            35                  40                  45

Ala Asp Ile Lys Ala Asp Gly Ser Glu Lys Val Tyr Leu Asp Ser Met
 50                  55                  60

Lys Gly Arg Leu Thr Ile Ser Arg Asp Asn Ala Arg Asn Leu Leu Tyr
 65                  70                  75                  80

Leu Gln Met Asp Ser Leu Arg Val Glu Asp Ser Ala Leu Tyr His Cys
             85                  90                  95

Ala Arg Gly Pro Ser Tyr Gly Asp Arg Ser Asp Tyr Leu Asp His Trp
             100                 105                 110

Gly Arg Gly Ala Leu Val Thr Val Ser Ser
            115                 120
```

<210> SEQ ID NO 69
<211> LENGTH: 122
<212> TYPE: PRT
<213> ORGANISM: Artificial Sequence
<220> FEATURE:
<223> OTHER INFORMATION: VH

<400> SEQUENCE: 69

```
Glu Val Gln Leu Val Glu Ser Gly Gly Gly Leu Val Gln Pro Gly Gly
 1               5                   10                  15

Ser Leu Arg Leu Ser Cys Glu Ala Ser Gly Phe Thr Phe Ser Arg Asn
             20                  25                  30

Trp Met Ser Trp Val Arg Gln Ile Pro Gly Lys Gly Leu Glu Trp Val
            35                  40                  45

Ala Asp Ile Lys Ala Asp Gly Ser Glu Lys Val Tyr Leu Asp Ser Met
 50                  55                  60

Lys Gly Arg Leu Thr Ile Ser Arg Asp Asn Ala Arg Asn Leu Leu Tyr
 65                  70                  75                  80

Leu Gln Met Asp Ser Leu Arg Val Glu Asp Ser Ala Leu Tyr Tyr Cys
             85                  90                  95

Ala Arg Gly Pro Ser Tyr Gly Asp Arg Cys Asp Tyr Leu Asp His Trp
             100                 105                 110

Gly Arg Gly Ala Leu Val Thr Val Ser Ser
            115                 120
```

<210> SEQ ID NO 70
<211> LENGTH: 122
<212> TYPE: PRT
<213> ORGANISM: Artificial Sequence
<220> FEATURE:
<223> OTHER INFORMATION: VH

<400> SEQUENCE: 70

```
Glu Val Gln Leu Val Glu Ser Gly Gly Gly Leu Val Gln Pro Gly Gly
 1               5                   10                  15

Ser Leu Arg Leu Ser Cys Glu Ala Ser Gly Phe Thr Phe Ser Arg Asn
             20                  25                  30

Trp Met Ser Trp Val Arg Gln Ile Pro Gly Lys Gly Leu Glu Trp Val
            35                  40                  45

Ala Asp Ile Lys Ala Asp Gly Ser Glu Lys Val Tyr Leu Asp Ser Met
 50                  55                  60

Lys Gly Arg Leu Thr Ile Ser Arg Asp Asn Ala Arg Asn Leu Leu Tyr
 65                  70                  75                  80

Leu Gln Met Asp Ser Leu Arg Val Glu Asp Ser Ala Leu Tyr Tyr Cys
```

```
            85                  90                  95
Ala Arg Gly Pro Ser Tyr Gly Asp Arg Ser Asp Tyr Leu Asp His Trp
            100                 105                 110
Gly Arg Gly Ala Leu Val Thr Val Ser Ser
            115                 120
```

<210> SEQ ID NO 71
<211> LENGTH: 366
<212> TYPE: DNA
<213> ORGANISM: Artificial Sequence
<220> FEATURE:
<223> OTHER INFORMATION: VH

<400> SEQUENCE: 71

```
gaggtgcagc tggtggaatc tggcggagga ctggtgcagc ctggcggctc tctgagactg    60
tcttgcgagg cctccggctt caccttctcc cggaactgga tgtcctgggt gcgacagatc   120
cctggcaagg cctggaatg gtggccgac atcaaggccg acggctccga aaggtgtac      180 ctggactcta tgaagggccg gctgaccatc tcccgggaca cgccagaaa cctgctgtac    240 ctgcagatgg actccctgcg ggtggaagat tccgccctgt accactgtgc cagaggcccc   300
tcttacggcg acagatccga ctacctggac cattggggca gaggcgccct cgtgacagtg   360
tcctct                                                              366
```

<210> SEQ ID NO 72
<211> LENGTH: 366
<212> TYPE: DNA
<213> ORGANISM: Artificial Sequence
<220> FEATURE:
<223> OTHER INFORMATION: VH

<400> SEQUENCE: 72

```
gaggtgcagc tggtggaatc tggcggagga ctggtgcagc ctggcggctc tctgagactg    60
tcttgcgagg cctccggctt caccttctcc cggaactgga tgtcctgggt gcgacagatc   120
cctggcaagg cctggaatg gtggccgac atcaaggccg acggctccga aaggtgtac      180 ctggactcta tgaagggccg gctgaccatc tcccgggaca cgccagaaa cctgctgtac    240 ctgcagatgg actccctgcg ggtggaagat tccgccctgt actactgtgc cagaggcccc   300
tcttacggcg acagatgcga ctacctggac cattggggca gaggcgccct cgtgacagtg   360
tcctct                                                              366
```

<210> SEQ ID NO 73
<211> LENGTH: 366
<212> TYPE: DNA
<213> ORGANISM: Artificial Sequence
<220> FEATURE:
<223> OTHER INFORMATION: VH

<400> SEQUENCE: 73

```
gaggtgcagc tggtggaatc tggcggagga ctggtgcagc ctggcggctc tctgagactg    60
tcttgcgagg cctccggctt caccttctcc cggaactgga tgtcctgggt gcgacagatc   120
cctggcaagg cctggaatg gtggccgac atcaaggccg acggctccga aaggtgtac      180 ctggactcta tgaagggccg gctgaccatc tcccgggaca cgccagaaa cctgctgtac    240 ctgcagatgg actccctgcg ggtggaagat tccgccctgt actactgtgc cagaggcccc   300
tcttacggcg acagatccga ctacctggac cattggggca gaggcgccct cgtgacagtg   360
tcctct                                                              366
```

```
<210> SEQ ID NO 74
<211> LENGTH: 13
<212> TYPE: PRT
<213> ORGANISM: Artificial Sequence
<220> FEATURE:
<223> OTHER INFORMATION: VH CDR3

<400> SEQUENCE: 74

Gly Pro Ser Tyr Gly Asp Arg Ser Asp Tyr Leu Asp His
1               5                   10

<210> SEQ ID NO 75
<211> LENGTH: 8
<212> TYPE: PRT
<213> ORGANISM: Artificial Sequence
<220> FEATURE:
<223> OTHER INFORMATION: CDR1
<220> FEATURE:
<221> NAME/KEY: MISC_FEATURE
<222> LOCATION: (3)..(3)
<223> OTHER INFORMATION: X is T or D
<220> FEATURE:
<221> NAME/KEY: MISC_FEATURE
<222> LOCATION: (7)..(7)
<223> OTHER INFORMATION: X is N or H

<400> SEQUENCE: 75

Gly Phe Xaa Phe Ser Arg Xaa Trp
1               5

<210> SEQ ID NO 76
<211> LENGTH: 8
<212> TYPE: PRT
<213> ORGANISM: Artificial Sequence
<220> FEATURE:
<223> OTHER INFORMATION: CDR2
<220> FEATURE:
<221> NAME/KEY: MISC_FEATURE
<222> LOCATION: (3)..(3)
<223> OTHER INFORMATION: X is A or K
<220> FEATURE:
<221> NAME/KEY: MISC_FEATURE
<222> LOCATION: (8)..(8)
<223> OTHER INFORMATION: X is K or E

<400> SEQUENCE: 76

Ile Lys Xaa Asp Gly Ser Glu Xaa
1               5

<210> SEQ ID NO 77
<211> LENGTH: 15
<212> TYPE: PRT
<213> ORGANISM: Artificial Sequence
<220> FEATURE:
<223> OTHER INFORMATION: CDR3
<220> FEATURE:
<221> NAME/KEY: MISC_FEATURE
<222> LOCATION: (10)..(10)
<223> OTHER INFORMATION: X is C or S
<220> FEATURE:
<221> NAME/KEY: MISC_FEATURE
<222> LOCATION: (15)..(15)
<223> OTHER INFORMATION: X is H or N

<400> SEQUENCE: 77

Ala Arg Gly Pro Ser Tyr Gly Asp Arg Xaa Asp Tyr Leu Asp Xaa
1               5                   10                  15

<210> SEQ ID NO 78
```

```
<211> LENGTH: 11
<212> TYPE: PRT
<213> ORGANISM: Artificial Sequence
<220> FEATURE:
<223> OTHER INFORMATION: CDR4
<220> FEATURE:
<221> NAME/KEY: MISC_FEATURE
<222> LOCATION: (2)..(2)
<223> OTHER INFORMATION: X is S or W
<220> FEATURE:
<221> NAME/KEY: MISC_FEATURE
<222> LOCATION: (6)..(6)
<223> OTHER INFORMATION: X is P or S

<400> SEQUENCE: 78

Gln Xaa Leu Leu Glu Xaa Asn Gly His Asn Tyr
1               5                   10

<210> SEQ ID NO 79
<211> LENGTH: 9
<212> TYPE: PRT
<213> ORGANISM: Artificial Sequence
<220> FEATURE:
<223> OTHER INFORMATION: CDR6
<220> FEATURE:
<221> NAME/KEY: MISC_FEATURE
<222> LOCATION: (5)..(5)
<223> OTHER INFORMATION: X is Q or K
<220> FEATURE:
<221> NAME/KEY: MISC_FEATURE
<222> LOCATION: (6)..(6)
<223> OTHER INFORMATION: X is T or L

<400> SEQUENCE: 79

Met Gln Pro Leu Xaa Thr Pro Tyr Thr
1               5
```

KLEBSIELLA PNEUMONIAE O3 SPECIFIC ANTIBODIES

FIELD

The invention refers to a cross-neutralizing monoclonal antibody that specifically recognizes a cross-reactive epitope of the lipopolysaccharide (LPS) antigen structure of *Klebsiella pneumoniae*, which is an O3b epitope, cross-reacting with an O3a epitope and an O3 epitope.

BACKGROUND

*Klebsiella pneumoniae* is an important enterobacterial pathogen responsible for nosocomial infections that cause significant morbidity and mortality. Multi-drug resistant (MDR) strains have recently emerged and spread globally, against which therapeutic options are limited. The current aim is to develop therapeutic monoclonal antibodies for the prevention and treatment of infections caused by MDR *Klebsiella* strains. The molecular target of the intended mAbs is the LPS O-antigen that is considered to be one of the few (if not the sole) antigen on the surface of *Klebsiella*.

Based on published epidemiology data (1,2) on O-type distribution, the majority of clinically relevant isolates belong to 4 serotypes, i.e. O1, O2, O3 and O5. O1 and O2 antigens are built up by homopolymers of galactoses (i.e. galactans), while O3 and O5 serogroups are composed of mannose homopolymers (i.e. mannans) (3).

The O3 serotype is characterised by the "classical" penta-mannose structure, also shown in FIG. 3*a* (published in (3)).

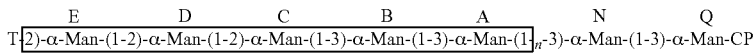

The disaccharide structure formed by N and Q is the so-called adaptor bridging the pentamannose O-antigen subunits to the common part (CP). The last O-antigen repeat is capped by a terminator molecule (T), which in fact is a 3-linked methyl-phosphate as elucidated by Kubler-Kielb et al. (4)

The penta-mannose structure of *Klebsiella* O3 antigen was elucidated (10). The rfb operon encoding this O3 antigen has been deposited in Genbank under accession number AB795941.1.

*E. coli* serotypes O8 and O9 have structurally the same O-specific mannose homopolysaccharide as *Klebsiella* serotypes O5 and O3, respectively. A monoclonal antibody that serotypically discriminates *E. coli* O9a, a subtype of *E. coli* O9, from *E. coli* O9 has been described (Sugiyama et al. 1998, J. Bacteriol. 180(10):2775-2778). *E. coli* O9 and O9a are structurally and serologically similar to each other.

The structure of *E. coli* O9 as well as the genetic determinants thereof is identical to those of the *Klebsiella* O3 antigen. A subtype of serogroup O9, i.e. *E. coli* O9a was proven to result from a point mutation within WbdA (7). The structure of O9a was shown to be a tetra-mannose structure (8).

TABLE

Structure of repeating units of O-specific mannose homopolysaccharide
(published in Sugiyama et al.)

| Serotype(s) | Structure of the O-antigen repeating unit |
| --- | --- |
| *E. coli* O8 and *Klebsiella* O5 . . . | → $_3Man_1$ —β→ $_2Man_1$ —α→ $_2Man_1$ —α→ |
| *E. coli* O9a . . . | → $_3Man_1$ —α→ $_3Man_1$ —α→ $_2Man_1$ —α→ $_2Man_1$ —α→ |
| *E. coli* O9 and *Klebsiella* O3 . . . | → $_3Man_1$ —α→ $_3Man_1$ —α→ $_2Man_1$ —α→ $_2Man_1$ —α→ $_2Man_1$ —α→ |

An anti-*E. coli* O9a monoclonal antibody has been described to cross-react with *Klebsiella* O3 polysaccharide, suggesting the presence of *E. coli* O9a type O polysaccharides in *Klebsiella* O3 strains (Kido et al. 1997, Microbiol. Immunol. 41:519-525). The antibody recognized the *E. coli* O9a polysaccharide but not the *E. coli* O9. The minimum number of mannose residues needed to define the O9 and O9a polysaccharide was determined to be four, and the 4-mannose structure has been described to be the shortest candidate for the epitope bound by the antibody.

Van der Meer et al. (Infection and Immunity 1994, 62(3):1052-1057) describe a monoclonal antibody (mAb) raised against *Salmonella minnesota* R595 and specific for a structure of the inner core, which is α-3-deoxy-D-manno-octulosonic acid. The antibody reacted with almost all O-serotypes of *Klebsiella pneumoniae*, suggesting an epitope in the core of the LPS like that in the inner core of *S. minnesota*.

Trautmann et al. (Infection and Immunity 1994, 62(4): 1282-1288) describe a murine monoclonal antibody directed against. *Klebsiella* lipopolysaccharide (LPS), which was raised with a smooth, nonencapsulated *Klebsiella* strain (serogroup O1) and cross-reacted with *Klebsiella* O serogroups O1, O2ab, O2ac, O3, O3, O5, and O12.

WO2008/135446A2 discloses peptidic *Klebsiella* antigens and antibodies.

Pollack et al. (Journal of Clinical Investigation 1987, 79(5):1421-1430) describe mAbs recognizing epitopes in the core-Lipid A region of LPS.

Yokochi et al. (Infection and Immunity 1992, 60(11): 4953-4956) describe adjuvant activity of LPS from *K. pneumoniae*. It is suggested that the adjuvanticity of *Klebsiella* O3 LPS might require a combination of the *Klebsiella* lipid A moiety and the mannose homopolysaccharide moiety.

Curvall et al. (Acta Chemica Scandinavica 1973, 27:2645-2649) disclose the structure of O-specific side chains in a *Klebsiella* O3 LPS. The *Klebsiella* O3:K58 LPS is described to be composed of pentasaccharide repeating units.

There is a need for new antibodies recognizing targets of *Klebsiella pneumoniae* with broadened coverage of different *K. pneumoniae* serotypes, in particular for developing effective therapies.

SUMMARY

It is the objective of the present invention to provide for an antibody directed against *K. pneumoniae* with improved relevance to target the pathogen, to be used for the prevention or therapy of *K. pneumoniae* infections.

The object is solved by the subject of the present invention.

According to the invention, there is provided a cross-neutralizing monoclonal antibody that specifically recognizes a cross-reactive epitope of the LPS antigen structure of *Klebsiella pneumoniae*, which is an O3b epitope, cross-reacting with an O3a epitope and an O3 epitope, wherein the antibody comprises any one of a) the CDR1-CDR6 sequences of any of the antibodies listed in FIG. 1, in particular Table 1a or Table 1b; or b) the VH and VL sequences of any of the antibodies depicted in FIG. 2*b*; or c) which is a functionally active variant of a parent antibody that is characterized by the sequences of a) or b), wherein the functionally active variant has a specificity to bind the same epitope as the parent antibody or to compete with the parent antibody, and comprises at least one functionally active CDR variant of any of the CDR1-CDR6 of the parent antibody (the parent CDR sequence), which functionally active CDR variant comprises at least one point mutation in the parent CDR sequence, and consists of the amino acid sequence that has at least 60% sequence identity with the parent CDR sequence, preferably at least 70%, at least 80%, or at least 90% sequence identity.

In particular, the antibody of the invention is a cross-neutralizing monoclonal antibody that specifically recognizes a cross-reactive epitope of the lipopolysaccharide (LPS) antigen structure of *Klebsiella pneumoniae*, which is an O3b epitope, cross-reacting with an O3a epitope and an O3 epitope, which antibody is selected from any of a) an antibody comprising the CDR1-CDR6 sequences of any one of the antibodies listed in Table 1a or Table 1b; or b) an antibody comprising the VH and VL sequences of any one of the antibodies depicted in FIG. 2*b*; or c) an antibody which is a functionally active variant of a parent antibody that is any one of the antibodies of a) or b), which functionally active variant has a specificity to bind the same epitope as the parent antibody, and comprises at least one point mutation in any of the CDR, wherein the number of point mutations is either 0, 1, 2, or 3 point mutations in each of the CDR sequences, which has at least 60% sequence identity to the respective parent CDR sequence.

Specifically, the functionally active variant is provided wherein the sequence identity in each of the CDR sequences is at least 60% compared to the respective CDR sequences of the parent antibody.

Specifically, the antibody is an antibody characterized by the antigen binding site of any of the antibodies listed in FIG. 1, in particular an antibody which is

A)

selected from the group consisting of group members i) to v), wherein i)

is an antibody which comprises a) CDR1 consisting of the amino acid sequence SEQ ID 21;

b) CDR2 consisting of the amino acid sequence SEQ ID 22;

c) CDR3 consisting of the amino acid sequence of SEQ ID 23;

d) CDR4 consisting of the amino acid sequence SEQ ID 33;

e) CDR5 consisting of the amino acid sequence SEQ ID 34; and f) CDR6 consisting of the amino acid sequence of SEQ ID 35;

ii)

is an antibody which comprises a) CDR1 consisting of the amino acid sequence SEQ ID 24;

b) CDR2 consisting of the amino acid sequence SEQ ID 25;

c) CDR3 consisting of the amino acid sequence of SEQ ID 26;

d) CDR4 consisting of the amino acid sequence SEQ ID 36;

e) CDR5 consisting of the amino acid sequence SEQ ID 37; and f) CDR6 consisting of the amino acid sequence of SEQ ID 38;

iii)
is an antibody which comprises
a) CDR1 consisting of the amino acid sequence SEQ ID 27;
b) CDR2 consisting of the amino acid sequence SEQ ID 28;
c) CDR3 consisting of the amino acid sequence of SEQ ID 29;
d) CDR4 consisting of the amino acid sequence SEQ ID 39;
e) CDR5 consisting of the amino acid sequence SEQ ID 40; and
f) CDR6 consisting of the amino acid sequence of SEQ ID 41;
iv)
is an antibody which comprises
a) CDR1 consisting of the amino acid sequence SEQ ID 30;
b) CDR2 consisting of the amino acid sequence SEQ ID 31;
c) CDR3 consisting of the amino acid sequence of SEQ ID 32;
d) CDR4 consisting of the amino acid sequence SEQ ID 42;
e) CDR5 consisting of the amino acid sequence SEQ ID 34; and
f) CDR6 consisting of the amino acid sequence of SEQ ID 43; and
v)
is an antibody which comprises
a) CDR1 consisting of the amino acid sequence SEQ ID 21;
b) CDR2 consisting of the amino acid sequence SEQ ID 22;
c) CDR3 consisting of the amino acid sequence of SEQ ID 74;
d) CDR4 consisting of the amino acid sequence SEQ ID 33;
e) CDR5 consisting of the amino acid sequence SEQ ID 34; and
f) CDR6 consisting of the amino acid sequence of SEQ ID 35;
wherein CDR sequences are designated according to the numbering system of Kabat;
or
B) an antibody which is the functionally active variant of a parent antibody that is any of the group members of A. In particular, the functionally active variant is characterized by the features further described herein.

Specifically, the CDR sequences according to Kabat as referred to herein are understood as those amino acid sequences of an antibody as determined according to Kabat nomenclature (see Kabat et al., Sequences of Proteins of Immunological Interest, 5$^{th}$ Ed. Public Health Service, U.S. Department of Health and Human Services. (1991)).

Specifically, the antibody is
A)
selected from the group consisting of group members i) to v), wherein
i)
is an antibody which comprises
a) CDR1 consisting of the amino acid sequence SEQ ID 44;
b) CDR2 consisting of the amino acid sequence SEQ ID 45;
c) CDR3 consisting of the amino acid sequence of SEQ ID 46;
d) CDR4 consisting of the amino acid sequence SEQ ID 56;
e) CDR5 consisting of the amino acid sequence SEQ ID 57; and
f) CDR6 consisting of the amino acid sequence of SEQ ID 58;
ii)
is an antibody which comprises
a) CDR1 consisting of the amino acid sequence SEQ ID 47;
b) CDR2 consisting of the amino acid sequence SEQ ID 48;
c) CDR3 consisting of the amino acid sequence of SEQ ID 49;
d) CDR4 consisting of the amino acid sequence SEQ ID 59;
e) CDR5 consisting of the amino acid sequence SEQ ID 60; and
f) CDR6 consisting of the amino acid sequence of SEQ ID 61;
iii)
is an antibody which comprises
a) CDR1 consisting of the amino acid sequence SEQ ID 50;
b) CDR2 consisting of the amino acid sequence SEQ ID 51;
c) CDR3 consisting of the amino acid sequence of SEQ ID 52;
d) CDR4 consisting of the amino acid sequence SEQ ID 62;
e) CDR5 consisting of the amino acid sequence SEQ ID 63; and
f) CDR6 consisting of the amino acid sequence of SEQ ID 64;
iv)
is an antibody which comprises
a) CDR1 consisting of the amino acid sequence SEQ ID 53;
b) CDR2 consisting of the amino acid sequence SEQ ID 54;
c) CDR3 consisting of the amino acid sequence of SEQ ID 55;
d) CDR4 consisting of the amino acid sequence SEQ ID 65;
e) CDR5 consisting of the amino acid sequence SEQ ID 57; and
f) CDR6 consisting of the amino acid sequence of SEQ ID 66; and
v)
is an antibody which comprises
a) CDR1 consisting of the amino acid sequence SEQ ID 44;
b) CDR2 consisting of the amino acid sequence SEQ ID 45;
c) CDR3 consisting of the amino acid sequence of SEQ ID 67;
d) CDR4 consisting of the amino acid sequence SEQ ID 56;
e) CDR5 consisting of the amino acid sequence SEQ ID 57; and
f) CDR6 consisting of the amino acid sequence of SEQ ID 58;
wherein CDR sequences are designated according to the numbering system of IMGT;
or
B) an antibody which is the functionally active variant of a parent antibody that is any of the group members of A. In particular, the functionally active variant is characterized by the features further described herein.

Specifically, each of the group members i) to v) may be used as a parent antibody to produce a functionally active variant antibody. Specifically, wherein the functionally active variant comprises CDR1-6, wherein
   a) the CDR1 comprises SEQ ID 75;
   b) the CDR2 comprises SEQ ID 76;
   c) the CDR3 comprises SEQ ID 77;
   d) the CDR4 comprises SEQ ID 78;
   e) the CDR5 comprises SEQ ID 57; and
   f) the CDR6 comprises SEQ ID 79,
   which CDR sequences are according to IMGT,
and wherein each of the CDR sequences has at least 60% sequence identity to the respective CDR sequence of said parent antibody.

SEQ ID 75: GFXFSRXW,
   wherein X at position 3 is T or D;
   wherein X at position 7 is N or H.
SEQ ID 76: IKXDGSEX,
   wherein X at position 3 is A or K;
   wherein X at position 8 is K or E;
SEQ ID 77: ARGPSYGDRXDYLDX,
   wherein X at position 10 is C or S;
   wherein X at position 15 is H or N;
SEQ ID 78: QXLLEXNGHNY
   wherein X at position 2 is S or W;
   wherein X at position 6 is P or S;
SEQ ID 79: MQPLXTPYT
   wherein X at position 5 is Q or K;
   wherein X at position 6 is T or L.

Specifically, the CDR sequences according to IMGT as referred to herein are understood as those amino acid sequences of an antibody as determined according to the IMGT system (The international ImMunoGeneTics, Lefranc et al., 1999, Nucleic Acids Res. 27: 209-212).

According to a specific embodiment, the antibody is
A)
selected from the group consisting of group members i) to viii), wherein
   i)
   is an antibody which comprises
   a) VH consisting of the amino acid sequence SEQ ID 11; and
   b) VL consisting of the amino acid sequence SEQ ID 16;
   ii)
   is an antibody which comprises
   a) VH consisting of the amino acid sequence SEQ ID 12; and
   b) VL consisting of the amino acid sequence SEQ ID 17;
   iii)
   is an antibody which comprises
   a) VH consisting of the amino acid sequence SEQ ID 13; and
   b) VL consisting of the amino acid sequence SEQ ID 18;
   iv)
   is an antibody which comprises
   a) VH consisting of the amino acid sequence SEQ ID 14; and
   b) VL consisting of the amino acid sequence SEQ ID 19;
   v)
   is an antibody which comprises
   a) VH consisting of the amino acid sequence SEQ ID 15; and
   b) VL consisting of the amino acid sequence SEQ ID 20;
   vi)
   is an antibody which comprises
   a) VH consisting of the amino acid sequence SEQ ID 68; and
   b) VL consisting of the amino acid sequence SEQ ID 16;
   vii)
   is an antibody which comprises
   a) VH consisting of the amino acid sequence SEQ ID 69; and
   b) VL consisting of the amino acid sequence SEQ ID 16;
   viii)
   is an antibody which comprises
   a) VH consisting of the amino acid sequence SEQ ID 70; and
   b) VL consisting of the amino acid sequence SEQ ID 16;
   or
B) an antibody which is the functionally active variant of a parent antibody that is any of the group members of A. In particular, the functionally active variant is characterized by the features further described herein.

Specifically, the functionally active variants of the antibodies described herein is a functional variant of such antibody e.g., a functional variant which substantially has the same binding specificity as the exemplified antibodies listed in the tables of FIG. 1, comprising the binding site formed by the six CDR sequences provided therein, and/or formed by pairing respective VH and VL antibody domains, e.g. the VH and VL domains characterized by the sequences provided in FIG. 2.

For the purpose of providing variants, such antibodies are herein referred to as parent antibodies, and CDR or framework (FR) sequences are herein referred to as parent CDR or parent framework sequences. It is well understood that any antibody sequence as described herein is considered a "parent" sequence which can be subject to variation e.g., by one or more point mutations.

According to a specific aspect, the functional variant antibody binds the same epitope as the parent antibody.

According to a further specific aspect, the functional variant antibody comprises the same binding site as the parent antibody.

Typically, such variant antibodies are competitively binding to the cross-reactive epitope. Competition of binding is preferably determined by competition ELISA analysis or by BLI or ForteBio analysis.

The antibody or the functional variant of any of the exemplified antibodies (parent antibodies) which competitively binds to any of the parent antibodies is specifically characterized by a relative inhibition of binding to its target as determined by competition ELISA analysis or by BLI or ForteBio analysis, which relative inhibition is preferably greater than 30%.

Specifically, the exemplified antibodies and functional variants thereof are characterized by the binding specificity directed to the O3b epitope and structure, which is also incorporated in the O3a and O3 structures, resulting in the cross-reactivity, also referred to as pan-O3 specificity. Specifically, the exemplified antibodies recognize mannan structures that are obviously contained in these O3 group serotypes.

Besides, the cross-reactive epitope may also be expressed by any other *K. pneumoniae*, such as serotype O5. In some cases, the antibody was found to cross-react with O5 LPS, for example, mAb UaLPLO3-095 (herein also referred to as MPG-095) also reacted with a *K. pneumoniae* O5 antigen, which is a mannan LPS molecule, characterized by mannose repeating units. Accordingly, crossreactivity of the antibodies described herein with mannan on other organisms (microorganisms, such as *Saccharomyces cerevisiae, Hafnia alvei* or HIV) and even cancer cells etc. is possible.

According to a further specific aspect, the antibody does not cross-react with an epitope of non-mannan LPS molecules of *Klebsiella pneumoniae*. Such non-mannan LPS molecules are e.g., O1, O2, O4, O12 LPS molecules. Specifically, the antibody does not cross-react with any other *K. pneumoniae* antigen, and/or the antibody binds to any other *K. pneumoniae* non-mannan LPS antigen with a lower affinity e.g., where the $K_D$ difference to preferentially bind any or all of the O3b, O3a, or O3 epitopes over other *K. pneumoniae* antigens (other than any of the O3b, O3a, or O3 antigens) is at least 2 logs, preferably at least 3 logs.

Specifically, the non-cross-reaction is determined by an immune assay ELISA, immunoblot, flow cytometry, BLI) using any or all of the O3b, O3a, or O3 antigens or bacteria expressing the antigens as well as additional control antigen(s), to which the antibody does not significantly bind.

Functionally active variant antibodies may differ in any of the VH or VL sequences, or share the common VH and VL sequences, and comprise modifications in the respective FR. The variant antibody derived from the parent antibody by mutagenesis may be produced by methods well-known in the art.

Functional variants of an antibody may specifically be engineered to obtain CDR mutated antibodies (including at least one CDR variant) e.g., to improve the affinity of an antibody. Specifically, the functionally active variant is a functionally active CDR variant which comprises at least one point mutation in the parent CDR sequence, and comprises or consists of the amino acid sequence that has at least 60% sequence identity with the parent CDR sequence, preferably at least 70%, at least 80%, at least 90% sequence identity.

A specific variant is e.g., a human or artificial variant of the parent antibody, wherein the parent CDR sequences are incorporated into human or artificial framework sequences (e.g. of non-human origin, such as human framework sequences including one or more point mutations), wherein optionally 1, 2, 3, or 4 amino acid residues of each of the parent CDR sequences may be further mutated by introducing point mutations to improve the stability, specificity and affinity of the parent or humanized antibody.

According to a specific aspect, the antibody comprises artificial CDR and framework sequences e.g., of non-human origin, wherein at least one of the CDR and framework sequences includes one or more point mutations such as to obtain artificial, non-naturally occurring sequences.

According to a specific aspect, a) the O3b epitope is incorporated in the LPS O3b antigen of *Klebsiella pneumoniae* comprising the structure of Formula (I), including one or more O3b antigen trimannose homopolymer repeating units, wherein Formula (I) is:

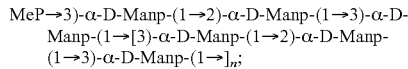

b) the O3a epitope is incorporated in the LPS O3a antigen of *Klebsiella pneumoniae* comprising the structure of Formula (II), including one or more O3a antigen tetramannose homopolymer repeating units, wherein Formula (II) is:

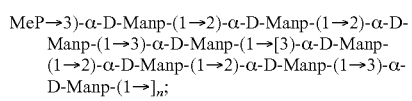

and c) the O3 epitope is incorporated in the LPS O3 antigen of *Klebsiella pneumoniae* comprising the structure of Formula (III), including one or more O3 antigen pentamannose homopolymer repeating units, wherein Formula (III) is:

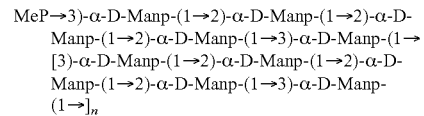

wherein
MeP is methyl phosphate; and
n is 0-50.

Specifically, the methyl phosphate group is situated at the non-reducing end of the mannose residue.

The O3b epitope is specifically characterized by the trimannose repeating unit set forth in Formula (I).

The O3a epitope is specifically characterized by the tetramannose repeating unit set forth in Formula (II).

The O3 epitope is specifically characterized by the pentamannose repeating unit set forth in Formula (III).

Such cross-reacting antibody is characterized by the O3 group specificity, which is directed to the O3b epitope and further directed to both of the O3a and O3 epitopes (i.e. cross-reacting). Specifically, the antibody is a pan-O3 specific antibody, specifically recognizing or binding to the O3b-epitope and cross-reacting with the O3a-epitope and the O3-epitope. Cross-reactivity is specifically based on the presence of the O3b-epitope in the O3a and O3 LPS antigens.

Specifically the antibody is a high affinity antibody binding the epitope recognized by the cross-reactive antibody (herein referred to as the cross-reactive epitope) e.g., as determined with an O3a antigen, with a $K_D$ of less than $10^{-6}$M, preferably less than $10^{-7}$M, by biolayer interferometry for bivalent binding (e.g. for a full-length IgG antibody), in particular using the method described in the Example 2, employing a fortéBIO Octet Red instrument and fortéBIO analysis. Such method specifically determines the avidity of binding, herein also referred to as "avid binding affinity".

The high affinity of binding can be confirmed when determining the affinity for the respective Fab fragment (monovalent binding).

The high binding affinity as described herein specifically relates to any of avid binding affinity (as determined for a bivalent binder) and/or the affinity (as determined for the monovalent binder).

According to a specific embodiment, the antibody has an affinity to bind any or all of the O3b, O3a, or O3 antigens, in particular the O3a antigen or epitope with a $K_D$ of less than $10^{-6}$M, preferably less than $10^{-7}$M, even more preferably less than $10^{-8}$M, or preferably less than $10^{-9}$M, or preferably less than $10^{-10}$M e.g., with an affinity in the picomolar range (e.g., $K_D$ as a measure of avid binding affinity, when determining avid binding affinity upon bivalent binding), and/or a $K_D$ of less than $10^{-6}$M, preferably less than $10^{-7}$M, less than $10^{-6}$ M, or less than $10^{-9}$ M (when determining affinity upon monovalent binding).

Specifically, the pan-O3 specific antibody is capable of binding each of the O3b-epitope, the O3a-epitope and the O3-epitope with a high affinity, such as with a $K_D$ of less than $10^{-6}$M, preferably less than $10^{-7}$ M, preferably less than $10^{-6}$ M, even more preferably less than $10^{-9}$ M (when determining avid binding affinity upon bivalent binding, or when determining affinity upon monovalent binding).

Yet, the antibody may preferentially bind any of the O3b, O3a, or O3 antigens over the other O3 group antigens (e.g., with a $K_D$ difference of 1 or 2 logs).

Variants of parent antibodies (e.g., using the exemplified mAbs as parent mAbs) which are produced by affinity maturation employing standard mutagenesis techniques, herein referred to as affinity-matured variants, may have an increased (avid) binding affinity, with a $K_D$ difference of at least 1 log, or 2 logs, or 3 logs, as compared to the parent antibody. Affinity matured variants typically have an affinity to bind the O3b-antigen with a $K_D$ of less than $10^{-7}$ M, or less than $10^{-8}$ M. If the parent antibody has an affinity with a $K_D$ of less than $10^{-7}$ M, or less than $10^{-8}$ M, and the parent antibody is undergoing affinity maturation, the affinity matured variant may have an even higher affinity with a $K_D$ of less than $10^{-8}$ M and less than $10^{-9}$ M, respectively.

O3b, O3a, or O3 epitopes or the respective antigens are herein referred to as O3 group epitopes or antigens (or O3 group type). Specifically, the antibody described herein is capable of *K. pneumoniae* surface binding of O3 group antigens, herein referred to as O3 group cross-reactive antibodies, such as determined by Flow Cytometry.

In particular, the antibody is a cross-neutralizing antibody, which has a neutralization potency to neutralize endotoxin of *Klebsiella pneumoniae* strains serotype O3b, O3a, and O3. Specifically, the antibody is neutralizing endotoxin of *Klebsiella pneumoniae* strains expressing LPS molecules comprising any of the O3 group epitopes or the respective antigens, e.g., as determined by an in vitro or in vivo detection method.

Specifically, the antibody neutralizes the endotoxic effect of bacteria expressing the corresponding specific LPS molecules in vivo. Its function may be determined by in vitro assays. The antibody is specifically effective against *Klebsiella pneumoniae* of the O3 group type by neutralizing endotoxin functions e.g., as determined by an in vitro LAL assay, or toll-like receptor 4 (TLR4) reporter assay e.g., with at least 20% reduction in endotoxin activities in comparison to control samples (no antibody or irrelevant control mAb added).

The antibody may specifically neutralize lethal endotoxemia. Such functional activity may be determined in an appropriate in vivo model e.g., the GalN model of endotoxemia, such as described in Galanos et al. (Proc. Natl. Acad. Sci. 1979, 76:5939-5943). According to a certain aspect, the antibody neutralizes the targeted pathogen in animals, including both, human and non-human animals, and inhibits pathogenesis in vivo, preferably any models of primary and secondary bacteremia, pneumonia, urinary tract infection, liver abscess, peritonitis, or meningitis.

Specifically, the neutralization potency is at least the potency of any of the exemplified antibodies characterized by the CDR sequences identified in FIG. 1 and/or characterized by the VH and VL sequences identified in FIG. 2, which are used as reference antibody when determining the neutralization potency of functional variants.

According to a certain aspect, the antibody is any one of a full-length antibody, an antibody fragment thereof, or a fusion protein, each comprising at least VH and VL antibody domains incorporating a binding site recognizing the cross-reactive epitope. Specifically, the antibody is any of full-length IgG1, a bispecific IgG1, or a F(ab')$_2$-fragment.

Specifically, the antibody is a human antibody, or a derivative thereof incorporating artificial or animal sequences (other than human), e.g. a human IgG antibody, or an antibody comprising human CDR sequences or any functional CDR variant thereof and an animal (non-human) framework, such as to obtain an animalized, e.g. caninized antibody.

Specifically, the antibody described herein is a fully human antibody.

The antibodies described in the examples are of human origin, or an affinity matured variant thereof, specifically wherein the antibody is a non-naturally occurring antibody which comprises an artificial amino acid sequence. Variants comprising artificial sequences (non-naturally occurring) may be obtained by mutagenesis or as further described herein.

Specifically, the antibody is an IgA antibody, or an IgA to IgG isotype switch variant thereof. The Fc portions can be of any immunoglobulin isotype, and in particular of an IgG (e.g., an IgG1) antibody According to a specific aspect, the antibody of the invention comprises CDR and framework sequences, wherein the framework sequences include human, artificial or animal sequences. Specifically the antibody comprises one or more constant domains, which are of an IgG antibody e.g., of an IgG1, IgG2, IgG3, or IgG4 subtype, or of an IgA1, IgA2, IgD, IgE, or IgM antibody.

It is feasible that variant VH or VL domains e.g., with modifications in the respective FR or CDR sequences as compared to the VH and VL, respectively, of any of the antibodies as shown in FIG. 2b (herein referred to as "parent" VH or "parent VL") may be used, which are functionally active e.g., binding to the same epitope or comprising the same binding site or having the same binding characteristics as the parent antibody. It is also feasible that some of the FR or CDR sequences of the antibodies described herein may be exchanged by those of other antibodies.

Specifically, the variant VH or variant VL may be provided, which comprises a) the set of 6 CDR (CDR1-6) sequences of the parent VH or VL, or the set of 6 CDR (CDR1-6) sequences, specifically wherein at least one of the CDR sequences is a functionally active CDR variant of the parent CDR as further described herein; and b) FR sequences characterized by at least 60% sequence identity with the FR sequences of the parent VH or VL, preferably at least 70%, at least 80%, or at least 90% sequence identity.

Specifically, the antibody comprises a functionally active CDR variant of any of the CDR sequences listed in FIG. 1, wherein the functionally active CDR variant comprises at least one of a) 1, 2, or 3 point mutations in the parent CDR sequence; and/or b) 1 or 2 point mutations in any of the four C-terminal or four N-terminal, or four centric amino acid positions of the parent CDR sequence; and/or c) at least 60% sequence identity with the parent CDR sequence, preferably at least 60% sequence identity in each of the CDR1-CDR6 sequences;

preferably wherein the functionally active CDR variant comprises 1 or 2 point mutations in any CDR sequence consisting of less than 4 or 5 amino acids.

Specifically, the functionally active variant differs from the parent antibody in at least one point mutation in the amino acid sequence, preferably in the CDR, wherein the number of point mutations in each of the CDR amino acid sequences is either 0, 1, 2 or 3.

According to a specific aspect, the point mutation is any of an amino acid substitution, deletion and/or insertion of one or more amino acids.

According to a specific aspect, the antibody is provided for use in treating a subject at risk of or suffering from *K. pneumoniae* infection or colonization to limit the infection in the subject or to ameliorate a disease condition resulting from said infection, preferably for treatment or prophylaxis of any of primary and secondary bacteremia, pneumonia, urinary tract infection, liver abscess, peritonitis, or meningitis.

Therefore, the invention further provides for a method of treating a subject by administering an effective amount of the antibody in the respective indications.

Specifically, the subject is a human being. Specifically, the subject is any human being who is healthy or suffering from a disease. Specifically, the human being is an immunodeficient, in particular an immunocompromised or immunosuppressed patient, or a contact thereof.

Specifically, the subject is of a host group characterized by an impaired phagocyte number and/or function, which host group is any of
a) patients suffering from inherited or acquired primary or secondary immunodeficiency;
b) patients selected from the group consisting of neonates younger than 28 days of age, elderly patients older than 65 years of age, patients suffering from Diabetes mellitus, renal failure, cirrhosis, Trisomie 21, trauma, or HIV, or patients who have undergone surgical interventions or systemic treatment with corticosteroids; or
c) patients admitted to hospital or hospital personnel, in particular at an acute-care or intensive care unit, with a risk of contracting infection upon exposure to a patient suffering from *K. pneumoniae* disease.

Specifically, the antibody is used to prevent nosocomial or iatrogenic outbreaks of *K. pneumoniae* disease.

Specifically, the antibody is provided for use according to the invention, wherein a systemic infection or colonization with *K. pneumoniae* of the O3 type in a subject is determined ex vivo by contacting a biological sample of said subject with the antibody, wherein a specific immune reaction of the antibody determines the infection or colonization.

The invention further provides for a pharmaceutical preparation comprising the antibody as described herein, and a pharmaceutically acceptable carrier or excipient in a parenteral (e.g., i.v. or i.m.) formulation.

The invention further provides for an isolated nucleic acid encoding the antibody as described herein.

The invention further provides for an expression cassette or a plasmid comprising a coding sequence to express a proteinaceous construct, such as comprising or consisting of a polypeptide or protein, or a protein derivative, comprising the binding site or the a VH and/or VL of the antibody as described herein.

The invention further provides for a host cell comprising an expression cassette or a plasmid as described herein.

The invention further provides for a method of producing the antibody as described herein, wherein the host cell is cultivated or maintained under conditions to produce said antibody.

Specifically preferred is a host cell and a production method employing such host cell, which host cell comprises the plasmid or expression cassette of the invention, which incorporates a coding sequence to express the antibody light chain; and
the plasmid or expression cassette of the invention, which incorporates a coding sequence to express the antibody heavy chain.

BRIEF DESCRIPTION OF THE DRAWINGS

FIG. 1: Tables 1a and 1b:
Table 1a: CDR sequences of exemplified monoclonal antibodies (mAbs), wherein CDR sequences are designated according to the numbering system of Kabat;
Table 1b: CDR sequences of exemplified monoclonal antibodies (mAbs), wherein CDR sequences are designated according to the numbering system of IMGT;
The nomenclature as used herein shall have the following meaning:
VH CDR1=CDR1
VH CDR2=CDR2
VH CDR3=CDR3
VL CDR4=CDR4=VL CDR1
VL CDR5=CDR5=VL CDR2
VL CDR6=CDR6=VL CDR3
The VH and VL sequences of antibodies listed in Table 1a and 1b are provided in FIG. 2.

The antibody designated as UaLPLO3-601 is herein also referred to as MPG-601, mAb 601 or MPGO3-601;
The antibody designated as UaLPLO3-095 is herein also referred to as MPG-095 or MPGO3-095;
The antibody designated as UaLPLO3-208L is herein also referred to as MPG-208L or MPGO3-208L;
The antibody designated as UaLPLO3-547 is herein also referred to as MPG-547 or MPGO3-547;
The antibody designated as UaLPLO3-555 is herein also referred to as MPG-555 or MPGO3-555.

The antibody designated as MPG601 C108S is a mutant of MPG-601 comprising a point mutation C108S in the VH sequence, as described in Example 7. The light chain (VL-CDR and VL) sequences of the antibody designated as MPG601 C108S are the same as for the antibody designated as MPG-601.

The antibody designated as MPG601 H97Y is a mutant of MPG-601 comprising a point mutation H97Y in the VH sequence, as described in Example 7. The light chain (VL-CDR and VL) sequences of the antibody designated as MPG601 H97Y are the same as for the antibody designated as MPG-601.

The antibody designated as MPG601 C108S/H97Y is a mutant of MPG-601 comprising the point mutations C108S and H97Y in the VH sequence, as described in Example 7. The light chain (VL-CDR and VL) sequences of the antibody designated as MPG601 C108S/H97Y are the same as for the antibody designated as MPG-601.

FIG. 2: VH and VL sequences of exemplified mAbs: nucleotide sequences (FIG. 2*a*), and amino acid sequences (FIG. 2*b*).

FIG. 3: Identification of fully human anti-*Klebsiella pneumoniae* O3 O-antigen antibodies (a) Schematic linear chemical structure of the O3 O-antigen bait including the assumed biotinylation site; Box shows repetitive unit; CP=common part;*=(4−1) αHep or H. (b) Fluorescence intensity and sort gate (boxed) of single O3 O-antigen bait (black close circle) or non-reactive (grey open circle) 7-AAD⁻, CD19⁺ lamina propria cells. (c) Number of IGHV somatic hypermutations of IgA lamina propria plasmablasts. Concentration-dependent binding of monoclonal IgG1 antibodies to the biotinylated O3-antigen bait by ELISA (d) and binding to whole O3a LPS by Immuno Blot (e); mGO53=negative control. (f) Area under curve (AUC) values from ELISA data to biotinylated O3 O-antigen and Streptavidin (SA) as shown in (d); lines connect the same antibody; b,f-h: Representative data from at least two independent experiments; Solid lines show mean; error bars=standard deviation; dashed lines=negative cut-off FIG. 3: Ig gene features (table)

Figure 4:
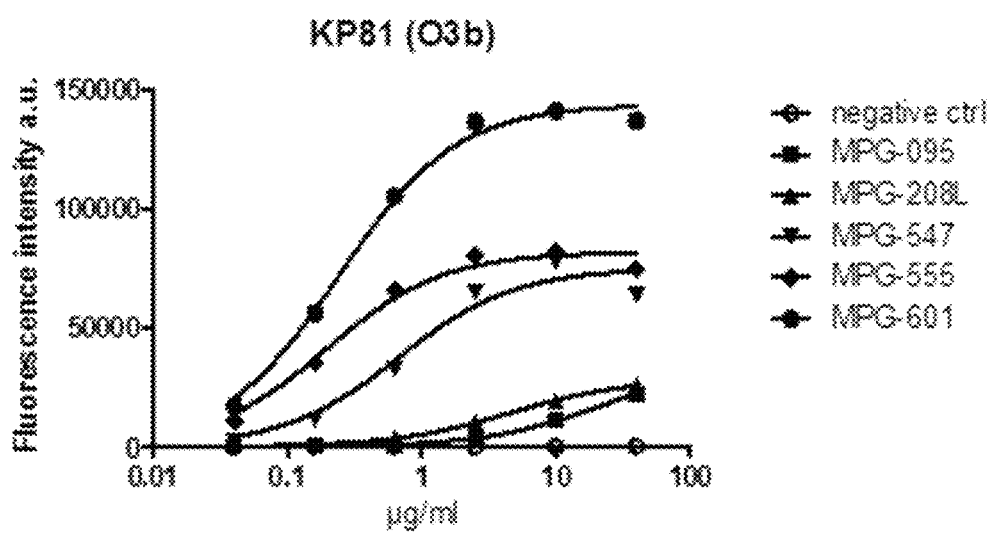

FIG. 4: Titration of human O3 mAbs in surface staining on A) strain PCM-11 (O3a), B) strain Kp14 (O3) and C) strain Kp81 (O3b).

Figure 5A:
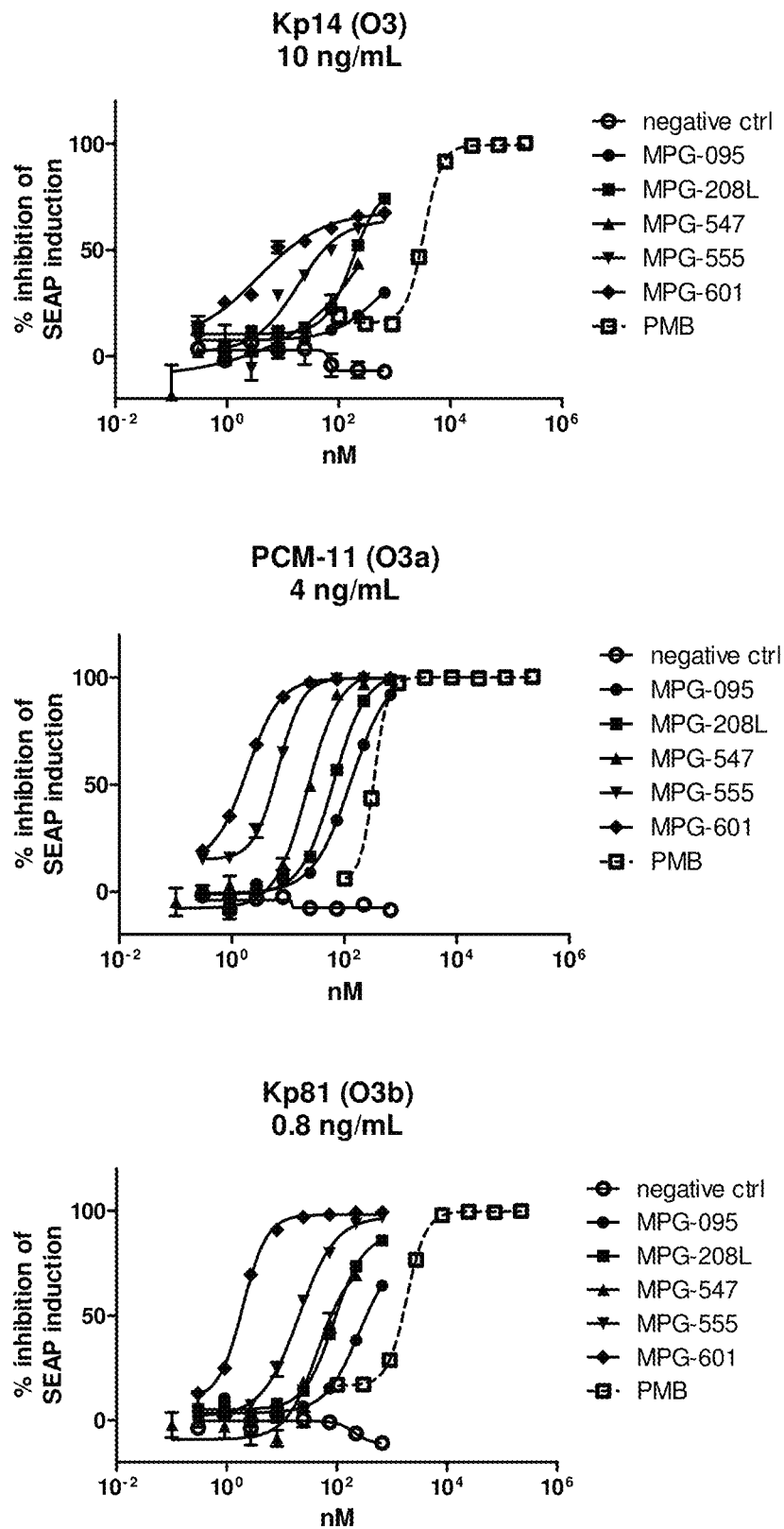

FIG. 5a: LPS neutralization in in vitro assays by O3 mAbs. PMB indicated polymyxin B, a potent LPS neutralizing agent, used as positive control.

Figure 5B:
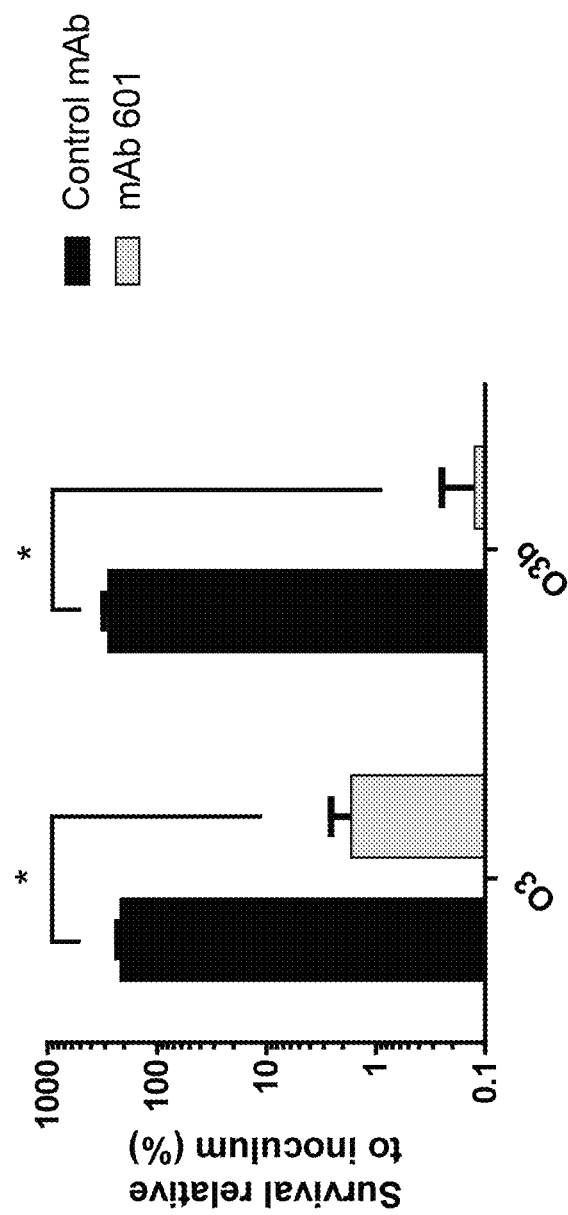

FIG. 5b. Serum bactericidal assay to determine CDC activity. K. pneumoniae clinical isolates A) Kp14 and B) Kp81 were cultured in 50% depleted human serum in the presence of 2.5 µg/ml of specific or control mAb. Bactericidal activity is expressed as percentage of recovered bacteria after 3 h incubation vs the inoculum (T0) as determined by plating aliquots at both time points. Graph shows combined results of 4 experiment (2 repeats with both donor sera). Bars indicate mean with SEM. The difference between control mAb and mAb 601 was considered statistically significant if p<0.05 with Mann-Whitney test (indicated with *).

FIG. 6: Protection elicited by O3 specific mAbs (200 and 20 µg/mouse) against a lethal challenge by live K. pneumoniae in the GalN sensitized mouse model of bacteraemia. Graphs show results of one representative experiment with groups of 5 mice.

Figure 7:
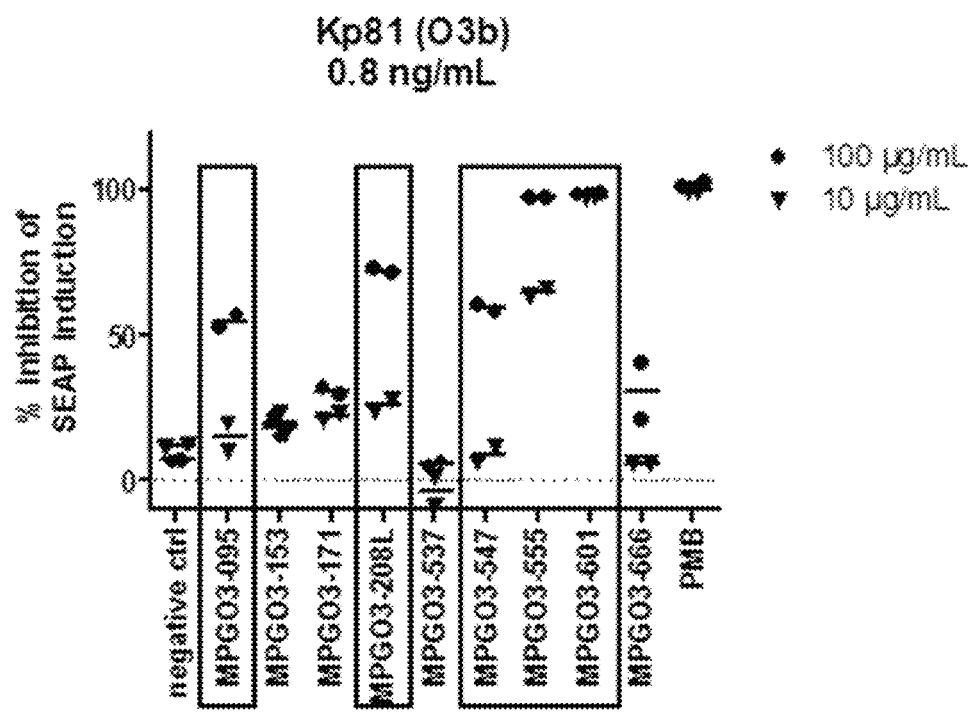

FIG. 7: Selection of 5 mAbs based on their reactivity determined in immunoblot with purified LPS from O3-group or O5 K. pneumoniae strains and based on neutralization of O3b LPS determined in vitro.

DETAILED DESCRIPTION

The term "antibody" as used herein shall refer to polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization e.g., to modify the antigen binding properties or any other property, such as stability or functional properties, such as binding to the Fc receptors FcRn and/or Fc gamma receptor.

The antibody as used herein has a specific binding site to bind one or more antigens or one or more epitopes of such antigens, specifically comprising a CDR binding site of a single variable antibody domain, such as VH, VL or VHH, or a binding site of pairs of variable antibody domains, such as a VL/VH pair, an antibody comprising a VL/VH domain pair and constant antibody domains, such as Fab, F(ab'), (Fab)$_2$, scFv, Fv, or a full length antibody.

The term "antibody" as used herein shall particularly refer to antibody formats comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)$_2$, scFv, Fd, Fv, or a full-length antibody e.g., of an IgG (e.g., an IgG1, IgG2, IgG3, or IgG4 subclass), IgA (e.g. an IgA1 or IgA2 subclass), IgD, IgE, or IgM isotype antibody. The term "full length antibody" can be used to refer to any antibody molecule comprising at least most of the Fc domain and other domains commonly found in a naturally occurring antibody monomer. This phrase is used herein to emphasize that a particular antibody molecule is not an antibody fragment.

The term "antibody" shall specifically include antibodies in the isolated form, which are substantially free of other antibodies directed against different target antigens or comprising a different structural arrangement of antibody domains. Still, an isolated antibody may be comprised in a combination preparation, containing a combination of the isolated antibody e.g., with at least one other antibody, such as monoclonal antibodies or antibody fragments having different specificities.

The term "antibody" shall apply to antibodies of animal origin, including human species, such as mammalian, including human, murine, rabbit, goat, lama, cow and horse, or avian, such as hen, which term shall particularly include recombinant antibodies which are based on a sequence of animal origin e.g., human sequences.

The term "antibody" further applies to chimeric antibodies with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "antibody" may further apply to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified e.g., by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "antibody" further applies to human antibodies.

The term "human" as used with respect to an antibody, is understood to include antibodies having variable and constant regions derived from human germline immunoglobulin sequences. The human antibody of the invention may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin genes or derived from human B cells by immunoglobulin gene cloning and recombinant antibody expression or from immortalized human B cell lines.

The term "fully human antibody" as used herein refers to a human antibody, which is composed of only human parts, in particular human CDR, human FR, and human constant regions, each originating from a human source, e.g. cells expressing human antibody sequences, libraries displaying human antibody sequences, or genes encoding human antibody sequences. Fully human antibodies may be naturally-occurring antibodies or artificial antibodies, which are understood as being composed of parts, each obtained from a different origin, thus, not occurring in nature. Exemplary artificial fully human antibodies are human switch variants of human antibodies, wherein at least one constant region is obtained from a human antibody of a different isotype.

The term "antibody" specifically applies to antibodies of any isotype or subclass. Depending on the amino acid sequence of the constant domain of their heavy chains, antibodies can be assigned to the major classes of antibodies IgA, IgD, IgE, IgG, and IgM, and several of these may be further divided into subclasses, e.g., IgG1, IgG2, IgG3, IgG4, IgA1, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals e.g., mammalians including human, that comprises genes or sequences from different origin e.g., murine, chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing or fusing antibody gene sequences to other DNA sequences.

It is understood that the term "antibody" also refers to derivatives of an antibody, in particular functionally active derivatives. An antibody derivative is understood as any combination of one or more antibody domains or antibodies and/or a fusion protein, in which any domain of the antibody may be fused at any position of one or more other proteins, such as other antibodies e.g., a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulphide bonding etc. The other substances bound to the antibody may be lipids, carbohydrates, nucleic acids, organic and inorganic molecules or any combination thereof (e.g., PEG, prodrugs or drugs). In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the antibody to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself e.g., radioisotope labels or fluorescent labels, or, in the case of an enzymatic label, may catalyze chemical alteration of a substrate compound or composition which is detectable.

The preferred derivatives as described herein are functionally active with regard to the antigen binding, preferably which have a potency to combat *K. pneumoniae* e.g., as determined in an SBA, OPK or LAL assay, or to protect against bacterial challenge or to neutralize endotoxemia.

Specifically, an antibody derived from an antibody of the invention may comprise at least one or more of the CDR regions or CDR variants thereof being functionally active in differentially, selectively, or specifically binding to the O3 group antigens as compared to other antigens.

Antibodies derived from a parent antibody or antibody sequence, such as a parent CDR or FR sequence, are herein particularly understood as mutants or variants obtained by e.g., in silico or recombinant engineering or else by chemical derivatization or synthesis.

It is understood that the term "antibody" also refers to variants of an antibody, including antibodies with functionally active CDR variants of a parent CDR sequence, and functionally active variant antibodies of a parent antibody.

Specifically, an antibody derived from an antibody as described herein may comprise at least 3 CDRs of the heavy chain variable region and at least 3 CDRs of the light chain variable region, with at least one point mutation in at least one of the CDR or FR regions, or in the constant region of the HC or LC, being functionally active e.g., specifically binding the O3 group antigens.

The term "variant" shall particularly refer to antibodies, such as mutant antibodies or fragments of antibodies e.g., obtained by mutagenesis methods, in particular to delete, exchange, introduce inserts into a specific antibody amino acid sequence or region or chemically derivatize an amino acid sequence e.g., in the constant domains to engineer the antibody stability, effector function or half-life, or in the variable domains to improve antigen-binding properties e.g., by affinity maturation techniques available in the art. Any of the known mutagenesis methods may be employed, including point mutations at desired positions e.g., obtained by randomization techniques. In some cases positions are chosen randomly e.g., with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "variant" shall specifically encompass functionally active variants.

The term "functionally active variant" of a CDR sequence as used herein, is understood as a "functionally active CDR variant", and the "functionally active variant" of an antibody as used herein, is understood as "functionally active antibody variant". The functionally active variant means a sequence resulting from modification of this sequence (a parent antibody or a parent sequence) by insertion, deletion or substitution of one or more amino acids, or chemical derivatization of one or more amino acid residues in the amino acid sequence, or nucleotides within the nucleotide sequence, or at either or both of the distal ends of the sequence e.g., in a CDR sequence the N-terminal and/or C-terminal 1, 2, 3, or 4 amino acids, and/or the centric 1, 2, 3, or 4 amino acids (i.e. in the midst of the CDR sequence), and which modification does not affect, in particular impair, the activity of this sequence. In the case of a binding site having specificity to a selected target antigen, the functionally active variant of an antibody would still have the predetermined binding specificity, though this could be changed e.g., to change the fine specificity to a specific epitope, the affinity, the avidity, the Kon or Koff rate, etc. For example, an affinity matured antibody is specifically understood as a functionally active variant antibody. Hence, the modified CDR sequence in an affinity matured antibody is understood as a functionally active CDR variant.

For example, a CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids e.g., 1, 2, 3, 4 or 5 amino acids, or by addition or insertion of one to several amino acids e.g., 1, 2, 3, 4 or 5 amino acids, or by a chemical derivatization of one to several amino acids e.g., 1, 2, 3, 4 or 5 amino acids, or combination thereof.

Functionally active variants may be obtained e.g., by changing the sequence of a parent antibody e.g., an antibody comprising the same binding site as any of the antibodies listed in FIG. 1, but with modifications within an antibody region besides the binding site, or derived from such parent antibody by a modification within the binding site but that does not impair the antigen binding, and preferably would have substantially the same biological activity as the parent antibody or even an improved activity, including the ability to specifically or selectively bind the O3 group antigens.

In particular, the functionally active variants have a neutralizing potency, such as an endotoxin neutralization function in a LAL assay or in a TLR-4 reporter cell based assay e.g., with substantially the same biological activity, as determined by the specific binding assay or functional test to target *K. pneumoniae.*

The term "substantially the same" with regard to binding a target antigen or biological activity as used herein refers to the activity as indicated by substantially the same activity being at least 20%, at least 50%, at least 75%, at least 90% e.g., at least 100%, or at least 125%, or at least 150%, or at least 175%, or e.g., up to 200%, or even a higher activity as determined for the comparable or parent antibody.

Specifically, the functionally active variants of an antibody of the invention have the potency to bind each of the O3 group antigens, or the specificity or selectivity to preferentially bind to each of the O3 group antigens relative to other (non-mannan LPS or non-O3 group antigens) of *K. pneumoniae*. Preferred variants are not binding to other antigens of *K. pneumoniae*, with a $K_D$ value difference of at least 2 logs, preferably at least 3 logs, and further include endotoxin neutralization function in a LAL or TLR4 signaling assay, such as to achieve significant reduction of endotoxin activity relative to control samples not containing the antibody e.g., with substantially the same biological activity, as determined by the specific binding assay or functional test to target *K. pneumoniae*. The significant reduction of activity in functional in vitro assays typically means the reduction of at least 50%, preferably at least 60%, 70%, 80%, 90%, 95% or 98% up to complete reduction of about 100% (+/−1%).

In a preferred embodiment the functionally active variant of a parent antibody a) is a biologically active fragment of the antibody, the fragment comprising at least 50% of the sequence of the molecule, preferably at least 60%, at least 70%, at least 80%, at least 90%, or at least 95% and most preferably at least 97%, 98% or 99%;

b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the antibody or a functionally active variant thereof and additionally at least one amino acid or nucleotide heterologous to the polypeptide or the nucleotide sequence.

In one preferred embodiment of the invention, the functionally active variant of the antibody as described herein is essentially identical to the variant described above, but differs from its polypeptide or the nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence e.g., by one or more point mutations, wherein the sequence alterations retains or improves a function of the unaltered polypeptide or the nucleotide sequence, when used in combination of the invention. Such sequence alterations can include, but are not limited to, (conservative) substitutions, additions, deletions, mutations and insertions.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;

Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the antibody sequences and homologs described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "antigen-binding site" or "binding site" refers to the part of an antibody that participates in antigen binding. The antigen binding site is formed by amino acid residues of the N-terminal variable ("V") regions of the heavy ("H") and/or light ("L") chains, or the variable domains thereof. Three highly divergent stretches within the V regions of the heavy and light chains, referred to as "hypervariable regions", are interposed between more conserved flanking stretches known as framework regions, The antigen-binding site provides for a surface that is complementary to the three-dimensional surface of a bound epitope or antigen, and the hypervariable regions are referred to as "complementarity-determining regions", or "CDRs." The binding site incorporated in the CDRs is herein also called "CDR binding site".

The term "antigen" as used herein interchangeably with the terms "target" or "target antigen" shall refer to a whole target molecule or a fragment of such molecule recognized by an antibody binding site. Specifically, substructures of an antigen e.g., a polypeptide or carbohydrate structure, generally referred to as "epitopes" e.g., B-cell epitopes or T-cell epitope, which are immunologically relevant, may be recognized by such binding site. Specific antigens like the various O3-antigens comprise carbohydrate (mannan) structures and may be provided as isolated antigens optionally provided on an artificial carrier, or else in the form of K. pneumoniae cells expressing the antigens or cell fractions thereof.

The term "epitope" as used herein shall in particular refer to a molecular structure which may completely make up a specific binding partner or be part of a specific binding partner to a binding site of an antibody. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping.

Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen.

Herein the term "epitope" shall particularly refer to the single epitope recognized by an antibody, or a cross-reactive epitope which is shared by at least two different antigens and optionally recognized by the cross-reactive antibody.

The term "expression" is understood in the following way. Nucleic acid molecules containing a desired coding sequence of an expression product such as e.g., an antibody as described herein, and control sequences such as e.g., a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions e.g., for the expression of a protein coded for by foreign DNA carried by the vector and introduced to the host cell.

Coding DNA is a DNA sequence that encodes a particular amino acid sequence for a particular polypeptide or protein such as e.g., an antibody. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host e.g., antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g., an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g., a foreign gene) can be introduced into a host cell, so as to transform the host and promote expression (e.g., transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those which are not naturally occurring e.g., codon-optimized nucleic acids or cDNA, or chemically synthesized.

Likewise, the isolated antibody of the invention is specifically non-naturally occurring e.g., as provided in a combination preparation with another antibody or active agent, which combination does not occur in nature, or an optimized or affinity—maturated variant of a naturally occurring antibody, or an antibody with a framework-region which is engineered to improve the manufacturability of the antibody. By such optimizing or engineering the antibody comprises one or more synthetic sequences or characteristics, which would not be found in the context of the antibody in nature.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated antibodies or epitopes of the invention, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy. In particular, the isolated antibody of the invention differs from polyclonal serum preparations raised against *K. pneumoniae* strains, because it is provided in the isolated and purified form, preferably provided in a preparation comprising the isolated antibody as the only active substance. This does not preclude, however, that the isolated antibody is provided in a combination product comprising a limited number of further well-defined (isolated) antibodies. Isolated antibodies may as well be provided on a solid, semi-liquid or liquid carrier, such as beads.

The term "neutralizing" or "neutralization" is used herein in the broadest sense and refers to any molecule that inhibits a pathogen, such as *K. pneumoniae* from infecting a subject, or to inhibit the pathogen from promoting infections by producing endotoxins, or to inhibit the endotoxins from exerting their biological activity, irrespective of the mechanism by which neutralization is achieved. Neutralization can be achieved, e.g., by an antibody that inhibits the colonization by *K. pneumoniae* of mucosal surfaces, invasion to sterile body sites, and eliciting adverse biological signals (in worst case inducing septic shock) in the host.

In the strict sense neutralization means, inhibiting the binding of specific LPS to its cognate receptor (e.g., Toll-like receptor-4 complex) and hence eliciting biological activity. This neutralization potency is typically determined in a standard assay e.g., an in vitro or in vivo neutralization assay e.g., a LAL test, or TLR-4 based assays, where the inhibition of endotoxin's biological activity is measured e.g., by colorimetry.

Antibodies combating or neutralizing *K. pneumoniae* are interfering with the pathogens and pathogenic reactions, thus able to limit or prevent infection and/or to ameliorate a disease condition resulting from such infection, or to inhibit *K. pneumoniae* pathogenesis, in particular dissemination and replication into or within sterile body compartments/sites of the host. In this regard the neutralizing antibody is also understood as being a "protective antibody" meaning that the antibody is responsible for immunity to an infectious agent observed in active or passive immunity. In particular, neutralizing or protective antibodies as described herein are possibly used for therapeutic purposes e.g., for prophylaxis or therapy, to prevent, ameliorate, treat or at least partially arrest disease symptoms, side effects or progression of disease induced by a pathogen. Specifically, protective antibodies are able to kill or impede replication of live *K. pneumoniae* cells by e.g., inducing serum bactericidal or opsonophagocytic activities, or remove whole bacterial cells or the LPS molecules thereof from the sterile body sites following therapeutic applications (i.e. given on an established infection). Alternatively, prophylactically applied protective antibodies inhibit establishment of an infection (i.e. spread of *K. pneumoniae* from non-sterile sites to sterile body compartments) by one of the abovementioned or other mechanisms.

The "cross-neutralization" property of the antibody as described herein is understood as covering not only *K. pneumoniae* of each of the O3 group antigens, in particular neutralizing one or more strains of each of the O3b, O3a, and O3 serotypes.

The term "O3 group" as used herein with respect to *K. pneumoniae* strains, antigens, or epitopes, shall mean the group of O3b, O3a, and O3, in particular the material originating from *K. pneumoniae* which is characterized by the respective serotype and antigenic structure. O3 group antigens are herein also referred to as "O3-antigens".

The term "O3b-antigen" also referred to as "O3b-type" as used herein shall refer to the (methyl phosphate containing) carbohydrate structure of the LPS O-antigen of *K. pneumoniae* depicted in Formula (I), in particular comprising a mannan polymer and a structure comprising at least one of the trimannose repeating unit included in Formula (I). Such structure and the trimannose repeating unit has heretofore not been identified. The structure is similar, but distinct from that of the O3a-antigen (Formula (II)) or O3-antigen (Formula (III)). It is thus, surprising, that the newly identified O3b-structure comprises a distinct epitope.

Of note, the same kind of mannan-structure and cross-reactive epitope structure may also be expressed by organisms other than *K. pneumoniae* or respective cells, thus, can be a target of interest when combating diseases mediated by such organisms or cells.

Antibodies specifically recognizing the pentamannose structure of the O3-antigen were previously found not to recognize the O3a-antigen (tetramannose structure). The minimum number of mannose residues needed to define the O3a and O3 polysaccharide was described in the prior art to be four, and the shortest candidate for an antibody epitope was found to be the tetramannan (see (7)). O3b is herein understood as a new serotype determinant, which is similar, but distinct from the O3a or O3 serotype that is characterized by the presence of the other O3-antigens and the absence of the O3b (trimannose) structure.

The respective O-antigen comprising the O3b structure is herein referred to as "O3b-antigen" which includes the "O3b-epitope" being recognized by a O3b-specific antibody of the invention. The O3b-antigen is understood as the outer part of the LPS of *K. pneumoniae* of the O3b O-type, which is the surface accessible antigenic carbohydrate structure comprising one or more specific O3b-epitopes incorporated therein.

Any *K. pneumoniae* which is characterized by a LPS O-antigen comprising at least one O3b structure is herein referred to as *K. pneumoniae* of the O3b-type. LPS of *K. pneumoniae* of the O3b-type may comprise the O3b structure, or both, O3b and O3a and/or O3 structures.

The O3a-antigen is understood as the outer part of the LPS of *K. pneumoniae* of the O3a-type, which is the surface accessible antigenic carbohydrate structure comprising one or more specific O3a-epitopes incorporated therein, and which does not include any O3b-structure.

The O3-antigen is understood as the outer part of the LPS of *K. pneumoniae* of the O3-type, which is the surface accessible antigenic carbohydrate structure comprising one or more specific O3-epitopes incorporated therein, and which does not include any O3b-structure or O3a-structure.

The term "pan-O3" with respect to target antigens recognized by a "pan-O3-antibody" as used herein shall refer to all of the O3b-antigen, the O3a-antigen and the O3 antigen, and the cross-reactive, yet O3-specific, antibody recognizing each of the O3b-antigen, the O3a-antigen and the O3 antigen.

"Specific" binding, recognizing or targeting as used herein, means that the binder e.g., antibody or antigen-binding portion thereof, exhibits appreciable affinity for the target antigen or a respective epitope in a heterogeneous population of molecules. Thus, under designated conditions (e.g., immunoassay), a binder specifically binds to the target O3b antigen and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10-fold different (understood as at least 1 log difference), preferably the difference is at least 100-fold (understood as at least 2 logs difference), and more preferred a least 1000-fold (understood as at least 3 logs difference) as compared to another target.

The term "specificity" is also understood to apply to binders which bind to one or more molecules e.g., cross-specific binders. Preferred cross-specific (also called poly-specific or cross-reactive) binders targeting at least two different targets or epitopes or nucleotide sequences of such targets or targeting a cross-reactive epitope or nucleotide sequence on at least two different targets, specifically bind the targets with substantially similar binding affinity e.g., with less than 100-fold difference or even less than 10-fold difference, or, with substantially different binding affinity e.g., with at least 10 fold or at least 100 fold difference.

The cross-specific binder which recognizes each of the O3 group antigens may bind to each of the antigens with substantially equal affinities or may preferentially bind one or two targets over the other(s) with a differential binding affinity to preferentially bind one antigen relative to another one which e.g., is more than equal e.g., at least 1.5 fold, or at least 2-fold, or at least 3-fold, or at least 4-fold, or at least 5 fold, or at least 6-fold, or at least 7-fold, or at least 8-fold, or at least 9-fold, or at least 10-fold higher. Such equal or differential binding may be determined by an immunoassay, preferably immunoblotting, ELISA or other immunological methods.

Preferred antibodies as described herein are binding each of the O3 group antigens, with a high affinity, in particular with a high on and/or a low off rate, or a high avidity of binding (avid binding affinity). The binding affinity of an antibody is usually characterized in terms of the concentration of the antibody, at which half of the antigen binding sites are occupied, known as the dissociation constant (Kd, or $K_D$). Usually a binder is considered a high affinity binder with a $K_D<10^{-6}$ M or $K_D<10^{-7}$ M as determined using a monovalent binder or bivalent binder, in some cases e.g., for therapeutic purposes higher affinities e.g., with a $K_D<10^{-8}$ M or even a $K_D<10^{-9}$ M (as determined using a monovalent binder), or $K_D<10^{-9}$ M, or even a $K_D<10^{-10}$ M (as determined using a bivalent binder).

Yet, in a particularly preferred embodiment the individual antigen binding affinities are of medium affinity e.g., with a $K_D$ higher than $10^{-6}$ e.g., such as the avid binding affinity (as determined using a bivalent binder).

Medium affinity binders may be provided and affinity matured, if necessary.

Affinity maturation is the process by which antibodies with increased affinity for a target antigen are produced. Any one or more methods of preparing and/or using affinity maturation libraries available in the art may be employed in order to generate affinity matured antibodies in accordance with various embodiments of the invention disclosed herein. Exemplary such affinity maturation methods and uses, such as random mutagenesis, bacterial mutator strains passaging, site-directed mutagenesis, mutational hotspots targeting, parsimonious mutagenesis, antibody shuffling, light chain shuffling, heavy chain shuffling, CDR1 and/or CDR1 mutagenesis, and methods of producing and using affinity maturation libraries amenable to implementing methods and uses in accordance with various embodiments of the invention disclosed herein, include, for example, those disclosed in: Prassler et al. (2009); Immunotherapy, Vol. 1(4), pp. 571-583; Sheedy et al. (2007), Biotechnol. Adv., Vol. 25(4), pp. 333-352; WO2012/009568; WO2009/036379; WO2010/105256; US2002/0177170; WO2003/074679.

With structural changes of an antibody, including amino acid mutagenesis or as a consequence of somatic mutation in immunoglobulin gene segments, variants of a binding site to an antigen are produced and selected for greater affinities. Affinity matured antibodies may exhibit a several logfold greater affinity than a parent antibody. Single parent antibodies may be subject to affinity maturation. Alternatively pools of antibodies with similar binding affinity to the target antigen may be considered as parent structures that are varied to obtain affinity matured single antibodies or affinity matured pools of such antibodies.

The preferred affinity matured variant of an antibody as described herein exhibits at least a 2-fold increase in affinity of binding, preferably at least a 5, preferably at least 10, preferably at least 50, or preferably at least 100-fold increase. The affinity maturation may be employed in the course of the selection campaigns employing respective libraries of parent molecules, either with antibodies having medium binding affinity to obtain the antibody of the invention having the specific target binding property of a binding affinity $K_D < 10^{-9}$ M (e.g., avid binding affinity as determined using a bivalent binder). Alternatively, the affinity (e.g., avid binding affinity as determined using a bivalent binder) may be even more increased by affinity maturation of the antibody according to the invention to obtain the high values corresponding to a $K_D$ of less than $10^{-9}$ M, preferably less than $10^{-10}$ M or even less than $10^{-11}$ M, most preferred in the picomolar range.

In certain embodiments binding affinity is determined by an affinity ELISA assay. In certain embodiments binding affinity is determined by a BIAcore, BLI, ForteBio or MSD assays. In certain embodiments binding affinity is determined by a kinetic method. In certain embodiments binding affinity is determined by an equilibrium/solution method.

Use of the term "having the same specificity", "having the same binding site" or "binding the same epitope" indicates that equivalent monoclonal antibodies exhibit the same or essentially the same, i.e. similar immunoreaction (binding) characteristics and compete for binding to a pre-selected target binding sequence. The relative specificity of an antibody molecule for a particular target can be relatively determined by competition assays e.g., as described in Harlow, et al., ANTIBODIES: A LABORATORY MANUAL, Cold Spring Harbor Laboratory Press, Cold Spring Harbor, N.Y., 1988).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "compete" with each other for binding of their respective epitope(s). Antibodies that compete with any of the exemplified antibodies for binding any or each of the O3 group antigens are particularly encompassed by the present invention.

"Competitively binding" or "competition" herein means a greater relative inhibition than about 30%, e.g., as determined by competition ELISA analysis or by biolayer interferometry (BLI) analysis.

Specifically, the avid binding affinity targeting any of the O3 group antigens (incorporating the cross-reactive epitope) is measured by BLI using a fortéBIO Octet Red instrument (ForteBio analysis) (e.g., Pall Life Sciences), such as exemplified herein.

It may be desirable to set a higher threshold of relative inhibition as criteria of what is a suitable level of competition in a particular context e.g., where the competition analysis is used to select or screen for new antibodies designed with the intended function of the binding of the antigen. Thus, for example, it is possible to set criteria for the competitive binding, wherein at least 40% relative inhibition is detected, or at least 50%, at least 60%, at least 70%, at least 80%, at least 90% or even at least 100%, before an antibody is considered sufficiently competitive.

The term "*K. pneumoniae* infection" and "*K. pneumoniae* colonization" is understood in the following way: *Klebsiella pneumoniae* is a Gram-negative, bacterium that is a member of the family Enterobacteriaceae. It is a ubiquitous bacterium, which can also colonize the human host, typically in the intestines or the upper airways. Being an opportunistic pathogen, from these sites it can invade sterile body sites in case not properly controlled by the immune system. Uncontrolled bacterial replication at these sites will induce inflammation, in a great part, mediated by the endotoxin (i.e. LPS) molecules released from *K. pneumoniae*. In case of bacteremia, endotoxin molecules may trigger septic shock.

*K. pneumoniae* colonization means that the subject has a sufficiently high concentration of *K. pneumoniae* bacteria at a site that they can be detected, yet the bacteria are causing no signs or symptoms. Colonization can persist for a long period of time, with resolution influenced by the immune response to the organism, competition at the site from other organisms and, sometimes, use of antimicrobials.

In general, bacteremia caused by *K. pneumoniae* may be successfully treated with known conventional antibacterial therapy, such as treatment with antibiotics, steroid and non-steroid inhibitors of inflammation. The present invention provides for a new immunotherapy, employing antibodies specifically recognizing *K. pneumoniae*, which is optionally combined with anti-bacterial or anti-inflammatory therapy. Exemplary antibiotics used for treating patients with *K. pneumoniae* infection are aminoglycosides, cephalosporines, aminopenicilines, carbapenems, fluoroquinolons, tygecycline, colistin, etc.

Multi-drug resistant (MDR) *K. pneumoniae* is particularly understood as those strains demonstrating resistance to three or more classes of antibiotics e.g., the following agents/groups: penicillins, cephalosporins, carbapenems, aminoglycosides, tetracyclines, fluoroquinolones, nitrofurantoin, trimethoprim (and its combinations), fosfomycin, polymixins, chloramphenicol, azthreonam, or tigecycline.

With the recent emergence of antibiotic-resistant strains, treating bacteremia of this nature has become significantly more difficult. Patients who develop *K. pneumoniae* disease have longer hospital and ICU stays, high mortality, and greater health care costs than patients without *K. pneumoniae* disease. Patient care may be improved and nosocomial infections may be reduced by preventing, rather than treating, *K. pneumoniae* disease prophylaxis when a patient is heavily colonized by *K. pneumoniae*.

*K. pneumoniae* disease is specifically understood as a disease caused by *K. pneumoniae* infection. Such diseases include local and systemic disease. Severe cases of disease are e.g., primary and secondary bacteremia, pneumonia, urinary tract infection, liver abscess, peritonitis, or meningitis.

The term "recombinant" as used herein shall mean "being prepared by or the result of genetic engineering". A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody e.g., from a transfectoma, (c) antibodies isolated from a recombinant, combinatorial human antibody library or library of antigen-binding sequences of an antibody, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

Selective binding can be further improved by recombinant antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

The term "subject" as used herein shall refer to a warm-blooded mammalian, particularly a human being or a non-human animal. *K. pneumoniae* is a critically important human pathogen that is also an emerging concern in veterinary medicine. It is present in a wide range of non-human animal species. Thus, the term "subject" may also particularly refer to animals including dogs, cats, rabbits, horses, cattle, pigs and poultry. In particular the medical use of the invention or the respective method of treatment applies to a subject in need of prophylaxis or treatment of a disease condition associated with a *K. pneumoniae* infection. The subject may be a patient at risk of a *K. pneumoniae* infection or suffering from disease, including early stage or late stage disease. The term "patient" includes human and other mammalian subjects that receive either prophylactic or therapeutic treatment. The term "treatment" is thus meant to include both prophylactic and therapeutic treatment.

A subject is e.g., treated for prophylaxis or therapy of *K. pneumoniae* disease conditions. In particular, the subject is treated, which is either at risk of infection or developing such disease or disease recurrence, or a subject that is suffering from such infection and/or disease associated with such infection.

Specifically the term "prophylaxis" refers to preventive measures which is intended to encompass prevention of the onset of pathogenesis or prophylactic measures to reduce the risk of pathogenesis.

Specifically, the treatment may be by interfering with the pathogenesis of *K. pneumoniae* as causal agent of the condition, The term "substantially pure" or "purified" as used herein shall refer to a preparation comprising at least 50% (w/w), preferably at least 60%, 70%, 80%, 90% or 95% of a compound, such as a nucleic acid molecule or an antibody. Purity is measured by methods appropriate for the compound (e.g., chromatographic methods, polyacrylamide gel electrophoresis, HPLC analysis, and the like).

The term "therapeutically effective amount", used herein interchangeably with any of the terms "effective amount" or "sufficient amount" of a compound e.g., an antibody of the present invention, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from an inhibition of *K. pneumoniae* pathogenesis, for example, adhesion and colonization of mucosal surfaces, uncontrolled replication within sterile body sites, and toxicity of host cells by bacterial products.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

A therapeutically effective amount of the antibody as described herein, such as provided to a human patient in need thereof, may specifically be in the range of 0.5-50 mg/kg, preferably 5-40 mg/kg, even more preferred up to 20 mg/kg, up to 10 mg/kg, up to 5 mg/kg, though higher doses may be indicated e.g., for treating acute disease conditions. The dose can be much lower if a highly potent antibody is used. In such case, the effective amount may be in the range of 0.005 to 5 mg/kg, preferably 0.05 to 1 mg/kg.

Moreover, a treatment or prevention regime of a subject with a therapeutically effective amount of the antibody of the present invention may consist of a single administration, or alternatively comprise a series of applications. For example, the antibody may be administered at least once a year, at least once a half-year or at least once a month. However, in another embodiment, the antibody may be administered to the subject from about one time per week to about a daily administration for a given treatment. The length of the antibody treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

Monoclonal antibodies highly specific to any of the O3 group antigens, and in particular the pan-O3 antibodies, have great potential for the prophylaxis (e.g., for high risk groups) and treatment of *K. pneumoniae* infections. Doses for prophylactic treatment are typically in the lower range (e.g. at least 0.005 mg/kg and less than 1 mg/kg), and specifically administered once, e.g. when a subject is identified as being immunocompromised or immunosuppressed and/or at risk of getting in contact with *K. pneumoniae*, or by a long-term treatment schedule, e.g. at least 2, 3, 4, 5, 6, 7, 8, 9, 10, 11, or 12 doses annually or half-annually. Doses for therapeutic treatment are typically administered in the acute or chronic phase of disease and typically in the higher range (e.g. at least 0.05 or 0.5 mg/kg and less than 10 mg/kg), and specifically administered until cure of the disease, by one or more administrations, e.g. in regular intervals, such as at least 1, 2, 3, or 4 administrations daily, or at least 1, 2, 3, 4, 5, or 6 administrations weekly, or at least 1, 2, 3, or 4 administrations monthly.

The O3 serogroup used to be considered a single uniform structure, however, it actually comprises three different subtypes, which differ in the number of mannose residues within the repeating units.

These alterations in the structure represent antigenic differences as proven by the reactivity pattern of monoclonal antibodies specific to the O3 serogroup. Selection of monoclonal antibodies cross-reacting with all three different serotypes within the O3 serogroup can be of high importance with respect to putative product development. Furthermore demonstration of relevant modes-of-action of cross-reactive mAbs renders them potential therapeutic options. Antibodies cross-reacting between O3, O3a and O3b can be valuable means for immunotherapy. The O3 cross-reactive (pan-O3 reactive) mAb is specific to almost a quarter (23.2%) of all *Klebsiella* isolates, and hence further development of such mAbs as therapeutic product candidate may be justified.

Once antibodies with the desired binding properties are identified, such antibodies, including antibody fragments can be produced by methods well-known in the art, including, for example, hybridoma techniques or recombinant DNA technology.

Recombinant monoclonal antibodies can, for example, be produced by isolating the DNA encoding the required antibody chains and transfecting a recombinant host cell with the coding sequences for expression, using well known recombinant expression vectors, e.g., the plasmids of the invention or expression cassette(s) comprising the nucleotide sequences encoding the antibody sequences. Recombinant host cells can be prokaryotic and eukaryotic cells, such as those described above.

According to a specific aspect, the nucleotide sequence may be used for genetic manipulation to obtain antibodies containing artificial sequences, e.g. to improve the affinity, or other characteristics of the antibody. For example, the constant region may be engineered to more nearly resemble human constant regions to avoid immune response, if the antibody is used in clinical trials and treatments in humans. It may be desirable to genetically manipulate the antibody sequence to obtain greater affinity to the O3b target and greater efficacy against *Klebsiella pneumoniae*. It will be apparent to one of skill in the art that one or more polynucleotide changes can be made to the antibody and still maintain its binding ability to the target O3b-antigen.

The production of antibody molecules, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al., (1999, Biochim Biophys Acta 1430(2):191-202) and Lee and Kwak (2003, J. Biotechnology 101:189-198) describe the production of monoclonal antibodies from separately produced heavy and light chains, using plasmids expressed in separate cultures of host cells. Various other techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

If desired, the antibody as described herein, e.g., any of the mAbs referred to in the examples or listed in FIG. 1 or 2, or a functional variant thereof, may be sequenced and the polynucleotide sequence may then be cloned into a vector for expression or propagation. The sequence encoding the antibody may be maintained in vector in a host cell and the host cell can then be expanded and frozen for future use. Production of recombinant monoclonal antibodies in cell culture can be carried out through cloning of antibody genes from B cells by means known in the art.

In another aspect, there is provided an isolated nucleic acid comprising a sequence that codes for production of the recombinant antibody as described herein.

An antibody encoding nucleic acid can have any suitable characteristics and comprise any suitable features or combinations thereof. Thus, for example, an antibody encoding nucleic acid may be in the form of DNA, RNA, or a hybrid thereof, and may include non-naturally-occurring bases, a modified backbone, e.g., a phosphorothioate backbone that promotes stability of the nucleic acid, or both. The nucleic acid advantageously may be incorporated in an expression cassette, vector or plasmid of the invention, comprising features that promote desired expression, replication, and/or selection in target host cell(s). Examples of such features include an origin of replication component, a selection gene component, a promoter component, an enhancer element component, a polyadenylation sequence component, a termination component, and the like, numerous suitable examples of which are known.

The present disclosure further provides the recombinant DNA constructs comprising one or more of the nucleotide sequences described herein. These recombinant constructs are used in connection with a vector, such as a plasmid, phagemid, phage or viral vector, into which a DNA molecule encoding any disclosed antibody is inserted.

Monoclonal antibodies are produced using any method that produces antibody molecules by cell lines in culture e.g., cultivating recombinant eukaryotic (mammalian or insect) or prokaryotic (bacterial) host cells. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

Antibodies as described herein may be identified or obtained employing a hybridoma method or by direct amplification, cloning and recombinant expression of immunoglobulin genes from single B cells including e.g. a screening method as exemplified herein using a certain antigen. In such hybridoma method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells or of cells producing recombinant antibodies are growing is assayed for production of monoclonal antibodies directed against the antigen. Preferably, the binding specificity of monoclonal antibodies produced by hybridoma cells or by cells producing the antibody recombinantly is determined by immunoprecipitation or by an in vitro binding assay, such as radioimmunoassay (RIA) or enzyme-linked immunoabsorbent assay (ELISA).

mAbs may then be purified from hybridoma supernatants and culture supernatants from cells producing recombinant antibodies for further testing for its specific binding of any of the O3 group antigens and possibly for cross-reactivity, and in particular for (substantially) equal or differential binding affinity to preferentially bind any one or two of the O3 group antigens over other(s), and antibodies may be engineered e.g., for different diagnostic or therapeutic purposes.

Cross-reactive O3 group antigen-specific antibodies, in some instances, emerge through screening against any one of the single O3b, O3a, or O3 antigens. To increase the likelihood of isolating differentially binding clones one would apply multiple selective pressures by processively screening against the different antigens. Special mAb selection strategies employ each of the O3b and O3a or O3 components or other *K. pneumoniae* antigens in an alternating fashion.

Screening methods for identifying antibodies with the desired selective binding properties may be done by display technologies using a library displaying antibody sequences or antigen-binding sequences thereof (e.g., using phage, bacterial, yeast or mammalian cells; or in vitro display systems translating nucleic acid information into respective (poly)peptides). Reactivity can be assessed based on ELISA, Immunoblotting or surface staining with flow cytometry e.g., using standard assays.

Isolated antigen(s) may e.g., be used for selecting antibodies from an antibody library e.g., a yeast-displayed antibody library.

The invention moreover provides a pharmaceutical composition which comprises an antibody as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well known in the art.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination provided by the invention. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be e.g., admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g., REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an antibody as described herein and one or more therapeutically active agents are formulated. Stable formulations of the antibody as described herein are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. The antibody and other therapeutically active agents disclosed herein may also be formulated as immunoliposomes, and/or entrapped in microcapsules.

Administration of the pharmaceutical composition comprising an antibody as described herein, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary e.g., employing inhalable technology or pulmonary delivery systems, vaginally, parenterally, rectally, or intraocularly.

Exemplary formulations as used for parenteral administration include those suitable for subcutaneous, intramuscular or intravenous injection as, for example, a sterile solution, emulsion or suspension.

In one embodiment, the antibody as described herein is the only therapeutically active agent administered to a subject e.g., as a disease modifying or preventing monotherapy.

In another embodiment, the antibody as described herein is combined with further antibodies in a cocktail e.g., combined in a mixture or kit of parts, to target *Klebsiella pneumoniae*, such that the cocktail contains more than one therapeutically active agents administered to a subject e.g., as a disease modifying or preventing combination therapy.

Further, the antibody as described herein may be administered in combination with one or more other therapeutic or prophylactic agents, including but not limited to standard treatment e.g., antibiotics, steroid and non-steroid inhibitors of inflammation, and/or other antibody based therapy e.g., employing anti-bacterial or anti-inflammatory agents.

A combination therapy is particularly employing a standard regimen e.g., as used for treating infection by *Klebsiella pneumoniae*. This may include antibiotics, e.g., tygecycline, colistin, polymixin B, and beta lactams with or without non-beta lactam inhibitors.

In a combination therapy, the antibody may be administered as a mixture, or concomitantly with one or more other therapeutic regimens e.g., either before, simultaneously or after concomitant therapy.

The biological properties of the antibody or the respective pharmaceutical preparations as described herein may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knock-ins and knockouts). Such experimentation may provide meaningful data for determination of the potential of the antibody to be used as a therapeutic or as a prophylactic with the appropriate half-life, effector function, (cross-) neutralizing activity and/or immune response upon active or passive immunotherapy. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the antibody and respective pharmaceutical compositions as described herein may be tested in humans to determine their therapeutic or prophylactic efficacy, toxicity, immunogenicity, pharmacokinetics, and/or other clinical properties.

In specific cases the patient is an immunocompromised patient. Some immunocompromised patients may suffer from a primary immunodeficiency or a secondary (acquired) immunodeficiency. Some immunocompromised patients are being or have been treated with an immunosuppressive therapy or with a chemotherapeutic agent. Some immunocompromised patients are transplant patient.

Immunocompromised patients likely suffer from a phagocytic disorder, such as characterized by a lower phagocytic number and/or impaired function.

The following disorders can cause impaired or lost phagocytotic activities:

Primary immunodeficiency of phagocytes:
1. Chronic neutropenia:
   a. Cyclic neutropenia
   b. Severe congenital neutropenia
   c. Shwachman-Diamond syndrome
2. Leukocyte adhesion deficiency
   a. Type 1
   b. Type 2
   c. Rac 2 deficiency
3. Defects of signaling
   a. Interferon-γ and interleukin-12 defects
4. Defects of intracellular killing
   a. Chronic granulomatous disease of childhood
   b. Myeloperoxidase deficiency
   c. Chédiak-Higashi syndrome
   d. Neutrophil-specific granule deficiency Secondary immunodeficiency of phagocytes:
1. Neutropenia/granulocytopenia: reduced number of blood neutrophils/granulocytes (<1500 cells/ml)
   a. Bone marrow diseases (tumor infiltration, aplastic anaemia, hematologic malignancy, granulomatous disease, irradiation, myelofibrosis)
   b. Immune mediated neutropenia (drugs acting as hapten, autoimmune diseases)
   c. Infections (bacterial sepsis, malaria, toxoplasmosis, viral infections, like EBV, CMV, Influenza)
   d. Nutritional deficiency (malnutrition, B-12 deficiency)
   e. Drugs, chemicals (macrolids, procainamides, phenotiazid, sulfonamides, chloramphenicol, aminopyrine, anti-thyroid drugs, like thiouracil, methimazol, thiocyanate, heavy metals)
   f. Chemotherapy, immunosuppression (treatment of autoimmune diseases, after transplantation)
2. Phagocyte function/chemotaxis disorder or decreased ability to upregulate production of phagocytes
   a. Neonates (Under conditions of stress, neonatal PMNs do not function with normal phagocytic and microbicidal activities. PMNs isolated from the blood of term neonates display diminished chemotactic and adhesion capacities.
   b. Elderly (Decreased phagocytic ability, cytotoxicity, enzyme release, reduced adhesion
   c. Diabetes mellitus (lower killing by PMNs, monocyte/macrophage dysfunction, renal failure and cirrhosis
   d. Trisomy 21
   e. Surgery, trauma
   f. Corticosteroids
   g. HIV To identify patients with impaired phagocyte number and function, any suitable technique known by persons skilled in the art can be applied. These include but are not limited to complete blood count, differential white blood cell count, peripheral smear, measurement of adherence, chemotaxis, phagocytosis, intracellular killing of phagocytes, assays to measure specific neutrophil enzymes or detect autoantibodies against neutrophils.

The present invention is further illustrated by the following examples without being limited thereto.

EXAMPLES

Example 1

Figures 3A, 3B:
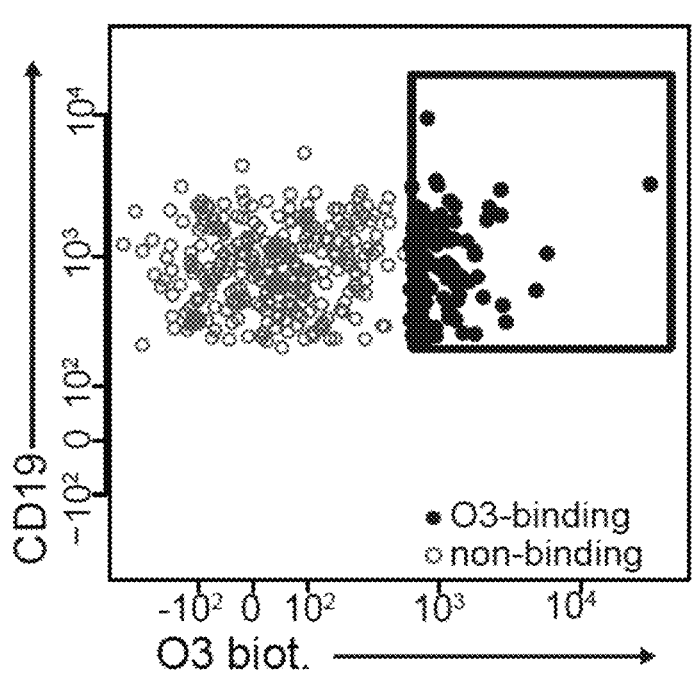

Generation of Fully Human Anti-*Klebsiella Pneumoniae* Lipopolysaccharide O3-Antigen Antibodies from Peripheral Memory and Intestinal Effector B Cells Methods 1. Isolation and Generation of Recombinant Fully Human *Klebsiella Pneumoniae* O-Antigen-Binding Antibodies O-antigen-binding B cells were identified by flow cytometry using fluorophore-conjugated Streptavidin to detect biotinylated O3-antigen, as shown in FIG. 3a, or from a O3 K-strain, which is bound by B cells from intestinal lamina propria Subsequently, single O-antigen-binding B cells were isolated using fluorescence-activated cell sorting.

1.1 Isolation of Lamina Propria Lymphocytes

Lamina propria lymphocytes (LPL) were directly isolated from human terminal ileum surgical samples. All cells were isolated from phenotypical healthy mucosa having at least 3 cm distance from tumor or inflamed area. Lamina mucosa and propria were dissected from lamina muscularis using forceps and scalpel. The tissue was extensively washed in PBS+ (1×PBS (Gibco), 2% FCS, 1× Antimycotic/Antibiotic (Gibco)) at room-temperature. The tissue was kept on ice throughout the process, except if otherwise stated. The tissue was cut into 3-5 mm pieces and remaining connective tissue was removed as extensively as possible. The tissue was transferred to a 50 ml centrifuge tube and washed 3-times with 1×PBS+ and subsequently incubated 2×15 min with PBS containing 1 mM Dithioerythriol in a bottle placed in a water bath at 37° C. under constant stirring to remove residual mucus. Subsequently the tissue was washed 3× with 1×PBS containing 0.5 mM EDTA, followed by 30 min incubation with 1×PBS containing 0.5 mM EDTA at 37° C. as described above to remove the epithelium. After washing with 1×PBS+ the tissue was digested using 1× PBS+ containing 0.2% (w/v) Dnasel and 0.5% (w/v) Collagenase D (both Roche) for 1 h under constant stirring at 37° C. LPL were isolated by a discontinuous Percoll gradient (40%/70% diluted in 1×PBS). To better discriminate the 40%/70% interface Phenol Red was added to the 70% dilution (1:1000; Gibco). 15 ml of each dilution were added into a 50 ml centrifuge tube and 20 ml cell suspension was slowly added onto the top of the gradient. After centrifugation, LPL were isolated from the 40%/70% interface by using a Pasteur pipet and added into a minimum of 25 ml RPMI into a new centrifuge tube. All subsequent steps were performed at 4° C. and on ice. Cells were centrifuged at 400 g for 10 min. The supernatant was discarded and the cells were washed in 10 ml ice-cold RPMI. The cells were counted using a Thoma chamber using a Trypan Blue counterstain (Gibco) and subsequently centrifuged at 400 g for 10 min. The supernatant was discarded and cells were further processed for flow cytometry or immediately frozen following the freezing protocol.

1.2 Isolation of Peripheral Blood Mononuclear Cells

As an alternative source, freshly drawn human peripheral blood can be used. According to a typical protocol, the human peripheral blood is e.g. diluted 1:1 with RPMI medium (Gibco) at room-temperature and slowly added onto 15 ml Ficoll (GE Healthcare) in a 50 ml centrifuge tube. The cells are spun for 40 min at room-temperature with the lowest acceleration and no break. Cells residing at the water/Ficoll interface are isolated using a Pasteur pipet and resuspended in a minimum of 25 ml RPMI at room-temperature in a 50 ml centrifuge tube. All subsequent steps are performed at 4° C. and on ice. Cells are centrifuged at 400 g for 10 min. The supernatant is discarded and the cells are washed in 10 ml ice-cold RPMI. The cells are counterstained using Trypan Blue (Gibco), counted using a Thoma chamber and subsequently centrifuged at 400 g for 10 min. The supernatant is discarded and cells are further processed for flow cytometry or immediately frozen following the freezing protocol.

1.3 Freezing of Mammalian Cells

Cells were counted and diluted with heat-inactivated FCS (Gibco) to reach a concentration of $1 \times 10^7$ cells/ml. FCS containing 20% (v/v) sterile DMSO suitable for cell culture (Sigma) was freshly prepared and 500 µl were added to 1.8 ml cryotubes (ThermoFisher). 500 µl cell suspension was added to reach a final concentration of $5 \times 10^6$ cells/ml and the vials were frozen at −80° C. using a Coolcell (Biocision).

1.4 Cell Staining for Flow Cytometry

Flow cytometry cell stainings were performed in 1.5 ml tubes using 1×PBS containing 2% FCS (FACS buffer) or Horizon stain buffer (BD) if more than one Brilliant violet dye was used. $5 \times 10^6$ Cells/ml were stained in 50 µl staining mix for 30 min at 4° C. in the dark using the following antibodies:

Mouse anti-human CD19-APC-H7 (BD), Mouse anti-human CD27-PE (BD), Mouse anti-human CD27-BV605 (BD), Mouse anti-human IgG BV510 (BD), Mouse anti-human IgG V450 (BD), Mouse anti-human IgA-PE (Miltenyi), Goat anti-human IgA-FITC (Life technologies), Mouse anti-human CD45-VioGreen (Miltenyi) and Mouse anti-human CD11b-PE-Cy7 (eBioscience). Dead cells were excluded by 7-AAD (Life technologies). Biotinylated O3-antigen fractions were used at a final concentration of 20 µg/ml and detected with 0.5 µg/ml Streptavidin-Alexa647 (Life technologies). Subsequently, 1 ml FACS buffer was added and the cells were spun for 5 min at 500 g at 4° C. The supernatant was discarded and the cells were washed in 1 ml FACS buffer and centrifuged again. The pellet was resuspended in 50 µl staining mix and cells were incubated 30 min at 4° C. in the dark. For washing 1 ml of FACS buffer was added before the centrifugation step. Supernatant was discarded and cells were resuspended in 1 ml FACS buffer prior to centrifugation. After supernatant removal the cells were diluted using FACS buffer (250-1000 µl) and filtered into a tube with a meshed cap (BD) before analysis or sorting.

1.5 Single O-Antigen Binding B Cell Sorting

Lamina propria plasmablasts were isolated as single, 7-AAD$^-$, CD19$^+$, CD45$^+$, O3-antigen$^+$. O3-antigen binding memory B cells can be identified as single, 7-AAD$^-$, CD19$^+$, CD27$^+$, O-antigen$^+$ cells. Single cells were sorted on Aria II instruments (BD) into 384-well PCR plates (4titude). After single cell sorting the plates were immediately frozen on dry ice and stored at −80° C. or directly processed.

1.6 Ig Gene Sequencing of Single Human B Cells

Full length Ig genes of single human B cells were obtained by the method described by Tiller et al modified by Murugan et al. (T. Tiller et al., Efficient generation of monoclonal antibodies from single human B cells by single cell RT-PCR and expression vector cloning. J. Immunol. Methods. 329, 112-24 (2008); R. Murugan, K. Imkeller, C. E. Busse, H. Wardemann, Direct high-throughput amplification and sequencing of immunoglobulin genes from single human B cells. Eur. J. Immunol. 45, 2698-700 (2015)). Full cDNA of single B cells was synthesized by reverse transcription in a 384-well cycler (Eppendorf). cDNA was transferred to a primary 384-well PCR plate. After the primary amplification step, the primary PCR product was transferred into secondary PCR mix. Primers used to amplify the full length Ig genes were previously published by others. (T. Tiller et al., Efficient generation of monoclonal antibodies from single human B cells by single cell RT-PCR and expression vector cloning. J. Immunol. Methods. 329, 112-24 (2008), R. Murugan, K. Imkeller, C. E. Busse, H. Wardemann, Direct high-throughput amplification and sequencing of immunoglobulin genes from single human B cells. Eur. J. Immunol. 45, 2698-700 (2015); H. Wardemann et al., Predominant autoantibody production by early human B cell precursors. Science. 301, 1374-7 (2003); J. Benckert et al., The majority of intestinal IgA+ and IgG+ plasmablasts in the human gut are antigen-specific. J. Clin. Invest. 121, 1946-55 (2011)). Sequence information was obtained by Sanger sequencing.

1.7 Cloning of Recombinant Fully Human *Klebsiella Pneumoniae* O-Antigen Antibodies In order to produce fully human antibody, the IgHeavy and the corresponding IgLight genes were first cloned into human Igγ1 and Igκ or Igλ expression vectors, respectively. Therefore, the IgHeavy and the corresponding IgLight genes were specifically amplified from the primary PCR product using V-segment and J-segment specific primers containing appropriate restriction sites. The Ig gene PCR fragments were purified and digested using the respective restriction enzymes. Afterwards the Specific PCR Ig gene fragments were ligated into human Igγ1 and Igκ or Igλ expression vectors containing the respective human Ig constant region. The Igγ1 expression vector was equipped with secretory splice variant of the Ig constant, enabling the secretion of antibody into the cell culture supernatant.

In order to amplify successfully ligated expression vectors, the vectors were transformed into chemically competent *E. coli* (DH10B, Invitrogen). To select positive clones the whole solution were plated on LB plates containing 100 μg/ml Ampicillin and incubated for a minimum of 16 h at 37° C. To confirm correct insertion into the respective expression vector, we performed Insert check PCR on bacterial colonies using appropriate primer pairs and sent the product for purification and sequencing by Sanger sequencing (Eurofins genomics). First, the obtained sequence was checked for in-frame insertion of the respective Ig gene. Afterwards, the sequence was compared to the secondary PCR product sequence and excluded if PCR-prone additional point mutations in the Insert check PCR sequence were found. If point mutations found in the secondary PCR product were not present in the Insert-check PCR sequence, these mutations were not included into the analysis, due to a high likelihood that these mutations were generated early in the secondary PCR process. To amplify correctly cloned expression vectors, bacteria bearing the correct plasmid were inoculated into 4 ml TB (Gibco) containing 75 μg/ml Ampicillin in 13 ml culture tubes (Sarstedt) and grown for a minimum of 16 h at 37° C. at 180 rpm. The plasmid DNA was extracted using the Nucleospin Kit (Macherey & Nagel) according to the manufacturer's instructions.

1.8 Expression of Recombinant Fully Human *Klebsiella Pneumoniae* O3-Antigen Antibodies The fully human IgG1 antibodies were produced by Polyethylenimine—(PEI) mediated transfection of adherent and non-adherent human embryonic kidney 293 cells, HEK293T or HEK293S (Invitrogen), respectively.

1.8.1 Mammalian Cell Culture

HEK293T were cultured at 37° C. in 5% $CO_2$ in 25 ml DMEM GlutaMAX media containing 10% (v/v) FCS and 1× Antibiotic/Antimycotic (Gibco), whereas HEK293S cells were cultured at 37° C. in 5% $CO_2$ in 20 ml Freestyle medium (Gibco) at 180 rpm in 50 ml Bioreactors (TPP).

1.8.2 PEI-Mediated Transfection of HEK293T Cells

The cationic polymer PEI was used for transient gene transfer to HEK293T cells. Therefore, 10-15 μg IgH vector was mixed with equal amount of its corresponding IgL vector and 50 μl/μg total DNA of 150 mM sterile sodium chloride solution was added. Subsequently PEI [0.6 mg/ml] was added in a 3:1 (w/w) DNA to PEI ratio. The solution was immediately vortexed for 10 s and incubated at room-temperature for 10 min. In the meantime, plates were washed with 10 ml DMEM Glutamax pre-warmed to 37° C. to remove residual bovine serum antibodies. Thus, 25 ml pre-warmed expression media (DMEM Glutamax containing 1× Antibiotic/Antimycotic (Gibco) and 1× serum-free media supplement Nutridoma (Roche)) was added and the cells were incubated at 37° C. in 5% $CO_2$ until further use. Hence, the transfection mix was added drop-wise to the cells and the cells were incubated for 3.5 days. Subsequently, the antibody secreted into the supernatant was harvested and the cells were again incubated with 25 ml expression media. The supernatants were centrifuged at 4000 g to remove cell debris and transferred into a sterile 50 ml centrifuge tube (Sarstedt).

1.8.3 PEI-Mediated Transfection of HEK293S Cells

HEK293S cells were transiently transfected using the cationic polymer PEI. 10 ml HEK293S cells were seeded at $1.5 \times 10^6$ Cells/ml in Freestyle 293 Expression medium the day before transfection. After 16 h, the cell number was determined to be approximately $2.5 \times 10^6$ Cells/ml using a Thoma chamber. Thus, 10-15 μg IgH vector was mixed with equal amount of its corresponding IgL vector and added to the cell suspension. Subsequently cells were incubated an additional 5 min. To transfect the prepared cells PEI [0.6 mg/ml] was added in a 3:1 (w/w) DNA to PEI ratio. After 24 h 10 ml Ex-Cell medium (Gibco) containing 4 mM L-Glutamine (Gibco) was added to the cells and incubate for 5 days at 37° C. in 5% $CO_2$. The supernatants were centrifuged at 4000 g to remove cell debris and transferred into a sterile 50 ml centrifuge tube (Sarstedt).

1.9 Antibody Purification

In order to purify the secreted antibody from cell culture supernatant 12.5 μl Protein-G-coupled beads (GE Healthcare) per 10 ml antibody containing supernatant were washed with 50 ml ice-cold sterile 1×PBS pH=7.4 (Gibco) by centrifugation at 4000 g 4° C. for 10 min. The supernatant was carefully removed from the beads and an appropriate volume of 100 μl/sample was left in the centrifugation tube and added to the antibody supernatants. The mixture was incubated for at least 12 h at 4° C. on a rotator. Hence, the beads were harvested by centrifugation at 4000 g 4° C. for 10 min and the supernatant was carefully removed and added into a new sterile 50 ml centrifugation tube if needed. The beads were added onto a chromatography column (Bio-Rad) which has been equilibrated with 2 ml of ice-cold PBS. The columns were emptied by gravity-flow or by applying pressure with the thumb. Beads were washed with 1.5 ml ice-cold PBS. Thus, antibody was released from Protein-G into a 1.5 ml tube by a low pH pulse applying 450 μl sterile 0.1M Glycine pH=3 for 3 min and the solution was buffered by adding a 1:10 equivalent of a sterile 1M Tris solution pH=8. The procedure was repeated using 225 μl Glycine solution and eluted into a second sterile 1.5 ml tube. The pH=7.4-8.0 of the solution was confirmed by adding approximately 10 μl solution onto a small pH indicator strip (Sigma).

1.10 Antibody Concentration Measurement

Antibody concentrations in purified fractions were measured by Enzyme-linked immunosorbent assay (ELISA). Therefore a 96-well high-binding plate (Costar) was coated with 50 μl 1:500 dilution of a goat anti-human IgG Fcγ-fragment specific capture antibody (Dianova) for at least 12 h at 4° C. Thus, the plates were washed 3-times with deionized water and 200 μl blocking buffer (1×PBS, 0.05% Tween 20 and 1 mM EDTA) was added per well for 1 h. After additional 3-times washing, the plates were incubated with eight 50 μl 1:2.5 serial antibody dilutions in PBS and incubated for 1 h. Two serial dilutions of human IgG from human plasma (Sigma) starting with 1 μg/ml and 3 μg/ml served as a standard. After washing, 50 μl of a 1:1000

HRP-coupled goat anti-human IgG secondary antibody was added for 1 h. After an additional washing step, 100 μl HRP ABTS substrate was added and the amount of bound antibody was detected as the optical density at 405 nm.

2. Antibody Reactivity Measurement

Purified monoclonal antibodies were tested for binding to *K. pneumoniae* LPS O-antigen by ELISA or Western Blot.

2.1 O-Antigen ELISA

In order to immobilize biotinylated O-antigen samples, high-binding 96-well ELISA Plates (Costar) were coated overnight with 50 ul of 1 μg/ml Streptavidin (NEB) in PBS. Subsequently, plates were washed 3-times in PBS before adding 50 μl of 1 μg/ml biotinylated O-antigen of *Klebsiella pneumoniae* strains. The O-antigen was prepared from the following strains: O3:K- or O1 (43816, ATCC), O2 gtr-Kp26 (clinical isolate) and O2 gtr+ (PCM-27, Polish Collection of Microorganisms), respectively.

After incubation for 1 h at room-temperature, plates were washed and incubated with 200 μl 2% BSA in PBS for 1 h at room-temperature. After washing, 1:4 serial dilutions of recombinant human IgG1 antibodies with a starting concentration of 4 μg/ml were added to the plate for 1 h at room-temperature. After an additional washing step, concentration-dependent binding was detected using 50 μl 1:1000 goat anti-human IgG Fc HRP-coupled (Jackson) secondary antibody diluted in blocking buffer. After washing, 100 μl HRP ABTS substrate was added and antibody binding was detected as optical density at 405 nm. A non-polyreactive mature naïve antibody, which has been previously characterized (Wardemann et al. Science 2003, 301(5638):1374-7), served as negative control.

2.2 Streptavidin ELISA

Specificity of antigen-binding was determined by binding to the unrelated protein Streptavidin by ELISA. The ELISA was performed as described in the O-antigen ELISA section, but instead of incubating the plate with biotinylated O-antigen dilutions 1×PBS was used.

2.3 Whole LPS Immunoblot:

2 ug LPS/sample of *Klebsiella pneumoniae* O-serotypes was diluted in SDS-containing loading dye (NEB) and heated for 5 min to 95° C. before applied to a gradient SDS-PAGE (anyKd Bio-Rad). LPS was transferred onto a nitrocellulose membrane and fixed by complete drying of the membrane. After re-activation of the membrane and an additional washing step, the membrane was placed overnight in a 4% BSA in TBS solution. Thus, the membrane was cut with a scalpel into appropriate pieces and incubated in a 2 ug/ml monoclonal human IgG1 antibody in TBS solution for 1.5 h at room-temperature. Subsequently, the membrane was washed 2-times with TBS for 5 min and incubated with anti-human IgG Fc HRP-coupled secondary antibody 1:10000 in TBS containing 1% BSA. After washing 3-times with TBS for 5 min, binding was detected using luminol-based detection (Pierce).

2.4 Ig Gene Analysis:

Human Ig genes were identified using the Ig gene reference database of IGMT Version 1.2.1 embedded into the NCBI Ig Blast using the IMGT or Kabat CDR definitions (M.-P. Lefranc et al., IMGT unique numbering for immunoglobulin and T cell receptor variable domains and Ig superfamily V-like domains. Dev. Comp. Immunol. 27, 55-77 (2003)). The best matched germline hit was identified. Somatic hypermutations (SHM) were counted from the end of the primer-binding region until the end of the IGHV, IGKV, or IGLV gene. Insertions or deletions regardless of their length were counted as one SHM.

2.5 Bioinformatics:

Single cell sort fluorescence index data was recorded using BD FACSDIVA 7 V8.0.1 software and extracted using the flowCore package for R. (P. Ellis et al., flowCore: Basic structures for flow cytometry data (2016)). Plots were produced using Prism v6, Illustrator CS6 v16.0.3 (Adobe), Photoshop CS6 (Adobe) and R using the ggplot2 package. (H. Wickham, ggplot2: Elegant Graphics for Data Analysis (Springer-Verlag New York, 2009)).

Results

Fully Human Anti-*Klebsiella Pneumoniae* Lipopolysaccharide O3-Antigen Antibodies Biotinylated antigens in combination with fluorophore-coupled Streptavidin for their detection have been extensively applied to identify and isolate protein antigen-reactive B cells using flow cytometry (J. F. Scheid et al., A method for identification of HIV gp140 binding memory B cells in human blood. J. Immunol. Methods. 343, 65-7 (2009); O. L. Rojas, C. F. Narváez, H. B. Greenberg, J. Angel, M. A. Franco, Characterization of rotavirus specific B cells and their relation with serological memory. Virology. 380, 234-42 (2008); P. F. Kerkman et al., Identification and characterisation of citrullinated antigen-specific B cells in peripheral blood of patients with rheumatoid arthritis. Ann. Rheum. Dis. 75, 1170-1176 (2016)).

Figure 3C:
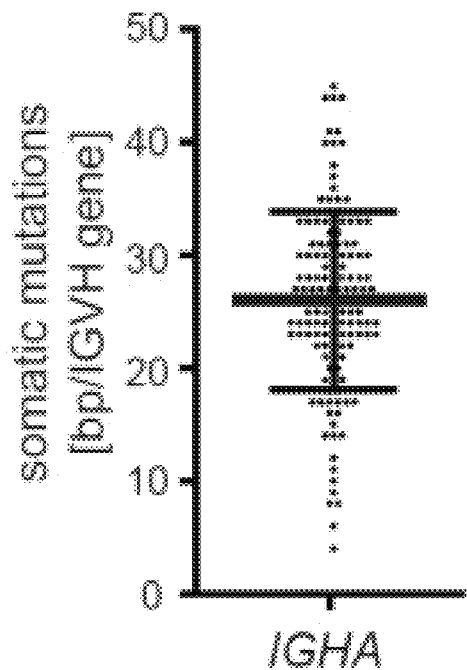
Figure 3D:
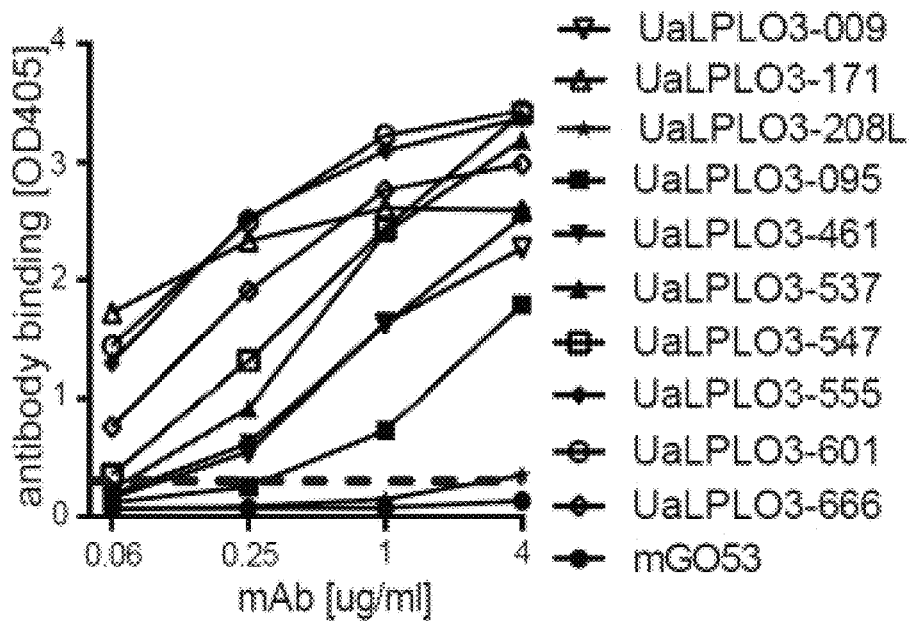
Figure 3E:
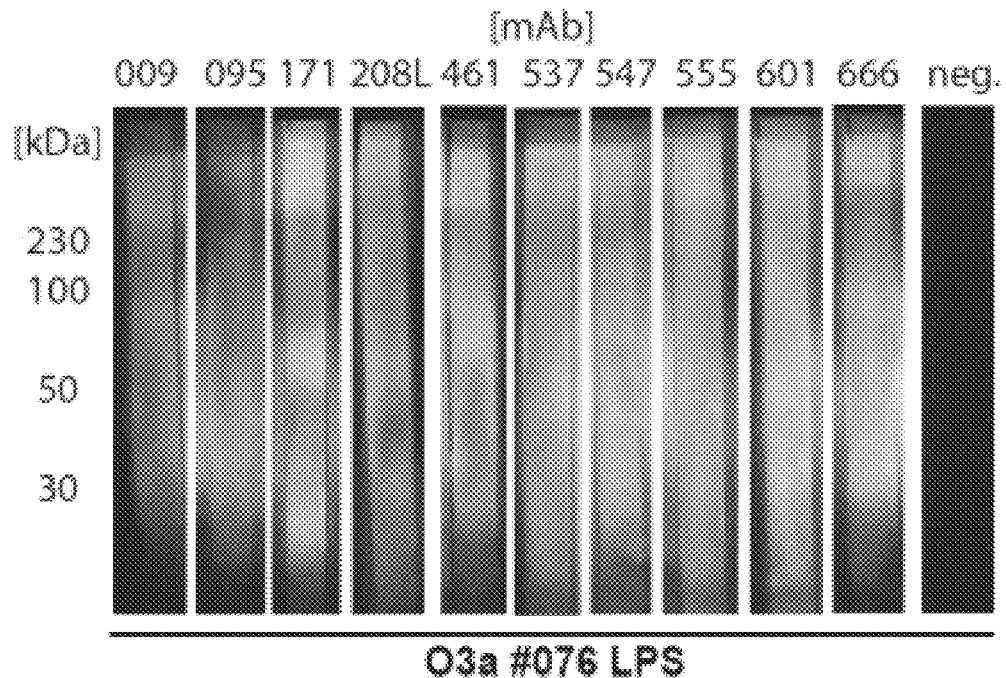
Figure 3F:
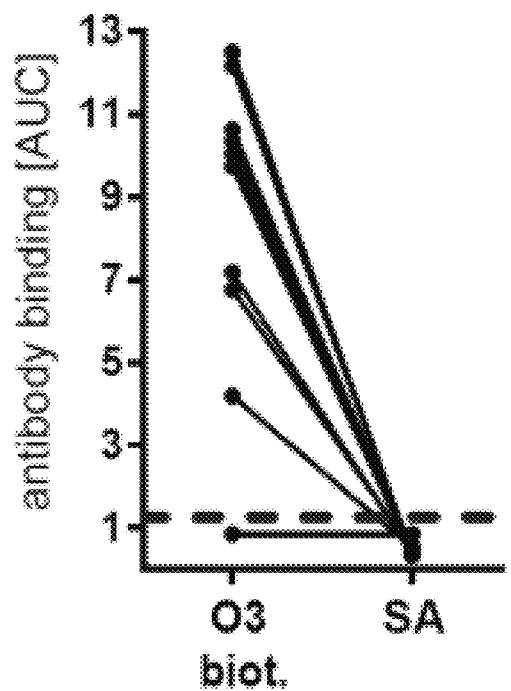

Here, biotinylated *K. pneumoniae* O3 O-polysaccharide was used as bait and Streptavidin-conjugated fluorophores were used to identify and isolate O3 O-antigen-reactive B cells. A rare population of O-antigen-binding plasmablasts was detected within the human intestinal lamina propria B cell pool by flow cytometry (FIG. 3b). Single O-antigen-binding B cells were isolated by fluorescence-activated cell sorting, their respective Ig heavy and associated Ig light chain genes were amplified by RT-PCR and Ig gene information was obtained by Sanger sequencing. The data show that the majority of O-antigen-reactive lamina propria plasmablast express IgA antibodies with various degrees of IGHV gene somatic hypermutations (FIG. 3c). Ten monoclonal antibodies were cloned and recombinantly expressed from IgA plasmablasts as IgG1. All antibodies showed concentration-dependent binding to the biotinylated O3-antigen bait in ELISA (FIG. 3d) and whole O3a LPS in Western Blot (FIG. 3d and FIG. 3e) but lacked detectable levels of reactivity with Streptavidin by ELISA (FIG. 3f). Ig gene features are provided in the table shown in FIG. 3g.

Example 2

Surface Binding of O3 Group Cross-Reactive Antibodies

Binding of selected antibodies to live *K. pneumoniae* strains belonging to the 3 different O3 serogroups was confirmed with Flow Cytometry. Overnight grown bacteria were diluted and grown to mid-log phase (OD600=0.5), washed in HBSS and used for surface staining. $2\times10^6$ bacteria were re-suspended in HBSS containing 0.5% BSA+ 0.01% sodium azide, and stained with mAbs for 30 minutes on ice. Samples were washed twice in HBSS-buffer containing BSA and sodium azide, re-suspended in HBSS containing 4 μg/mL AlexaFluor 488-conjugated goat anti-human IgG secondary antibody and incubated for 30 minutes on ice. After washing, samples were resuspended in HBSS containing 5 nM SYTO-62 dye and incubated for 10 minutes on ice before analysis on the Cytoflex flow cytometer.

All tested mAbs showed binding to live *K. pneumoniae* strains expressing one of the 3 different O3 type antigens, but with different intensity (FIG. 4). While mAbs MPG-547 (herein also referred to as UaLPLO3-547), 555 (herein also referred to as UaLPLO3-555) and 601 (herein also referred to as UaLPLO3-601) showed strong binding even at concentration as low as 1 µg/ml, antibodies MPG-095 (herein also referred to as UaLPLO3-095) and 208L (herein also referred to as UaLPLO3-208 or UaLPLO3-208L) bound the strains with considerable lower intensity. The highest signal intensity was detected with MPG-601.

Antibody binding characteristics were investigated by biolayer inferometry (BLI).

Antibody binding was measured by immobilizing biotinylated O3a polysaccharide antigen (purified from strain PCM-11) on streptavidin sensors (ForteBio, Pall Life Sciences) to give a loading of ~0.3 nm and monitoring the association of the human mAbs (10 µg/mL) to the preloaded sensors for 10 min in DPBS, pH 7.2 containing 1% bovine serum albumin (BSA), followed by dissociation (10 min) in the same buffer. All experiments were performed at 30° C. The KD, kon and koff values were determined using the Data Analysis 7 software (ForteBio, Pall Life Sciences) by fitting simultaneously the association and dissociation curves to a 1 to 1 binding model. Response values below 0.05 nm were considered negative.

The KD, kon and koff values are summarized in the following table. Confirming the results of the surface staining experiments, mAbs MPG-601, 547 and 555 showed the highest affinity (KD<1.00E-08) to biotinylated O3a antigen. Besides their higher KD values, mAbs MPG-095 and 208L showed also the fastest dissociation, and biphasic kinetic curve profiles, and therefore a partial curve fit was performed for these mAbs. No binding to the negative control antigen was observed with any of the mAbs.

TABLE

Binding characteristic of mAbs measured by ForteBio.

| Sample | Loading Sample | Response | KD(M) | kon(1/Ms) | kdis(1/s) | Fit |
|---|---|---|---|---|---|---|
| MPG-601 | Biotinylated O3a (PCM-11) | 8.5021 | 2.97E−09 | 5.82E+04 | 1.73E−04 | Full, 600 sec association, 600 sec dissociation |
| MPG-547 | Biotinylated O3a (PCM-11) | 6.9796 | 1.73E−08 | 3.94E+04 | 6.82E−04 | Full, 400 sec association, 200 sec dissociation |
| MPG-555 | Biotinylated O3a (PCM-11) | 7.4606 | 1.33E−08 | 7.39E+04 | 9.82E−04 | Full, 400 sec association, 200 sec dissociation |
| MPG-095 | Biotinylated O3a (PCM-11) | 1.5243 | 1.71E−07 | 8.00E+04 | 1.37E−02 | Partial, 250 sec association, 400 sec dissociation |
| MPG-208L | Biotinylated O3a (PCM-11) | 4.4225 | 1.51E−07 | 3.91E+04 | 5.89E−03 | Partial, 250 sec association, 400 sec dissociation |

Example 3

In Vitro Neutralization of O3 LPS

Functional activity of O3 specific mAbs was tested in an in vitro assay.

A commercial reporter cell line (HEK-Blue™ TLR4, Invivogen) was used to detect Toll like receptor 4 (TLR-4) signaling triggered by purified LPS according to the manufacturer's instructions. Twenty-five µl of mAb (diluted in HEK Blue™ medium) were mixed with 25 µl of freshly thawed purified LPS. O3 LPS derived from strains belonging to different O3 subgroups (PCM-11 (O3a), Kp14 (O3), Kp81 (O3b)). LPS solutions were prepared at 4, 10 and 0.8 ng/ml final concentration respectively in HEK Blue™ medium. The mixture were transferred into clear 96-well half-area plates and incubated at room temperature for 30 minutes. Afterwards, 50 µl suspension of HEK-Blue™ cells were added to the reaction mixes (~50,000 cells/well). Plates were wrapped in aluminium foil and incubated overnight (16-18 hours) at 37° C. with 5% CO2. On the following day optical density was measured at 630 nm and reporter protein level (secreted embryonic alkaline phosphatase—SEAP) over mock was calculated. Percent inhibition of SEAP induction relative to no antibody controls was calculated and plotted at different mAb concentrations. As positive control polymyxin B (PMB-Sulfate, FLUKA Cat. #81334) was used similarly to the tested mAbs. As negative control, an irrelevant mAb was included.

Although with different efficacy of neutralization, all antibodies exhibited dose dependent inhibition of the TLR-4 signaling through neutralization of all tested LPS (FIG. 5a). The efficacy showed also a good correlation with the affinities as measured by BLI. Importantly, mAb MPG-601 exhibited the highest neutralizing potential exceeding that of polymyxin B by 2 log.

Example 4

Serum Bactericidal Activity

To explore the phagocyte independent bactericidal activity of O3 mAbs, we tested MPG-601 in a so-called serum bactericidal assay (SBA). Clinical isolates of *K. pneumoniae* (Kp14 and Kp81) were incubated in 50% human serum depleted of pre-existing specific antibodies in the presence of 2.5 µg/ml MPG-601 or an irrelevant control human IgG1 mAb. Serum from two healthy individuals were tested. The experiments confirmed that MPG-601 elicits significant complement-mediated bacterial killing in both human sera compared to an isotype matched mAb with irrelevant specificity (FIG. 5b).

Example 5

Protective Efficacy of O3 mAbs In Vivo

Groups of 5 mice were passively immunized intraperitoneally with 200 or 20 µg of O3 specific mAbs or an irrelevant mAb as negative control. 24 h later mice were sensitized to endotoxin by intraperitoneal administration of 20 mg of GalN and simultaneously challenged with a lethal dose of *K. pneumoniae* strain Kp81 (O3b). Mortality was monitored for 14 days.

All mAbs, except MPG-208L showed protection at the higher dose (FIG. 6A). On the other hand, MPG-601 showed protection even at 20 µg/mouse dose (FIG. 6B), which is in good correlation with its high affinity and outstanding in vitro LPS neutralization potency.

Example 6

Selection of 5 Exemplary mAbs

Specificity of the mAbs derived from B-cell sorting was determined in immunoblot. LPS molecules purified from O3, O3a, O3b and O5 strains were separated by SDS-PAGE, followed by transfer to polyvinylidene difluoride membrane. Membranes were reacted with 1 µg/ml of human mAbs and secondary HRP-labelled goat anti-human IgG. Blots were developed by ECL reagent. Binding of the mAbs to the different LPS molecules is summarized in the table.

Antibodies identified as O3-group cross-reactive were compared functionally in an in vitro LPS neutralization assay. The same method was used, as described in Example 3.

LPS used in the neutralization assay derived from strain Kp81 (O3b). Percent inhibition of SEAP induction relative to no antibody controls was calculated and plotted at 10 µg/ml and at 100 µg/ml mAb concentrations.

Based on neutralizing capacity, five mAbs with the highest inhibition of SEAP induction were selected for further testing described in the previous examples.

Example 7

Generation of Functional Sequence Variants of Anti-*Klebsiella pneumonia* O3-Antigen Antibodies to Remove Potential Sequence Liabilities Mutants of MPG-601 are be generated to address potential manufacturability issues identified by in silico sequence analysis: MPG-601 C108S to remove the unpaired Cys in HCDR3; MPG-601 H97Y to replace the rare His residue found at this position with the more commonly observed Tyr; and finally a double mutant containing both of the mutations MPG-601 C108S H97Y. The mutagenesis is performed according to standard techniques using Quick Change XL Site-Directed Mutagenesis kit (Agilent, #200521).

These 3 mutants and the original wild-type (parent) mAb are expressed in CHO cells according to standard monoclonal antibody expression techniques. The expression yield (measured from the CHO cell's supernatant by western blot) and the monomer content (measured by SEC-HPLC according to standard methods) of the mutants are compared to that of the wild-type (parent) mAb. Additionally as described in example 2, mutants are tested in Flow Cytometry for binding to the surface of strains expressing one of the O3, O3a or O3b O-antigen or an irrelevant O-antigen. The functional activity of the mutants is compared to the activity of the wild-type (parent) mAb in the in vitro LPS neutralization assay as described in example 3 to exclude major changes in binding or efficacy due to the introduced mutations.

REFERENCES

1. Trautmann M, Ruhnke M, Rukavina T, Held T K, Cross A S, Marre R, Whitfield C. 1997. O-antigen seroepidemiology of *Klebsiella* clinical isolates and implications for immunoprophylaxis of *Klebsiella* infections. Clin. Diagn. Lab Immunol. 4:550-555.
2. Hansen D S, Mestre F, Alberti S, Hernandez-Alles S, Alvarez D, Domenech-Sanchez A, Gil J, Merino S, Tomas J M, Benedi V J. 1999. *Klebsiella pneumoniae* lipopolysaccharide O typing: revision of prototype strains and O-group distribution among clinical isolates from different sources and countries. J. Clin. Microbiol. 37:56-62.
3. Vinogradov E, Frirdich E, MacLean L L, Perry M B, Petersen B O, Duus J O, Whitfield C. 2002. Structures of lipopolysaccharides from *Klebsiella pneumoniae*. Eluicidation of the structure of the linkage region between core and polysaccharide O chain and identification of the residues at the non-reducing termini of the O chains. J. Biol. Chem. 277:25070-25081.
4. Kubler-Kielb J, Whitfield C, Katzenellenbogen E, Vinogradov E. 2012. Identification of the methyl phosphate substituent at the non-reducing terminal mannose residue of the O-specific polysaccharides of *Klebsiella pneumoniae* O3, *Hafnia alvei* PCM 1223 and *Escherichia coli* O9/O9a LPS. Carbohydr. Res. 347:186-188.
5. Greenfield L K, Richards M R, Li J, Wakarchuk W W, Lowary T L, Whitfield C. 2012. Biosynthesis of the polymannose lipopolysaccharide O-antigens from *Escherichia coli* serotypes O8 and O9a requires a unique combination of single- and multiple-active site mannosyltransferases. J. Biol. Chem. 287:35078-35091.
6. Greenfield L K, Richards M R, Vinogradov E, Wakarchuk W W, Lowary T L, Whitfield C. 2012. Domain organization of the polymerizing mannosyltransferases involved in synthesis of the *Escherichia coli* O8 and O9a lipopolysaccharide O-antigens. J. Biol. Chem. 287:38135-38149.
7. Kido N, Kobayashi H. 2000. A single amino acid substitution in a mannosyltransferase, WbdA, converts the *Escherichia coli* O9 polysaccharide into O9a: generation of a new O-serotype group. J. Bacteriol. 182:2567-2573.
8. Parolis L A, Parolis H, Dutton G G. 1986. Structural studies of the O-antigen polysaccharide of *Escherichia coli* O9a. Carbohydr. Res. 155:272-276.
9. Lukasiewicz J, Dzieciatkowska M, Niedziela T, Jachymek W, Augustyniuk A, Kenne L, Lugowski C. 2006. Complete lipopolysaccharide of Plesiomonas shigelloides O74:H5 (strain CNCTC 144/92). 2. Lipid A, its structural variability, the linkage to the core oligosaccharide, and the biological activity of the lipopolysaccharide. Biochemistry 45:10434-10447.
10. Curvall M, Lindberg B, Lonngren J, Nimmich W. 1973. Structural studies on the *Klebsiella* O group 3 lipopolysaccharide. Acta Chem. Scand. 27:2645-2649.

The invention claimed is:

1. A cross-neutralizing monoclonal antibody that comprises an antigen-binding site and specifically recognizes a cross-reactive epitope of the lipopolysaccharide (LPS) antigen structure of *Klebsiella pneumoniae*, which is an O3b epitope, cross-reacting with an O3a epitope, wherein said antigen binding site comprises an antibody heavy chain variable region (VH), which comprises VH-CDR1 to VH-CDR3 sequences, and an antibody light chain variable region (VL), which comprises VL-CDR1 to VL-CDR3 sequences, said antibody:

A)
is an antibody comprising
a) VH-CDR1 consisting of the amino acid sequence SEQ ID NO:44; and
b) VH-CDR2 consisting of the amino acid sequence SEQ ID NO:45; and
c) VH-CDR3 consisting of the amino acid sequence of SEQ ID NO:46; and
d) VL-CDR1 consisting of the amino acid sequence SEQ ID NO:56; and
e) VL-CDR2 consisting of the amino acid sequence SEQ ID NO:57; and
f) VL-CDR3 consisting of the amino acid sequence of SEQ ID NO:58; or B) is a functionally active variant antibody of the foregoing, wherein the functionally active variant antibody specifically recognizes said cross-reactive epitope, and comprises
a) the VH-CDR1 sequence SEQ ID NO:75; and
b) the VH-CDR2 sequence SEQ ID NO:76; and
c) the VH-CDR3 sequence SEQ ID NO:77; and
d) the VL-CDR1 sequence SEQ ID NO:78; and
e) the VL-CDR2 sequence SEQ ID NO:57; and
f) the VL-CDR3 sequence SEQ ID NO:79, wherein CDR sequences are according to IMGT.

2. The antibody of claim 1, which comprises
a) a VH consisting of the amino acid sequence which is any one of SEQ ID NO:11, 68, 69, or 70; and
b) a VL consisting of the amino acid sequence SEQ ID NO:16.

3. The antibody of claim 1, wherein
a) the O3b epitope is incorporated in the LPS O3b antigen of *Klebsiella pneumoniae* comprising the structure of Formula (I), including one or more O3b antigen trimannose homopolymer repeating units, wherein Formula (I) is:

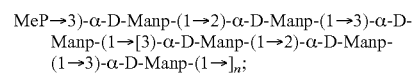
MeP→3)-α-D-Manp-(1→2)-α-D-Manp-(1→3)-α-D-Manp-(1→[3)-α-D-Manp-(1→2)-α-D-Manp-(1→3)-α-D-Manp-(1→]$_n$;

b) the O3a epitope is incorporated in the LPS O3a antigen of *Klebsiella pneumoniae* comprising the structure of Formula (II), including one or more O3a antigen tetramannose homopolymer repeating units, wherein Formula (II) is:

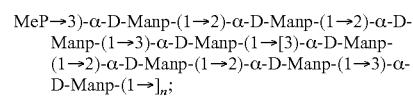
MeP→3)-α-D-Manp-(1→2)-α-D-Manp-(1→2)-α-D-Manp-(1→3)-α-D-Manp-(1→[3)-α-D-Manp-(1→2)-α-D-Manp-(1→2)-α-D-Manp-(1→3)-α-D-Manp-(1→]$_n$;

and
c) the O3 epitope is incorporated in the LPS O3 antigen of *Klebsiella pneumoniae* comprising the structure of Formula (III), including one or more O3 antigen pentamannose homopolymer repeating units, wherein Formula (III) is:

MeP→3)-α-D-Manp-(1→2)-α-D-Manp-(1→2)-α-D-Manp-(1→2)-α-D-Manp-(1→3)-α-D-Manp-(1→[3)-α-D-Manp-(1→2)-α-D-Manp-(1→2)-α-D-Manp-(1→2)-α-D-Manp-(1→3)-α-D-Manp-(1→]$_n$ wherein
MeP is methyl phosphate; and
n is 0-50.

4. The antibody of claim 1, which has an affinity to bind the O3a epitope with a $K_D$ of less than $10^{-6}$ M as determined by biolayer interferometry for bivalent binding.

5. The antibody of claim 1, which is neutralizing endotoxin of *Klebsiella pneumoniae* strains expressing LPS molecules comprising any of the O3b, O3a, or O3 epitopes.

6. The antibody of claim 1, which is any one of a full-length antibody, an antibody fragment thereof, or a fusion protein, each comprising at least VH and VL antibody domains incorporating a binding site recognizing the cross-reactive epitope.

7. The antibody of claim 1, which is of human origin, or an affinity matured variant thereof.

8. The antibody of claim 1, for use in treating a subject at risk of or suffering from *K. pneumonia* infection or colonization to limit the infection in the subject or to ameliorate a disease condition resulting from said infection.

9. A pharmaceutical preparation comprising the antibody of claim 1, and a pharmaceutically acceptable carrier or excipient in a parenteral formulation.

10. An isolated nucleic acid encoding the antibody of claim 1.

11. An expression cassette or a plasmid comprising a coding sequence to express a proteinaceous construct comprising a VH and/or VL of the antibody of claim 1.

12. A host cell comprising the expression cassette or a plasmid of claim 11.

13. A method of producing the antibody of claim 1, wherein a host cell comprising an expression cassette or a plasmid comprising a coding sequence to express a proteinaceous construct comprising a VH and/or VL of said antibody is cultivated or maintained under conditions to produce said antibody.

14. The antibody of claim 1, which comprises

A
a) a VH consisting of the amino acid sequence which SEQ ID NO:14; and
b) a VL consisting of the amino acid sequence SEQ ID NO:19; or B
a) a VH consisting of the amino acid sequence which SEQ ID NO:15; and
b) a VL consisting of the amino acid sequence SEQ ID NO:20.

15. The antibody of claim 4, which has an affinity to bind the O3a epitope with a $K_D$ of less than $10^{-7}$M as determined by biolayer interferometry for bivalent binding.

16. The antibody of claim 7, wherein the antibody is a non-naturally occurring antibody which comprises an artificial amino acid sequence.

17. The antibody of claim 16, wherein the antibody is an IgA antibody or an IgA to IgG isotype switch variant thereof.

18. The antibody of claim 8, for treatment or prophylaxis of any of primary and secondary bacteremia, pneumonia, urinary tract infection, liver abscess, peritonitis, or meningitis.

19. The antibody of claim 18, wherein the subject is an immunocompromised or immunosuppressed patient, or a contact thereof.

* * * * *